US010730833B2

(12) United States Patent
Tang et al.

(10) Patent No.: US 10,730,833 B2
(45) Date of Patent: Aug. 4, 2020

(54) SYNTHESIS OF DIINDOLYLMETHANES AND INDOLO[3,2-B]CARBAZOLES, COMPOUNDS FORMED THEREBY, AND PHARMACEUTICAL COMPOSITIONS CONTAINING THEM

(71) Applicant: Wisconsin Alumni Research Foundation, Madison, WI (US)

(72) Inventors: Weiping Tang, Middleton, WI (US); Xiaoxun Li, Madison, WI (US); Dongxu Shu, Lake Bluff, IL (US); Gabrielle N. Winston-McPherson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/946,066

(22) Filed: Apr. 5, 2018

(65) Prior Publication Data

US 2018/0222861 A1 Aug. 9, 2018

Related U.S. Application Data

(62) Division of application No. 14/818,960, filed on Aug. 5, 2015, now Pat. No. 9,969,686.

(60) Provisional application No. 62/107,707, filed on Jan. 26, 2015, provisional application No. 62/033,410, filed on Aug. 5, 2014.

(51) Int. Cl.
C07D 209/14 (2006.01)
C07D 403/06 (2006.01)
C07D 405/14 (2006.01)
C07D 209/12 (2006.01)

(52) U.S. Cl.
CPC ......... C07D 209/14 (2013.01); C07D 209/12 (2013.01); C07D 403/06 (2013.01); C07D 405/14 (2013.01)

(58) Field of Classification Search
CPC .................................................... C07D 209/14
See application file for complete search history.

(56) References Cited

U.S. PATENT DOCUMENTS

| 9,969,686 | B2* | 5/2018 | Tang | C07D 209/14 |
| 2004/0043965 | A1* | 3/2004 | Jong | C07D 209/08 514/80 |
| 2004/0053987 | A1 | 3/2004 | Giannini et al. | |
| 2010/0069355 | A1* | 3/2010 | Jong | A61K 31/407 514/210.21 |
| 2012/0283240 | A1 | 11/2012 | Jong et al. | |

OTHER PUBLICATIONS

Ackermann et al., Cationic Ruthenium(II) Catalysts for Oxidative C—H/N—H Bond Functionalizations of Anilines with Removable Directing Group: Synthesis of Indoles in Water, *Org. Lett.* 2012, vol. 14, No. 3, pp. 764-767.

Ali et al., Electrophile-Driven Regioselective Synthesis of Functionalized Quinolines, *Org. Lett.* 2011, vol. 13, No. 10, pp. 2598-2601.

Allegretti et al., Generation of ∀,∃-Unsaturated Platinum Carbenes from Homopropargylic Alcohols: Rearrangements to Polysubstituted Furans, *Organic Letters*, 2011, col. 13, No. 21, pp. 5924-5927.

Allegretti et al., Platinum-catalyzed cyclizations via carbine intermediates: syntheses of complementary positional isomers of isoxazoles, *Chem. Sci.* 2013, 4, 1053.

Barluenga et al., Recent Advances in the Synthesis of Indole and Quinoline Derivatives through Cascade Reactions, *Chem. Asian J.*, 2009, 4, pp. 1036-1048.

Beamer et al., Role of the aryl hydrocarbon receptor (AhR) in lung inflammation, *Semin. Immunopathol.* 2013, 35, pp. 693-704.

Bock, K.W., The human Ah receptor: hints from dioxin toxicities to deregulated target genes and physiological functions, *Biol. Chem.* 2013, 394(6), pp. 729-739.

Boudreault et al., New ondolo[3,2-b]carbazole derivatives for field-effect transistor application, *J. Mater. Chem.* 2009, 19, pp. 2921-2928.

Bruker-AXS. (2007-2014) APEX2 (Ver. 2014.1-1), SADABS (Jan. 2012), and SAINT+ (Ver. 8.32A) Software Reference Manuals. Bruker-AXS, Madison, Wisconsin, USA (Book—Copy Not Provided).

Busbee et al., Use of natural AhR ligands as potential therapeutic modalities against inflammatory disorders, *Nutrition Rev.* 2013, 71(6), 353-369.

Cao et al., Janus Kinase activation by cytokine oncostatin M decreases PCSK9 expression in liver cells, *J Lipid Res*, 2011, 52, 518-530.

Chang et al., Constitutive Activation of the Aromatic Hydrocarbon Receptor, *Mol. Cell Biol.* 1998, vol. 18, No. 1, pp. 525-535.

Ciofani et al., A validated regulatory network for Th17 cell specification. *Cell*, 151, pp. 289-303.

Clavier et al., Palladium-mediated [2+1] Cycloaddition of Norbornene Derivatives with Ynamides, *Adv. Synth. Catal.*, 2013, 355, pp. 403-408.

Crunkhorn, S. Trial watch: PCSK9 antibody reduces LDL cholesterol, *Nat Rev Drug Discov*, 2012, vol. 11, 11.

Cui et al., Regioselective Pd-catalyzed indolization of 2-bromoanilines with internal alkynes using phosphine-free ligands, *Tetrahedron Lett.*, 2008, 49, pp. 3458-3462.

(Continued)

*Primary Examiner* — Shawquia Jackson
(74) *Attorney, Agent, or Firm* — Joseph T. Leone, Esq.; DeWitt LLP

(57) ABSTRACT

Described is a method to make diindolylmethanes and indolyl/pyrrolylmethanes, The method includes the steps of contacting an ether comprising an arylpropargyl moiety and an amine-protected, substituted or unsubstituted aniline moiety with a substituted or unsubstituted indol or a substituted or unsubstituted pyrrole, in the presence of a metal-containing catalyst, for a time and at a temperature to cause an annulation/arylation cascade reaction that yields a diindolylmethane or a indolyl/pyrrolylmethane. The resulting compounds are effective to modulate activity of arylhydrocarbon receptors, to inhibit activity of PCSK9, and to stimulate secretion of glucagon-like peptide 1 in mammals.

7 Claims, No Drawings

(56) References Cited

OTHER PUBLICATIONS

Denison et al., Exactly the Same but Different: Promiscuity and Diversity in the Molecular Mechanisms of Action of the Aryl Hydrocarbon (Dioxin) Receptor, *Toxicol. Sci.* 2011, 124(1), pp. 1-22.
Dolomanov et al., OLEX2: a complete structure solution, refinement and analysis program, *J. Appl. Cryst.* 20099 42, pp. 339-341.
Donato et al., A Microassay for Measuring Cytochrome P450IA1 and P450IIB1 Activities in Intact Human and Rat Hepatocytes Cultured on 96-Well Plates, *Anal. Biochem.*, 1993, 213, pp. 29-33.
Fritz et al., The selective aryl hydrocarbon receptor modulator 6-methyl-1,3,8-trichlorodibenzofuran inhibits prostate tumor metastasis in TRAMP mice, *Biochem. Pharmacol.*, 2009, 77, pp. 1151-1160.
Gabriele et al., Recyclable catalytic synthesis of substituted quinolones: coper-catalyzed heterocyclization of 1-(2-aminoaryl)-2-yn-1-ols in ionic liquids, *Tetrahedron*, 2009, 65, pp. 8507-8512.
Dungan et al., Glucagon-Like Peptide 1-Based Therapies for Type 2 Diabetes: A Focus on Exenatide, *Clinical Diabetes*, 2011, 29 (1.
Greene, T.W., Protective Groups in Organic Synthesis (John Wiley & Sons, Inc., New York, 1991, ISBN 0-471-62301-6. See also the 5th edition of this same work, published under the title "Greene's Protective Groups in Organic Synthesis," ISBN-13: 978-1118057483, © 2014, John Wiley & Sons, Inc. Greene describes many nitrogen protecting groups, for example, amide-forming groups. In particular, see Chapter 1, Protecting Groups: An Overview, Chapter 2, Hydroxyl Protecting Groups, Chapter 4, Carboxyl Protecting Groups, and Chapter 5, Carbonyl Protecting Groups (Books— Copies Not Provided).
Gu et al., Facile One-Pot synthesis of Novel 6-Monosubstituted 5,11-Dihydroindolo[3,2-b]carbazoles and preparation of Different Derivatives, *Synlett*, 2006, pp. 1535-1538.
Gu et al., Facile One-Pot Synthesis of 6-Monosubstituted and 6,12-Disubstituted 5,11-Dihydroindoleo[3,2-b]carbazoles and Preparation of Various Functionalized Derivatives, *J. Org. Chem.*, 2007, 72, pp. 7207-7213.
Gu et al., Facile synthesis of novel indolo[3,2-b]carbazole derivatives and a chromogenic-sensing 5,12-dihydroindolo[3,2-b]carbazole, *Org. Biomol. Chem.*, 2008, 6, pp. 2484-2487.
Hahn, M. E., Aryl hydrocarbon receptors: diversity and evolution, *Chem. Biol. Interact.*, 2002, 141, pp. 131-160.
Han et al., Gallium(III)-Catalyzed Three-Component (4+3) Cycloaddition, *Angew. Chem. Int. Ed.*, 2012, 51, pp. 10390-10393.
Horton et al., PCSK9: a convertase that coordinates LDL catabolism, *J. Lipid Res.*, 2009, 50 Suppl, pp. S172-S177.
Inamoto et al., Synthesis of 3-Carboxylated Indoles through a Tandem Process Involving Cyclization of 2-Ethynylanilines followed by $CO_2$ Fixation in the Absence of Transition Metal Catalysts, *Org. Lett.*, 2012, vol. 14, pp. 2622-2625.
Ivanov et al., Transcriptional regulation of Th17 cell differentiation, *Semin Immunol*, 2007, 19, pp. 409-417.
Jeong et al., FICZ, a Tryptophan photoproduct, suppresses pulmonary eosiniophilia and Th2-type cytokine production in a mouse model of ovalbumin-induced allergic asthma, *Int. Immunopharmacol.*, 2012, 13, pp. 377-385.
Kiss et al., Natural Aryl hydrocarbon Receptor Ligands Control Organogenesis of Intestinal Lymphoid Follicles, *Science*, 2011, vol. 334, pp. 1561-1565.
Knölker et al., Isolation and synthesis of biologically Active Carbazole Alkaloids, *Chem. Rev.* 2002, 102, pp. 4303-4427.
Knutson et al., Response of Murine Epidermis to 2,3,7,8-Tetrachlorodibenzo-p-dioxin: Interaction if the Ah and hr Loci, *Cell*, 1982, vol. 30, pp. 225-234.
Kocienski, Philip J. Protecting Groups, (Georg Thieme Verlag Stuttgart, New York, 1994).
Kothandaraman et al., Gold-Catalyzed Cycloisomerization Reactions of 2-Tosylamino-phenylprop-1-yn-3-ols as a Versatile Approach for Indole Synthesis, *Angew. Chem. Int. Ed.*, 2010, 49, pp. 4619-4623.
Kothandaraman et al., Metal-free synthesis of 1H-indole-2-carbaldehydes by N-iodosuccinimide-mediated cyclization of 1-(2'-anilinyl)propr-2-yn-1-ols in water. A formal synthesis of (R)-calindol, *Tetrahedron*, 2013, 69, pp. 7471-7480.
Kramer et al., Malassezin, a Novel Agonist of the Aryl Hydrocarbon Receptor from the Yeast *Malassezia furfur*, Induces Apoptosis in Primary Human Melanocytes, *Chembiochem*, 2005, 6, pp. 860-865.
Li et al., Hepatocyte Nuclear Factor 1∀ Plays a Critical Role in PCSK9 Gene Transcription and Regulation by the Natural Hypocholesterolemic Compound Berberine, *J Biol Chem*, 2009, 284, pp. 28885-28895.
Li et al., Exogenous Stimuli Maintain Intraepithelial Lymphocytes via Aryl Hydrocarbon Receptor Activation, *Cell*, 2011, 147, pp. 629-640.
Lim et al., Glucagon-Like Peptide 1 Secretion by the L-Cell, *Diabetes*, vol. 55 (supplement 2), (Dec. 2006) pp. 870-877.
Luo et al., Synthesis of Furanophane Derivatives through [8+2]-Cyclo addition of Dienylisobenzofurans and Alkynes, *J. Am. Chem. Soc.* 2003, 125, pp. 1272012721.
Mane et al., The differentiation of human T(H)-17 cells requires transforming growth factor-beta and induction of the nuclear receptor ROR(t, *Nat Immunol*, 2008, vol. 9, pp. 641-649.
McDougal et al., Methyl-substituted diindolylmethanes as inhibitors of estrogen-induced growth of T47D cells and mammary tumors in rats, *Breast Cancer Res. Treat.*, 2001, 66, pp. 147-157.
Mehta et al., Potential protective mechanisms of aryl hydrocarbon receptor (AHR) signaling in benign prostatic hyperplasia, *Differentiation*, 2011, 82, pp. 211-219.
Mitchell et al., Timing is everything: Consequences of transient and sustained AhR activity, *Biochem. Pharmacol.*, 2009, 77, pp. 947-956.
Nguyen et al., The Search for Endogenous Activators of the Aryl hydrocarbon Receptor, *Chem. Res. Toxicol.*, 2008, 21, pp. 102-116.
Oda et al., Synthesis of N-Azolylindoles by Copper-Catalyzed C—H/N—H Coupling-Annulation Sequence of ≡-Alkynylanilines, *Org. Lett.*, 2012, vol. 14, pp. 664-667.
Ouyang et al., The biological functions of T helper 17 cell effector cytokines in inflammation, *Immunity*, 2008, 28, pp. 454-467.
Platon et al., Progress in Palladium-baseed catalytic systems for the sustainable synthesis of annulated heterocycles: a focus on indole backbones, *Chem. Soc. Rev.*, 2012, 41, pp. 3929-3968.
Poland et al., 2,3,7,8-Tetrachlorodibenzo-p-dioxin and Related Halogenated Aromatic Hydrocarbons: Examination of the Mechanism of Toxicity, *Annu. Rev. Pharmacol. Toxicol.*, 1982, 22, pp. 517-554.
Quintana et al., Control of $T_{reg}$ and $T_H17$ cell differentiation by the aryl hydrocarbon receptor, *Nature*, 2008, vol. 453, pp. 65-72.
Rindi et al., Development of Neuroendocrine Tumors in the Gastrointestinal Tract of Transgenic Mice, *Am. J. Pathol.*, 1990, vol. 136(6): pp. 1349-1363.
Safe et al., Role of the Aryl Hydrocarbon Receptor in Carcinogenesis and Potential as a Drug Target, *Toxicol. Sci.*, 2013, 135(1), pp. 1-16.
Saito et al., Platinum(II)-Catalyzed Generation and [3+2] Cycloaddition Reaction of ∀,∃-Unsaturated Carbene Complex Intermediates for the Preparation of Polycyclic Compounds, *Am. Chem. Soc.*, 2011, 133, pp. 689-691.
Schmidt et al., AH Receptor Signaling Pathways. *Annu. Rev. Cell Dev. Biol.*, 1996, 12, pp. 55-89.
Schmidt et al., Occurrence, Biogenesis, and Synthesis of biologically Active Carbazole Alkaloids, *Chem. Rev.*, 2012, 112, pp. 3193-3328.
Sheldrick, G. M., A Short History of SHELX, *Acta Cryst.*, 2008, A64, pp. 112-122.
Shu et al., Rhodium- and Platinum-Catalyzed [4+3] Cycloaddition with Concomitant Indole Annulation: synthesis of Cycloheptal[b]indoles, *Angew. Chem. Int. Ed.*, 2013, 52, pp. 3237-3240.
Shu et al., Platinum-Catalyzed Tandem Indole Annulation/Arylation for the Synthesis of Diindolylmethanes and Indolo[3,2-b]carbazoles, *Org. Lett.*, 2013, vol. 15, No. 16, 4162-4165.
Song et al., Nickel-catalyzed alykyne annulation by anilines: versatile indole synthesis by C—H/N—H functionalization, *Chem. Commun.*, 2013, 49, pp. 6638-6640.

(56) References Cited

OTHER PUBLICATIONS

Steinberg et al., Inhibition of PCSK9: a powerful weapon for achieving ideal LDL cholesterol levels, *Proc. Natl. Acad. Sci. U.S.A.*, 2009, vol. 106 No. 24, pp. 9546-9547.

Stevens et al., The aryl hydrocarbon receptor: a perspective on potential roles in the immune system, *Immunology*, 2009, 127, pp. 299-311.

Taber et al., Indole synthesis: a review and proposed classification, *Tetrahedron*, 2011, 67(38), pp. 7195-7210.

Tholander et al., Synthesis of 6-Formylindolo[3,2-b]carbazole, an Extremely Potent Ligand for the Aryl Hydrogen (Ah) Receptor, *Tetrahedron Letters*, 1998, 39, pp. 1619-1622.

Tholander et al., Syntheses of 6-Substituted Indolo[3,2-b]carbazoles, Including 6-Formylindolo[3,2-b]carbazole, an Extremely Efficient Ligand for the TCDD (Ah) Receptor, *Tetrahedron*, 1999, 55, 6243.

Van Tonder, J. J., Development of an in vitro mechanistic toxicity screening model using cultures hepatocytes, University of Pretoria Z.A., Thesis, 2011.

Van Voorhis et al., The Aryl Hydrocarbon Receptor: A Novel Target for Immunomodulation I Organ Transplantation, *Transplantation*, 2013, 95(8), pp. 983-990.

Vezina et al., AHR signaling in prostate growth, morhogenesis, and disease, *Biochem. Pharmacol.*, 2009, 77, pp. 566-576.

Vicente, R., Recent advances in indole syntheses: new routes for a classic target, *Org. Biomol. Chem.*, 2011, 9, pp. 6469-6480.

Vogel, R. A., PCSK9 inhibition: the next statin, *J Am Coll Cardiol*, 2012, 59, 2354-2355.

Wahlstrom et al., Synthesis of 2,3'-Diindolylmethanes and Substituted Indolo[3,2-b]carbazoles, *J. Synthesis*, 2004, No. 8, pp. 1187-1194.

Wahlstrom et al., Synthesis of Metabolites of the Ah Receptor Ligand 6-Formylindolo[3,2-b]carbazole, *Eur. J. Org. Chem.*, 2004, pp. 2593-2602.

Whyte et al., Ethoxyresorufin-O-deethylase (EROD) Activity in Fish as a Biomarker of Chmeical Exposure, *Crit. Rev. Toxicol.*, 2000, 30:4, pp. 347-570.

Wille et al., Lalassezin—A Novel Agonist of the Arylhydrocarbon Receptor from the Yeast *Malassezia furfur*, *Bioorg. Med. Chem.*, 2001, 9, pp. 955-960.

Wincent et al., The suggested Physilogic Aryl Hydrocarbon Receptor Actovator and Cytochrome P4501 Substrate 6-Formylindolo[3,2-b]carbazole is Present in Humans, *J. Biol. Chem.*, 2009, vol. 284, No. 5, pp. 2690-2696.

Xia et al., Palladium(II)-Catalyzed Tandem Cyclization/C—H Functionalization of Alkynes for the Synthesis of Functionalized Indoles, *J. Org. Chem.*, 2012, 77, pp. 9163-9170.

Zhang et al., A simple and Efficient Approach to the Synthesis of 2-Phenylquinazolines via $sp^3$ C—H Functionalization, *Org. Lett.* 2010, vol. No. 12, pp. 2841-2843.

\* cited by examiner

SYNTHESIS OF DIINDOLYLMETHANES AND INDOLO[3,2-B]CARBAZOLES, COMPOUNDS FORMED THEREBY, AND PHARMACEUTICAL COMPOSITIONS CONTAINING THEM

CROSS-REFERENCE TO RELATED APPLICATIONS

This is a divisional of co-pending application Ser. No. 14/818,960, filed Aug. 5, 2015, which claims priority to provisional application Ser. No. 62/107,707, filed Jan. 26, 2015, and to provisional application Ser. No. 62/033,410, filed Aug. 5, 2014, all of which are incorporated herein by reference.

FEDERAL FUNDING STATEMENT

This invention was made with government support under GM088285 awarded by the National Institutes of Health. The government has certain rights in the invention.

FIELD OF THE INVENTION

Disclosed herein are novel diindolyl compounds that are effective to modulate activity of arylhydrocarbon receptors, to inhibit activity of PCSK9, and to stimulate secretion of glucagon-like peptide 1 in mammals.

BACKGROUND

Indole is one of the most abundant heterocycles in bioactive natural products and pharmaceutical agents. Not surprisingly, numerous efforts have been devoted to the preparation of indoles from a diverse range of starting materials. For recent-reviews on indole synthesis, see: (a) Barluenga, J.; Rodriguez, F.; Fananas, F. J. Chem. Asian J. 2009, 4, 1036. (b) Taber, D. F.; Tirunahari, P. K. Tetrahedron 2011, 67, 7195. (c) Vicente, R. Org. Biomol. Chem. 2011, 9, 6469. (d) Platon, M.; Amardeil, R.; Djakovitch, L.; Hierso, J.-C. Chem. Soc. Rev. 2012, 41, 3929. For recent examples of indole annulations, see: (a) Cui, X.; Li, J.; Fu, Y.; Liu, L.; Guo, Q.-X. Tetrahedron Lett. 2008, 49, 3458. (b) Oda, Y.; Hirano, K.; Satoh, T.; Miura, M. Org. Lett. 2012, 14, 664. (c) Ackermann, L.; Lygin, A. V. Org. Lett. 2012, 14, 764. (d) Inamoto, K.; Asano, N.; Nakamura, Y.; Yonemoto, M.; Kondo, Y. Org. Lett. 2012, 14, 2622. (e) Xia, X.-F.; Wang, N.; Zhang, L.-L.; Song, X.-R.; Liu, X.-Y.; Liang, Y.-M. J. Org. Chem. 2012, 77, 9163. (f) Song, W.; Ackermann, L. Chem. Commun. 2013, 49, 6638. Most previous efforts, however, have focused on indole annulation alone. The efficiency of the synthesis can be increased significantly if the event of indole annulation is coupled with other transformations in a cascade manner. For example, a tandem indole annulation/(4+3) cycloaddition for the construction of both indole and a seven-membered ring simultaneously in the synthesis of cyclohepta[b]indoles is described in the literature. Shu, D.; Song, W.; Li, X.; Tang, W. Angew. Chem. Int. Ed., 2013, 52, 3237. For a synthesis of cyclohepta[b]indoles by a different type of (4+3) cycloaddition, see: Han, X.; Li, H.; Hughes, R. P.; Wu, J. Angew. Chem. Int. Ed. 2012, 51, 10390. Diindolylmethanes are not only present in natural products such as malassezin but also important precursors for other naturally occurring heterocycles such as indolocarbazoles 2 and 3a-3f: Wille, G.; Mayser, P.; Thoma, W.; Monsees, T.; Baumgart, A.; Schmitz, H. J.; Schrenk, D.; Polborn, K.; Steglich, W. Bioorg. Med. Chem. 2001, 9, 955. Kramer, H. J.; Podobinska, M.; Bartsch, A.; Battmann, A.; Thoma, W.; Bernd, A.; Kummer, W.; Irlinger, B.; Steglich, W.; Mayser, P. Chembiochem 2005, 6, 860. Wahlstrom, N.; Romero, I.; Bergman, J. Eur. J. Org. Chem. 2004, 2593. Knolker, H. J.; Reddy, K. R. Chem. Rev. 2002, 102, 4303. Schmidt, A. W.; Reddy, K. R.; Knoelker, H.-J. Chem. Rev. 2012, 112, 3193.

1 malassezin

2

Indolo[3,2-b]carbazole (ICZ)

3a 6-formylindolo[3,2-b]carbazole (FICZ)

3b, $R^1 = OH, R^2 = H, R^3 = OH, R^4 = H$
3c, $R^1 = OH, R^2 = R^3 = H, R^4 = OH$
3d, $R^1 = H, R^2 = R^3 = OH, R^4 = H$
3e, $R^1 = R^2 = R^3 = H, R^4 = OH$
3f, $R^1 = OH, R^2 = R^3 = R^4 = H$

Malassezin, ICZ, and FICZ are potent agonists of aryl hydrocarbon receptor (AhR), which is best known for mediating the toxicity of dioxin and related environmental toxins. Denison, M. S.; Soshilov, A. A.; He, G.; Degroot, D. E.; Zhao, B. Toxicol. Sci. 2011, 124, 1. Recent studies showed that AhR also played a critical role in immune cell differentiation, promoting intestinal immune function, and the development of the prostate. See Quintana, F. J.; Basso, A. S.; Iglesias, A. H.; Korn, T.; Farez, M. F.; Bettelli, E.; Caccamo, M.; Oukka, M.; Weiner, H. L. Nature 2008, 453, 65. (b) Stevens, E. A.; Mezrich, J. D.; Bradfield, C. A. Immunology 2009, 127, 299; Li, Y.; Innocentin, S.; Withers, D. R.; Roberts, N. A.; Gallagher, A. R.; Grigorieva, E. F.; Wilhelm, C.; Veldhoen, M. Cell 2011, 147, 629; Kiss, E. A.; Vonarbourg, C.; Kopfmann, S.; Hobeika, E.; Finke, D.;

Esser, C.; Diefenbach, A. Science 2011, 334, 1561; and Mehta, V.; Vezina, C. M. Differentiation 2011, 82, 211, respectively.

It has been demonstrated that selective AhR modulators inhibit prostate tumor metastasis and have anti-asthmatic effects in animal models. Indolo[3,2-b]carbazoles are also important class of organic electroluminescent compounds. See Fritz, W. A.; Lin, T.-M.; Safe, S.; Moore, R. W.; Peterson, R. E. Biochem. Pharmacol. 2009, 77, 1151; Jeong, K.-T.; Hwang, S.-J.; Oh, G.-S.; Park, J.-H. Int. Immunopharmacol. 2012, 13, 377; Gu, R.; Robeyns, K.; Van Meervelt, L.; Toppet, S.; Dehaen, W. Org. Biomol. Chem. 2008, 6, 2484; and Boudreault, P. L. T.; Wakim, S.; Tang, M. L.; Tao, Y.; Bao, Z. A.; Leclerc, M. J. Mater. Chem. 2009, 19, 2921.

Rearrangement of the symmetrical 3,3'-diindolylmethanes to 2,3-diindolylmethanes could be realized using iodine as the catalyst. Gu, R.; Hameurlaine, A.; Dehaen, W. Synlett 2006, 1535. Gu, R.; Hameurlaine, A.; Dehaen, W. J. Org. Chem. 2007, 72, 7207. Low yields, however, were observed when substituted indoles were employed as the substrates. Synthesis of non-symmetric 2,3-diindolylmethanes requires the joining of two different indoles in multiple steps. Tholander, J.; Bergman, J. Tetrahedron Lett. 1998, 39, 1619. Tholander, J.; Bergman, J. Tetrahedron 1999, 55, 6243. Wahlstrom, N.; Stensland, B.; Bergman, J. Synthesis 2004, 1187.

SUMMARY

Disclosed herein is a synthesis of symmetrical or unsymmetrical diindolylmethanes and 1-indolyl-1-pyrrolylmethanes via a platinum-catalyzed indole annulation/arylation cascade reaction. The diindolylmethanes and 1-indolyl-1-pyrrolylmethanes can be further reacted to yield the corresponding indolyl (or indolyl/pyrrolyl) carbazole.

The method comprises contacting an ether comprising an arylpropargyl moiety with a substituted or unsubstituted indol and/or a substituted or unsubstituted pyrrole. When the arylpropargyl ether is contacted with an indole, the resulting product is a diindolylmethane. When the arylpropargyl ether is contacted with a pyrrole, the product is a 1-indolyl-1-pyrrolylmethane. The diindolylmethane or 1-indolyl-1-pyrrolylmethane products can be further reacted to yield the corresponding indolyl (or indolyl/pyrrolyl) carbazoles.

Thus, disclosed herein is a method to make diindolylmethanes and indolyl/pyrrolylmethanes, the method comprising:

contacting an ether comprising an arylpropargyl moiety and an amine-protected, substituted or unsubstituted aniline moiety with a substituted or unsubstituted indol or a substituted or unsubstituted pyrrole, in the presence of a metal-containing catalyst, for a time and at a temperature to cause an annulation/arylation cascade reaction that yields a diindolylmethane or a indolyl/pyrrolylmethane.

The method may comprise performing the reaction depicted in Reaction Scheme 1:

Reaction Scheme 1

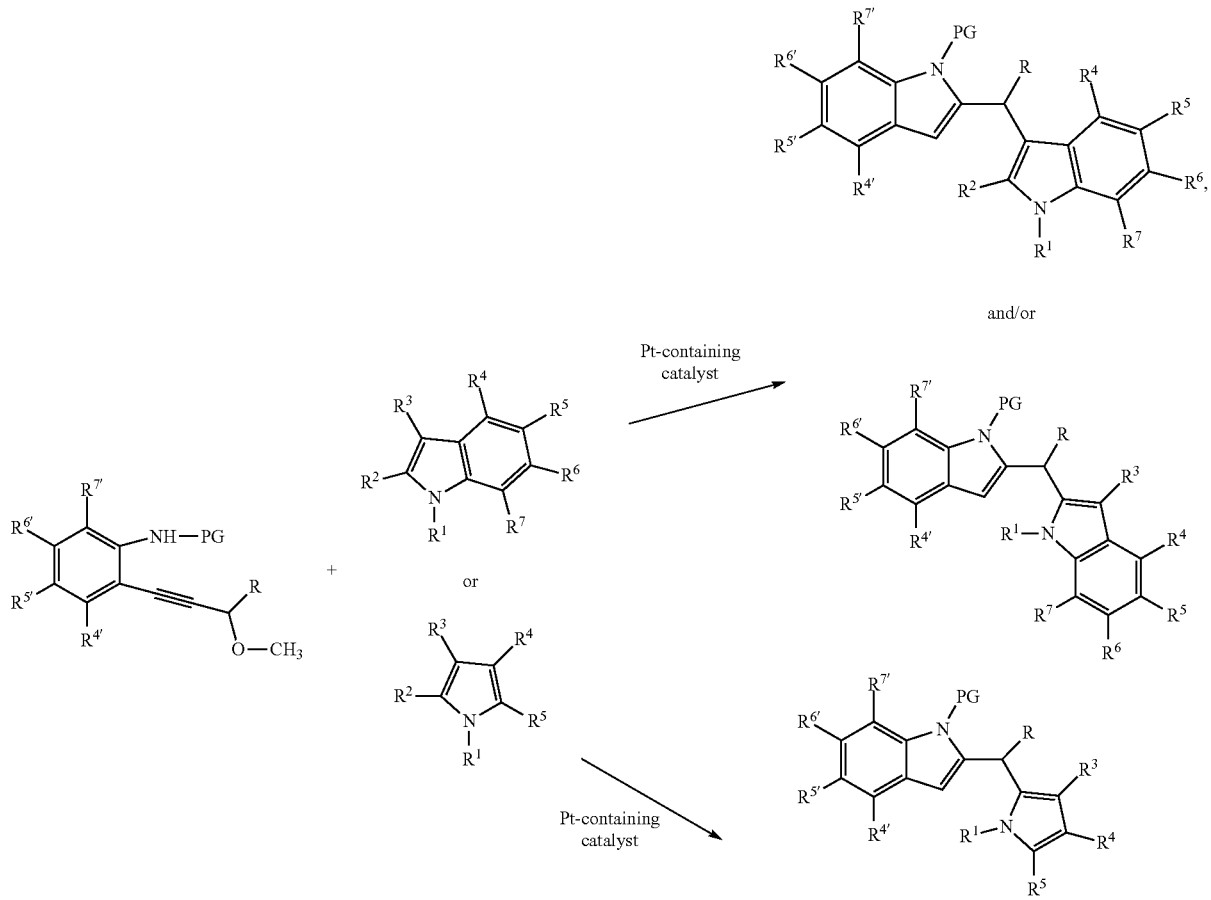

and/or

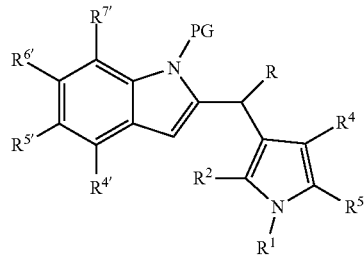

wherein each $R^1$ is independently hydrogen or alkyl;

"PG" designates an amine protecting group; and each R, $R^2$, $R^3$, $R^4$, $R^5$, $R^6$, $R^7$, $R^{4'}$, $R^{5'}$, $R^{6'}$, and $R^{7'}$ is independently selected from hydrogen, halogen, hydroxyl, substituted or unsubstituted alkyl, substituted or unsubstituted alkoxy, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, or substituted or unsubstituted heterocyclylalkyl.

The catalyst may be a catalyst containing a noble metal (ruthenium, rhodium, palladium, silver, osmium, iridium, platinum, and gold), preferably a platinum-containing catalyst or a rhodium-containing catalyst, and most preferably $PtCl_2$.

Also disclosed herein is a pharmaceutical composition comprising an amount of a compound selected from the group consisting of:

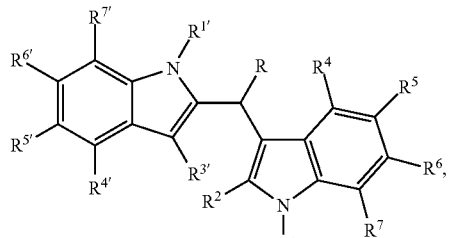

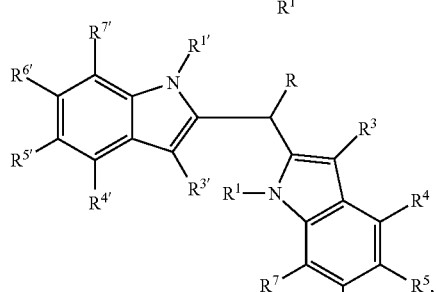

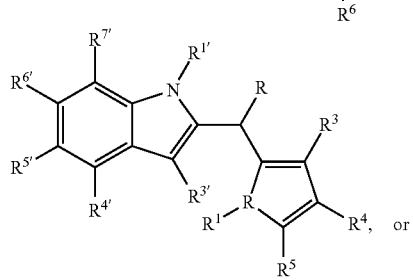

or

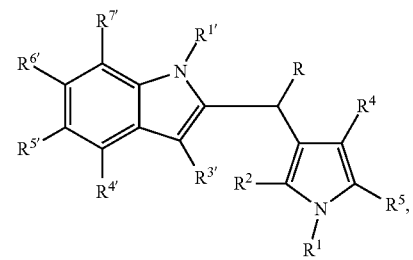

wherein each $R^1$ and $R^{1'}$ is independently hydrogen or alkyl; and each R, $R^2$, $R^3$, $R^4$, $R^5$, $R^6$, $R^7$, $R^{3'}$, $R^{4'}$, $R^{5'}$, $R^{6'}$, and $R^{7'}$ is independently selected from hydrogen, halogen, hydroxyl, substituted or unsubstituted alkyl, substituted or unsubstituted alkoxy, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, or substituted or unsubstituted heterocyclylalkyl;

or a pharmaceutically suitable salt thereof;

in combination with a pharmaceutically suitable carrier;

wherein the amount is effective to modulate activity of arylhydrocarbon receptors in mammals, or the amount is effective to inhibit activity of PCSK9 in mammals, or the amount is effective to stimulate secretion of glucagon-like peptide 1 in mammals.

Further disclosed herein is a method to modulate activity of arylhydrocarbon receptors in mammals, the method comprising administering to the mammal a arylhydrocarbon receptor modulating-effective amount of a compound selected from the group consisting of

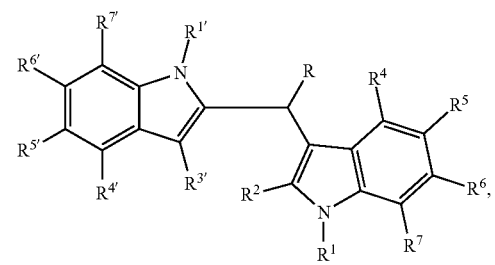

-continued

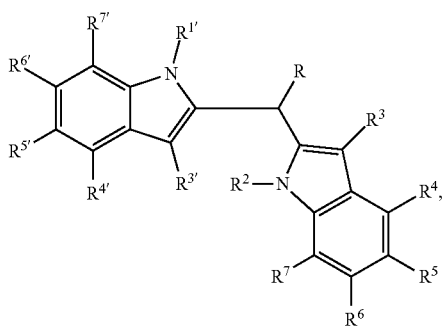

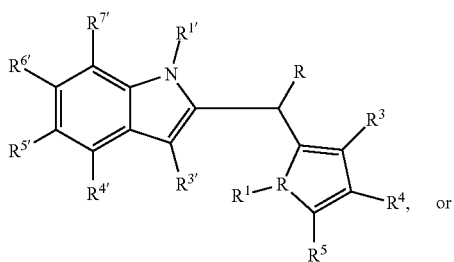

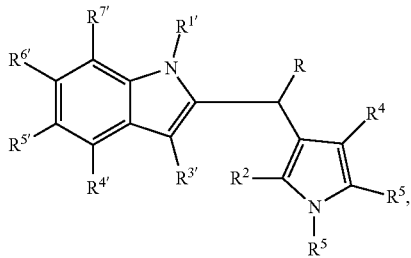

wherein each $R^1$ and $R^{1'}$ is independently hydrogen or alkyl; and each R, $R^2$, $R^3$, $R^4$, $R^5$, $R^6$, $R^7$, $R^{3'}$, $R^{4'}$, $R^{5'}$, $R^{6'}$, and $R^{7'}$ is independently selected from hydrogen, halogen, hydroxyl, substituted or unsubstituted alkyl, substituted or unsubstituted alkoxy, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, or substituted or unsubstituted heterocyclylalkyl;

or a pharmaceutically suitable salt thereof.

Additionally disclosed herein is a method to inhibit activity of proprotein convertase subtilisin/kexin type 9 (PCSK9) in mammals, the method comprising administering to the mammal an PCSK9 inhibitory-effective amount of a compound selected from the group consisting of

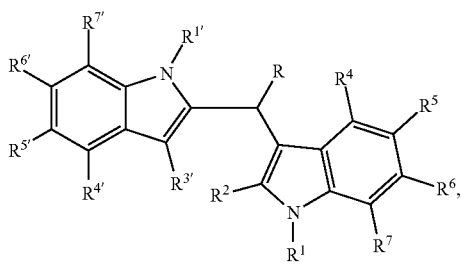

-continued

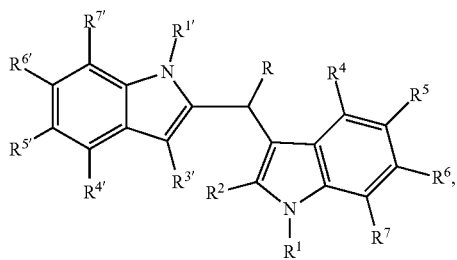

wherein each $R^1$ and $R^{1'}$ is independently hydrogen or alkyl; and each R, $R^2$, $R^3$, $R^4$, $R^5$, $R^6$, $R^7$, $R^{3'}$, $R^{4'}$, $R^{5'}$, $R^{6'}$, and $R^{7'}$ is independently selected from hydrogen, halogen, hydroxyl, substituted or unsubstituted alkyl, substituted or unsubstituted alkoxy, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, or substituted or unsubstituted heterocyclylalkyl;

or a pharmaceutically suitable salt thereof.

Yet further disclosed is a method to stimulate secretion of glucagon-like peptide 1 (GLP-1) in mammals, the method comprising administering to the mammal a GLP-1 secretion-effective amount of a compound selected from the group consisting of

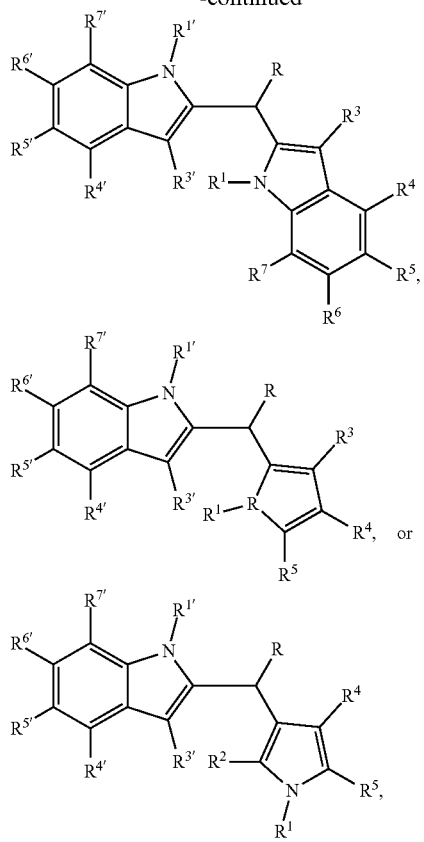

wherein each $R^1$ and $R^{1'}$ is independently hydrogen or alkyl; and each R, $R^2$, $R^3$, $R^4$, $R^5$, $R^6$, $R^7$, $R^{3'}$, $R^{4'}$, $R^{5'}$, $R^{6'}$, and $R^{7'}$ is independently selected from hydrogen, halogen, hydroxyl, substituted or unsubstituted alkyl, substituted or unsubstituted alkoxy, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, or substituted or unsubstituted heterocyclylalkyl;

or a pharmaceutically suitable salt thereof.

Exemplary compounds of the invention include:

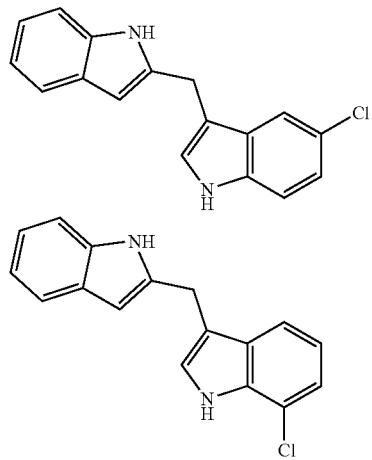

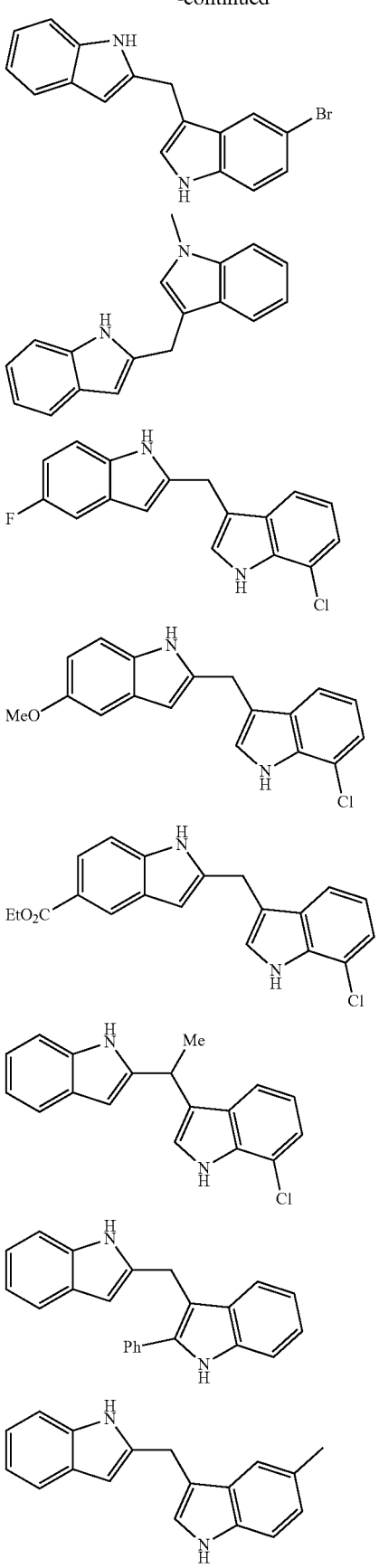

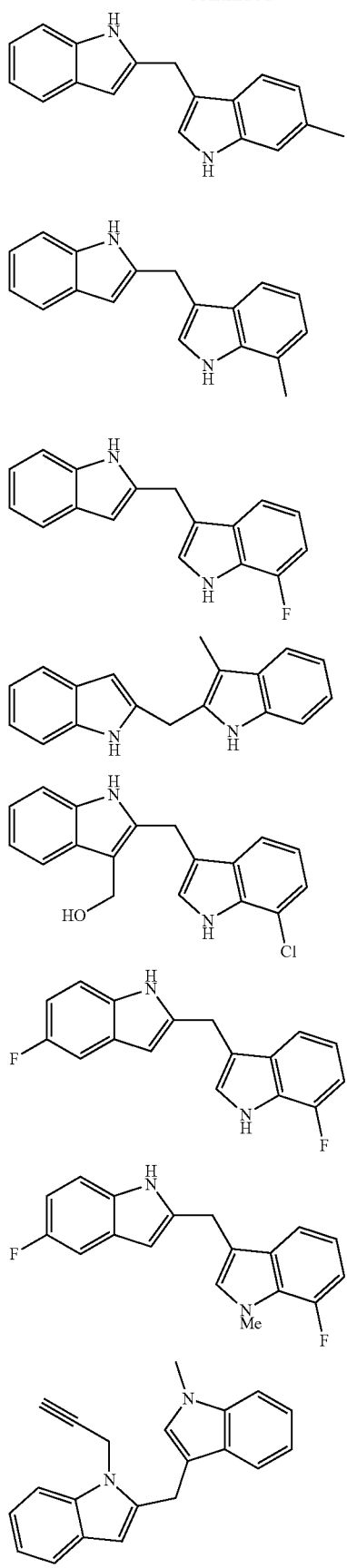
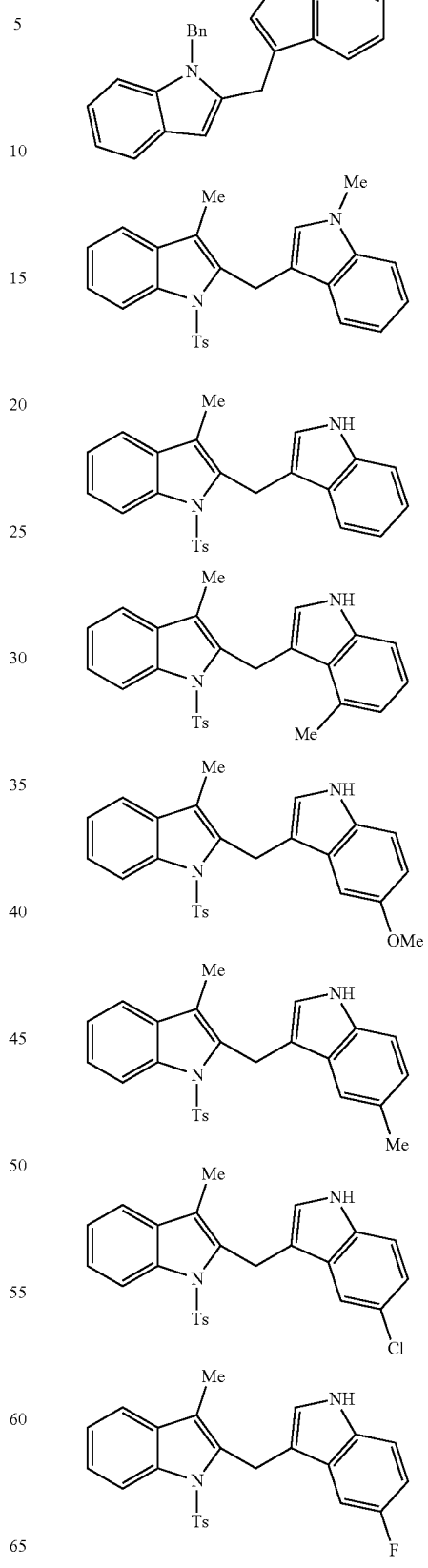

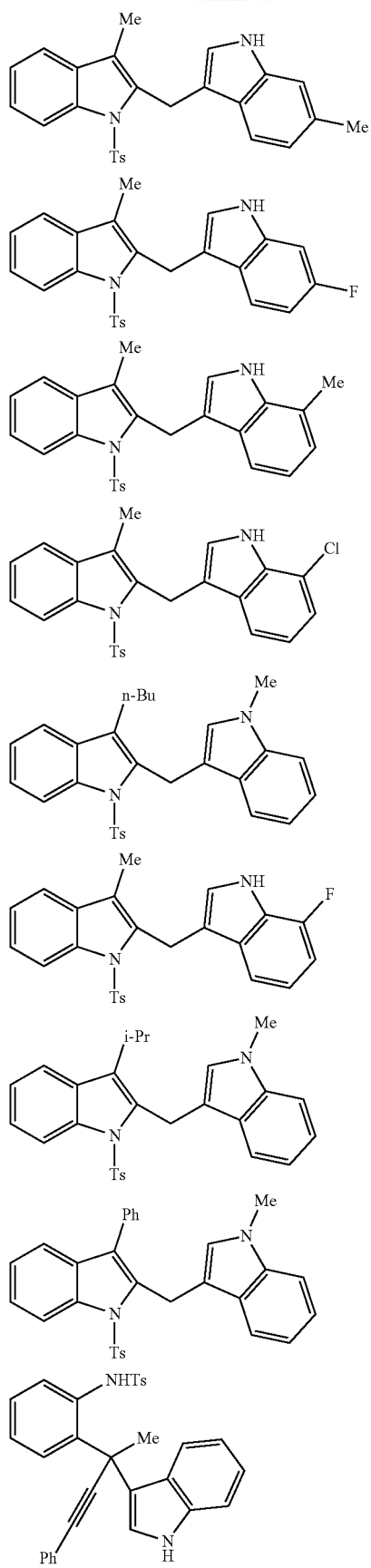
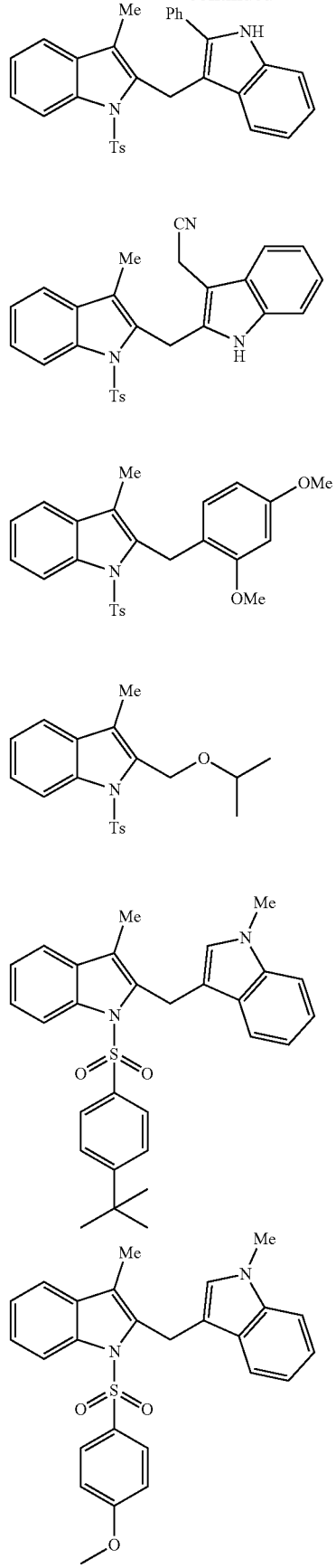

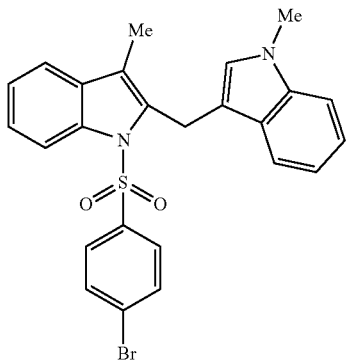
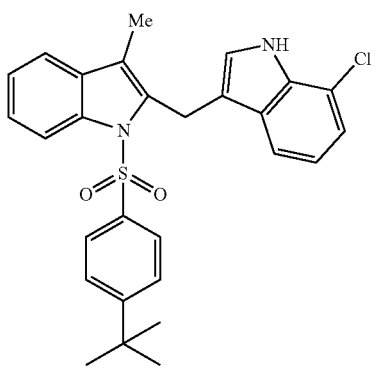
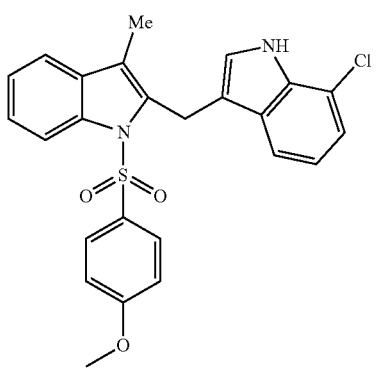
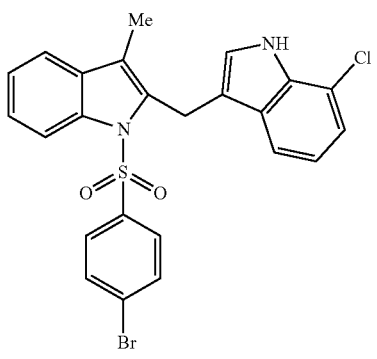
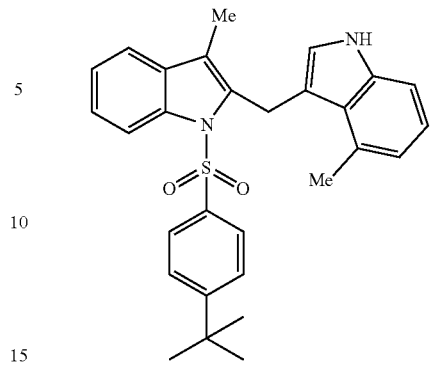
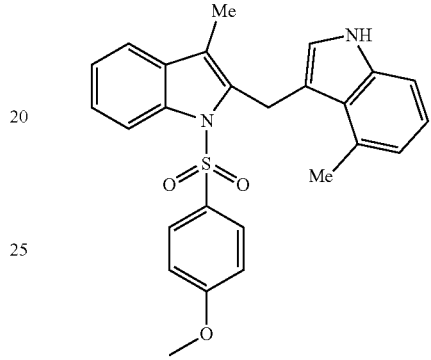
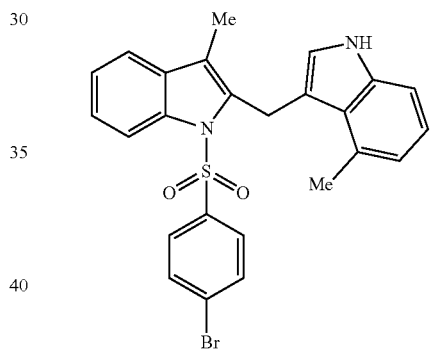
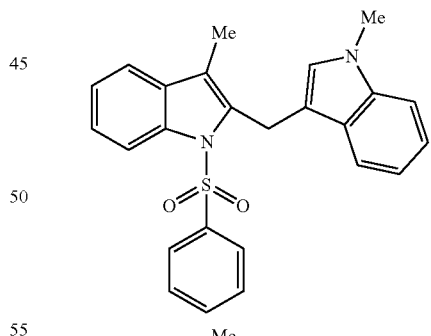
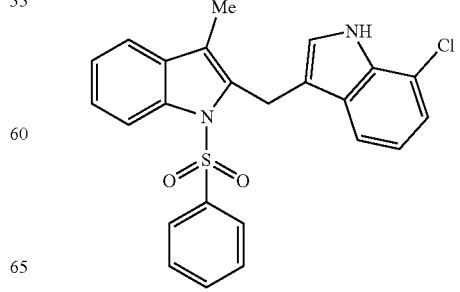

-continued

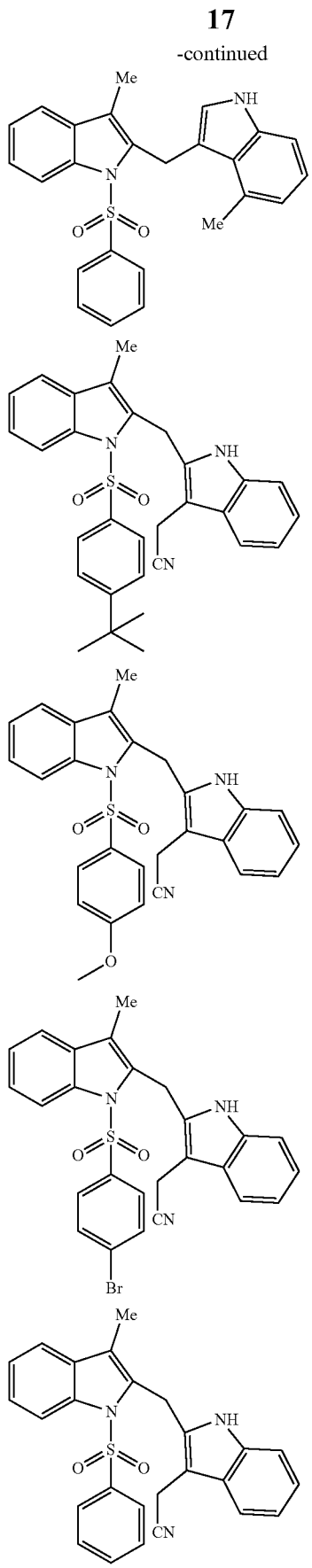

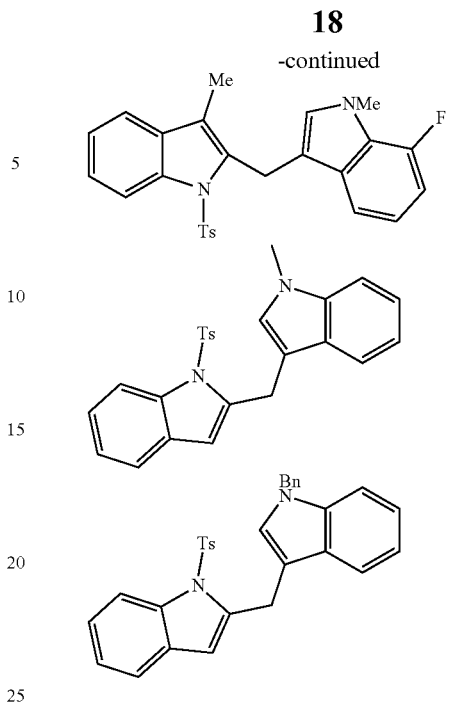

DETAILED DESCRIPTION

Definitions:

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. That is, unless specifically stated to the contrary, "a" and "an" mean "one or more." The phrase "one or more" is readily understood by one of skill in the art, particularly when read in context of its usage. For example, "one or more" substituents on a phenyl ring designates one to five substituents.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry.

The term "contacting" refers to the act of touching, making contact, or of bringing to immediate or close proximity, including at the molecular level, for example, to bring about a chemical reaction, or a physical change, e.g., in a solution or in a reaction mixture.

An "effective amount" refers to an amount of a chemical or reagent effective to facilitate a chemical reaction between two or more reaction components, and/or to bring about a recited effect. Thus, an "effective amount" generally means an amount that provides the desired effect.

The term "solvent" refers to any liquid that can dissolve a compound to form a solution. Solvents include water and various organic solvents, such as hydrocarbon solvents, for example, alkanes and aryl solvents, as well as halo-alkane solvents. Examples include hexanes, benzene, toluene, xylenes, chloroform, methylene chloride, dichloroethane, and alcoholic solvents such as methanol, ethanol, propanol, isopropanol, and linear or branched (sec or tert) butanol, and the like. Aprotic solvents that can be used in the method include, but are not limited to, perfluorohexane, $\alpha,\alpha,\alpha$-trifluorotoluene, pentane, hexane, cyclohexane, methylcyclohexane, decalin, dioxane, carbon tetrachloride, freon-11, benzene, toluene, triethyl amine, carbon disulfide, diisopropyl ether, diethyl ether, t-butyl methyl ether (MTBE), chloroform, ethyl acetate, 1,2-dimethoxyethane (glyme), 2-methoxyethyl ether (diglyme), tetrahydrofuran (THF), methylene chloride, pyridine, 2-butanone (MEK), acetone, hexamethylphosphoramide, N-methylpyrrolidinone (NMP), nitromethane, dimethylformamide (DMF), acetonitrile, sulfolane, dimethyl sulfoxide (DMSO), propylene carbonate, and the like.

The term "alkyl" refers to a branched or unbranched carbon chain having, for example, about 1-20 carbon atoms, and often 1-12, 1-10, 1-8, 1-6, or 1-4 carbons. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated in certain embodiments. As such, the recitation of an alkyl group optionally includes both alkenyl and alkynyl groups. The alkyl can be a monovalent hydrocarbon radical, as described and exemplified above, or it can be a divalent hydrocarbon radical (i.e., an alkylene). In some embodiments, certain alkyl groups can be excluded from a definition. For example, in some embodiments, methyl, ethyl, propyl, butyl, or a combination thereof, can be excluded from a specific definition of alkyl in an embodiment.

The term "cycloalkyl" refers to cyclic alkyl groups of, for example, 3 to about 12, 3 to about 10, 3 to about 8, about 4 to about 8, or 5-6, carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

As used herein, "aryl" refers to an aromatic hydrocarbon group derived from the removal of one hydrogen atom from a single carbon atom of a parent aromatic ring system. The radical attachment site can be at a saturated or unsaturated carbon atom of the parent ring system. The aryl group can have from 6 to about 20 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "heteroaryl" refers to a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described in the definition of "substituted". Typical heteroaryl groups contain 2-20 carbon atoms in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or —(C1-C6)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, silicon, and sulfur, and optionally substituted with one or more groups as defined for the term "substituted". A heterocycle can be a monocyclic, bicyclic, or tricyclic group. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholinyl, piperazinyl, piperidinyl, pyrazolidinyl, pyrazolinyl, pyrrolidine, pyrroline, quinuclidine, tetrahydrofuranyl, and thiomorpholine, where the point of attachment can be at any atom accessible by known synthetic methods.

The term "substituted" indicates that one or more hydrogen atoms on the group indicated in the expression using "substituted" is replaced with a "substituent". The number referred to by 'one or more' can be apparent from the moiety one which the substituents reside. For example, one or more can refer to, e.g., 1, 2, 3, 4, 5, or 6; in some embodiments 1, 2, or 3; and in other embodiments 1 or 2. The substituent can be one of a selection of indicated groups, or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano. Additionally, suitable substituent groups can be, e.g., —X, —R, —O—, —OR, —SR, —S—, —NR$_2$, —NR$_3$, =NR, —CX$_3$, —CN, —OCN, —SCN, —N=C=O, —NCS, —NO, —NO2, =N$_2$, —N$_3$, —NC(=O)R, —C(=O)R, —C(=O)NRR, —S(=O)$_2$O—, —S(=O)$_2$OH, —S(=O)$_2$R, —OS(=O)$_2$OR, —S(=O)$_2$NR, —S(=O)R, —OP(=O)O$_2$RR, —P(=O)O$_2$RR, —P(=O)(O—)$_2$, —P(=O)(OH)$_2$, —C(=O)R, —C(=O)X, —C(S)R, —C(O)OR, —C(O)O—, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

A protecting group is any chemical moiety capable of selective addition to and removal from a reactive site to allow manipulation of a chemical entity at sites other than the reactive site. Many protecting groups are known in the art. A large number of protecting groups and corresponding chemical cleavage reactions are described in "Protective Groups in Organic Synthesis," Theodora W. Greene (John Wiley & Sons, Inc., New York, 1991, ISBN 0-471-62301-6) ("Greene", which is incorporated herein by reference). See also the 5$^{th}$ edition of this same work, published under the title "Greene's Protective Groups in Organic Synthesis," ISBN-13: 978-1118057483, ©2014, John Wiley & Sons, Inc. Greene describes many nitrogen protecting groups, for example, amide-forming groups. In particular, see Chapter 1, Protecting Groups: An Overview, Chapter 2, Hydroxyl Protecting Groups, Chapter 4, Carboxyl Protecting Groups, and Chapter 5, Carbonyl Protecting Groups. For additional information on protecting groups, see also Kocienski, Philip J. "Protecting Groups," (Georg Thieme Verlag Stuttgart, New York, 1994), which is incorporated herein by reference. Typical nitrogen protecting groups described in Greene include benzyl ethers, silyl ethers, esters including sulfonic acid esters, carbonates, sulfates, and sulfonates. For example, suitable nitrogen protecting groups include substituted methyl ethers; substituted ethyl ethers; p-chlorophenyl, p-methoxyphenyl, 2,4-dinitrophenyl, benzyl; substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, diphenylmethyl, 5-dibenzosuberyl, triphenylmethyl, p-methoxyphenyl-diphenylmethyl, di(p-methoxyphenyl)phenylmethyl, tri(p-methoxyphenyl)methyl, 1,3-benzodithiolan-2-yl, benzisothiazolyl S,S-dioxido); silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxy-phenylsilyl); esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), pivaloate, adamantoate, crotonate, 4-methoxycrotonate, benzoate, p-phenylbenzoate, 2,4,6-trimethylbenzoate(mesitoate)); carbonates (methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate); groups with assisted cleavage (2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, miscellaneous esters (2,6-dichloro-4-methylphenoxyacetate, 2,6-dichloro-4-(1,1,3,3 tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate (tigloate), o-(methoxycarbonyl)benzoate, p-poly-benzoate, α-naphthoate, nitrate, alkyl N,N,N',N'-tetramethyl-phosphorodiamidate, n-phenylcarbamate, borate, 2,4-dinitrophenylsulfenate); or sulfonates (methanesulfonate(mesylate), benzenesulfonate, benzylsulfonate, tosylate, or triflate).

The more common of the amine-protecting groups have trivial abbreviations that are widely used in the literature and include: carbobenzyloxy (Cbz) group (removed by hydrogenolysis), p-methoxybenzyl carbonyl (Moz or MeOZ) group (removed by hydrogenolysis), tert-butyloxycarbonyl (BOC) group (common in solid phase peptide synthesis; removed by concentrated strong acid (such as HCl or CF$_3$COOH), or by heating to >80° C., 9-fluorenylmethyloxycarbonyl (FMOC) group (also common in solid phase peptide synthesis; removed by base, such as piperidine), acetyl (Ac) group (removed by treatment with a base), benzoyl (Bz) group (removed by treatment with a base), benzyl (Bn) group (removed by hydrogenolysis), carbamate group (removed by acid and mild heating), p-methoxybenzyl (PMB) (removed by hydrogenolysis), 3,4-dimethoxybenzyl (DMPM) (removed by hydrogenolysis), p-methoxyphenyl (PMP) group (removed by ammonium cerium(IV) nitrate (CAN)), tosyl (Ts) group (removed by concentrated acid and strong reducing agents), sulfonamide groups (Nosyl & Nps; removed by samarium iodide, tributyltin hydride.

A "pharmaceutically-suitable salt" is any acid or base addition salt whose counter-ions are non toxic to a patient (including a veterinary patient) in pharmaceutical doses of the salts, so that the beneficial pharmacological effects inherent in the free base or free acid are not vitiated by side effects ascribable to the counter-ions. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene bis-b-hydroxynaphthoates, gentisates, isethionates, di-p-toluoyltartrates, methane sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N methylmorpholine, and the like.

The Method:

The synthetic approach is most easily disclosed by way of an example. The example is for brevity and ease of explanation only. It does not limit the scope of the method disclosed and claimed herein in any fashion. Referring specifically to Table 1, a metal carbene intermediate was generated from annulation of propargylic ether 4 and trapped previously by a diene in a (4+3) cycloaddition. Shu, D.; Song, W.; Li, X.; Tang, W. Angew. Chem. Int. Ed., 2013, 52, 3237. The present inventors envisioned that this metal carbene intermediate could also be trapped by other nucleophiles. Thus, it was thought that in the presence of another indole, diindolylmethanes could then be prepared conveniently.

As shown in Table 1, both Pt- and Rh-complexes promoted the formation of the 2,3'-diindolylmethane product 6a, though the former provided a higher yield. A slightly lower yield was obtained with lower catalyst loading (entry 3; 5 mol % catalyst vs. 10 mol %). In the case of indole annulation/arylation to form diindolylmethanes, using PtCl$_2$ alone as the catalyst appeared to be sufficient (entry 4). The yield again became slightly lower if the amount of catalyst was lowered to 5 mol % (entry 5). Other metal complexes did not produce any desired product (entries 6-10).

The scope of different indoles was examined for this tandem indole annulation/arylation cascade using propargylic ether 4 as the starting material (Table 2). N-Methyl indole 5b afforded a high yield of the 2,3'-diindolyl methane product 6b. The yield became 20% lower for 4-Br substituted N-methylindole 5c. Interestingly, the 4-cyano substituted indole 5d did not interfere with the efficiency of the tandem reaction. The indole annulation/arylation reaction could also tolerate electron-donating methoxy or halogen substituents on the 5- or 6-position of the indole (e.g. 5e, 5f, 5g, and 5h). The effect of substituent on the 2- and 3-position of indole 5 was then studied. With a 2-phenyl substituent on indole 5i, the yield of product 6i is comparable to 6a. When the intrinsically more reactive 3-position of the indole is blocked as in substrate 5j, a 2,2'-diindolylmethane was obtained in 60% yield.

Various substitutions on aniline and propargylic ether reactants was also investigated (Table 3). Substitutions at the para-position of the aniline were studied to examine how the change of pKa of the aniline influenced the efficiency of the reaction. It was found that anilines with either an electron-donating methoxy group or an electron-withdrawing ester group at the para-position participated most effectively in the tandem reaction. Aniline 7a with an electron-donating para methoxy group provided a higher yield of the desired product than the one with a para electron-withdrawing group (7b). A moderate 55% yield was observed when aniline 7c with a free hydroxyl group was employed as the substrate. Secondary propargylic ether 7d also participated in the tandem reaction and afforded diindolylethane 8d.

TABLE 1

Screening of Catalysts and Conditions[a]

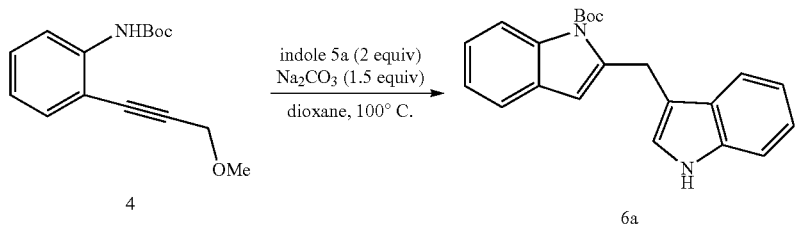 [SMILES: COCC#Cc1ccccc1NC(=O)OC(C)(C)C ; CC(C)(C)OC(=O)n1c(Cc2c[nH]c3ccccc23)cc2ccccc21]

| entry | Conditions | yield (%) |
|---|---|---|
| 1 | PtCl$_2$ (10 mol %), P(C$_6$F$_5$)$_3$(20 mol %) | 84 |
| 2 | [Rh(CO)$_2$Cl]$_2$(10 mol %), P[OCH(CF$_3$)$_2$]$_3$ (20 mol %) | 56 |
| 3 | PtCl$_2$ (5 mol %), P(C$_6$F$_5$)$_3$(10 mol %) | 77 |
| 4 | PtCl$_2$ (10 mol %) | 83[b] |
| 5 | PtCl$_2$ (5 mol %) | 76 |
| 6 | AgBF$_4$ (10 mol %) | 0 |
| 7 | AgOTf (10 mol %) | 0 |
| 8 | CuOTf (10 mol %) | 0 |
| 9 | AgOTf (10 mol %), P(C$_6$F$_5$)$_3$(20 mol %) | 0 |
| 10 | CuOTf (10 mol %), P(C$_6$F$_5$)$_3$(20 mol %) | 0 |

[a]Unless noted otherwise, the yield of 6a was determined by $^1$H NMR of crude product.
[b]Isolated yield.

TABLE 2

Scope of Indoles for Pt-Catalyzed Tandem Indole Annulation/Arylation of Propargylic Ether 4[a]

| indole substrates | products | yield (%)[b] |
|---|---|---|
| 5a | 6a | 83 |
| 5b | 6b | 88 |
| 5c | 6c | 68 |
| 5d | 6d | 81 |
| 5e | 6e | 77 |
| 5f | 6f | 84 |
| 5g | 6g | 85 |

TABLE 2-continued

Scope of Indoles for Pt-Catalyzed Tandem Indole Annulation/Arylation of Propargylic Ether 4[a]

| indole substrates | products | yield (%)[b] |
|---|---|---|
| 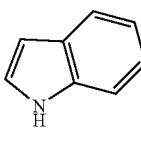<br>5h | 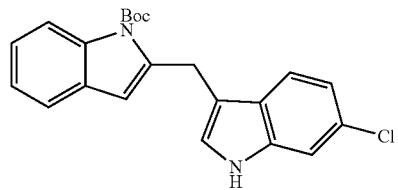 [SMILES: CC(C)(C)OC(=O)n1c(Cc2c[nH]c3cc(Cl)ccc23)cc2ccccc21]<br>6h | 82 |
| 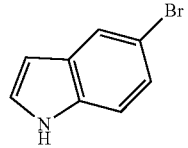<br>5i | 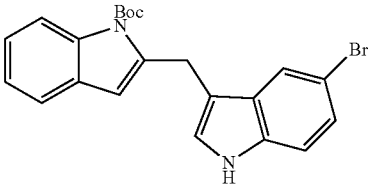 [SMILES: CC(C)(C)OC(=O)n1c(Cc2c[nH]c3ccc(Br)cc23)cc2ccccc21]<br>6i | 80 |
| 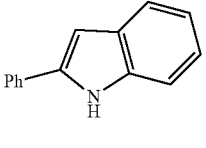 [SMILES: c1ccc(-c2cc3ccccc3[nH]2)cc1]<br>5j | 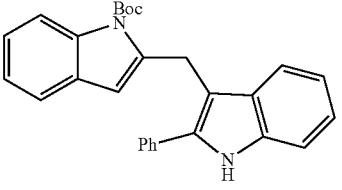 [SMILES: CC(C)(C)OC(=O)n1c(Cc2c(-c3ccccc3)[nH]c3ccccc23)cc2ccccc21]<br>6j | 60 |
| 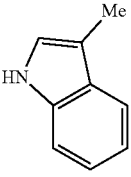 | 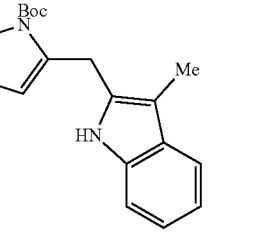 | |

[a]Conditions: 4 (1 equiv), indole 5 (2 equiv), PtCl₂ (10 mol %), Na₂CO₃ (1.5 equiv), 100° C., dioxane.
[b]Isolated yield.

Table 3 shows that the method will also work wen the propargylic ether is substituted at various positions on the aniline ring, as well as on the other side of the triple bond.

TABLE 3

Scope of Aniline and Propargylic Ether for Pt-Catalyzed Tandem Indole Annulation/Arylation[a]

| indole substrates | products | yield[b] |
|---|---|---|
| 7a<br>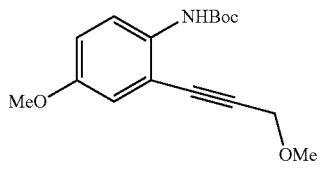 | 8a<br>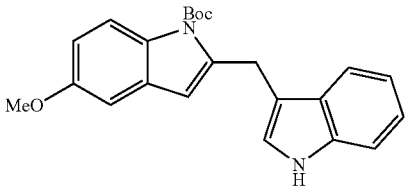 | 77% |

TABLE 3-continued

Scope of Aniline and Propargylic Ether for Pt-Catalyzed Tandem Indole Annulation/Arylation[a]

| indole substrates | products | yield[b] |
|---|---|---|
| 7b | 8b | 62% |
| 7c | 8c | 55% |
| 7d | 8d | 70% |

[a]See Table 1 for conditions.
[b]Isolated yield.

Other nucleophiles beyond indoles will also function in the method. For example, substituted and unsubstituted pyrroles will also function in the method. N-methylpyrrole, for example, was used as the nucleophile and product 9 was isolated in 68% yield.

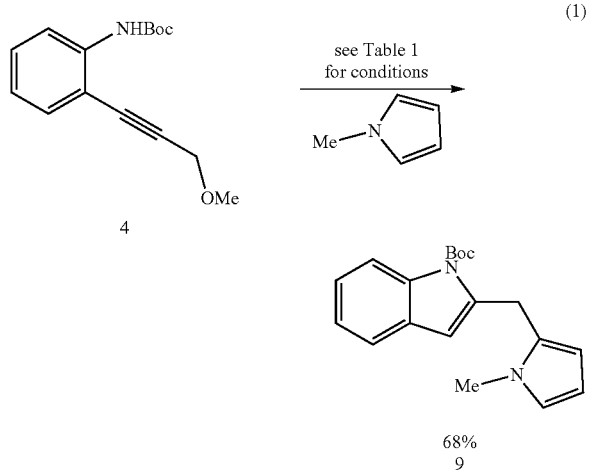

(1)

To demonstrate the utility of the Pt-catalyzed indole annulation/arylation method, it was used in the synthesis of the natural product malassezin and a formal synthesis of natural product FICZ as shown in Reaction Scheme 2. Removal of the Boc-protecting group in product 6a under thermal conditions yielded diindolylmethane 10, which could undergo formylation to afford malassezin 1. Wille, G.; Mayser, P.; Thoma, W.; Monsees, T.; Baumgart, A.; Schmitz, H. J.; Schrenk, D.; Polborn, K.; Steglich, W. Bioorg. Med. Chem. 2001, 9, 955. Acylation of diindolylmethane 10 followed by acid-mediated cyclization produced indolo[3,2-b]carbazole 11, which has been converted to natural product FICZ 3a through a known sequence of reduction and oxidation. Wahlstrom, N.; Romero, I.; Bergman, J. Eur. J. Org. Chem. 2004, 2593. The spectroscopic data of compounds 1, 10 and 11 are all in accordance with literature (data not shown). The structure of 2,3'-diindolylmethane 6a was then further confirmed.

The proposed mechanism for the indole annulation/arylation is shown in Scheme 3. After the coordination of the metal catalyst to propargylic ether 4,5-endo-cyclization of metal complex 12 will lead to the formation of indole intermediate 13. Elimination of a methanol can then produce metal carbene intermediate 14, which has been proposed previously by and others. Saito, K.; Sogou, H.; Suga, T.; Kusama, H.; Iwasawa, N. J. Am. Chem. Soc. 2011, 133, 689. Allegretti, P. A.; Ferreira, E. M. Org. Lett. 2011, 13, 5924. (c) Allegretti, P. A.; Ferreira, E. M. Chem. Sci. 2013, 4, 1053. This electrophilic metal carbene is then captured by an indole nucleophile to form adduct 15. Protonation and re-aromatization can then lead to final diindolylmethane product 5a. A (3+2) cycloaddition between metal carbene 14 and vinyl ethers has been reported. Saito, K.; Sogou, H.; Suga, T.; Kusama, H.; Iwasawa, N. J. Am. Chem. Soc. 2011, 133, 689. In the examples described herein, no (3+2) cycloaddition product between metal carbene 14 and indole was observed.

Reaction Scheme 2. Synthesis of Malassezin and FICZ

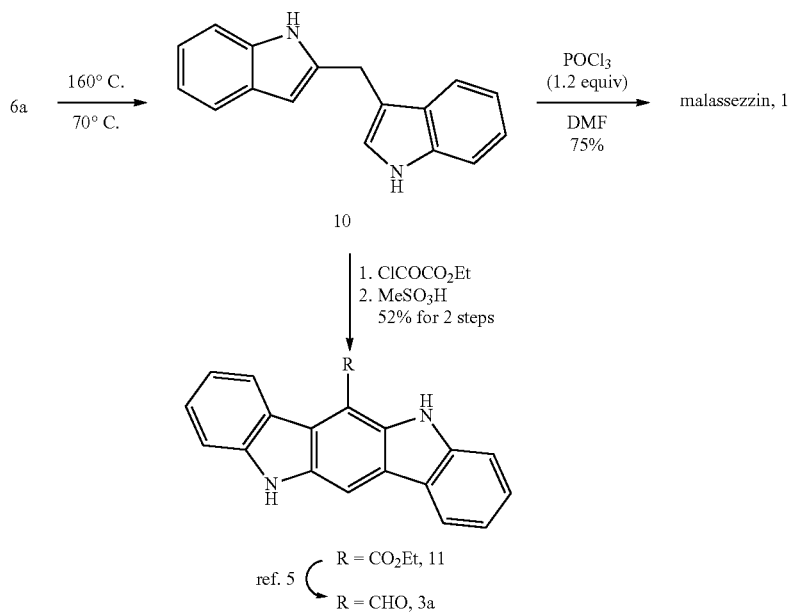

Reaction Scheme 3. Proposed Mechanism

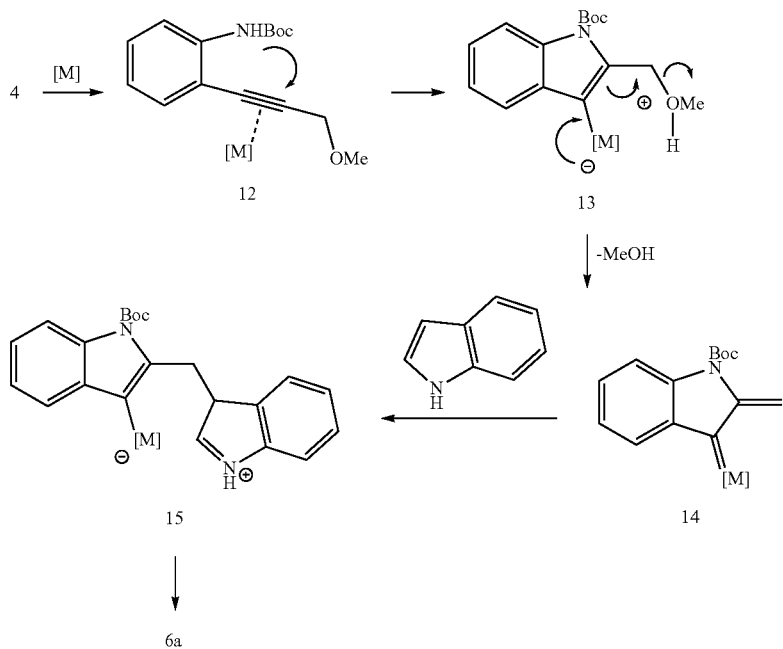

Thus, disclosed herein is an efficient method for the synthesis of various highly substituted 2,3'-diindolylmethanes and other compounds. The indole annulation event is accompanied by the coupling of two indole units. An electrophilic platinum carbene intermediate was proposed to be involved in this cascade reaction. It has been shown that the method can be applied to the synthesis of natural products malassezin and indolo[3,2-b]carbazoles.

Nutritional and Pharmaceutical Compositions, Method to Treat Disease States Mediated by the Arylhydrocarbon Receptor (AhR), Including Prostate Cancer:

The present disclosure includes nutritional compositions. Such compositions include any food or preparation for human consumption (including for enteral or parenteral consumption) which when taken into the body (a) serve to nourish or build up tissues or supply energy and/or (b) maintain, restore or support adequate nutritional status or metabolic function.

The nutritional composition comprises at least one compound as described herein and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany hyperglycemic metabolic conditions.

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed search. Additionally, examples of proteins which may be utilized in the nutritional composition include but are not limited to soy proteins, electrodialysed whey, electrodialysed skim milk, milk whey, or the hydrolysates of these proteins.

With respect to vitamins and minerals, the following may be added to the nutritional compositions described herein: calcium, phosphorus, potassium, sodium, chloride, magnesium, manganese, iron, copper, zinc, selenium, iodine, and Vitamins A, E, D, C, and the B complex. Other such vitamins and minerals may also be added.

Examples of nutritional compositions disclosed herein include but are not limited to infant formulas, dietary supplements, dietary substitutes, and rehydration compositions. Nutritional compositions of particular interest include but are not limited to those utilized for enteral and parenteral supplementation for infants, specialist infant formulas, supplements for the elderly, and supplements for those with hyperglycemia.

The nutritional composition of the present invention may also be added to food even when supplementation of the diet is not required. For example, the composition may be added to food of any type including but not limited to margarines, modified butters, cheeses, milk, yoghurt, chocolate, candy, snacks, salad oils, cooking oils, cooking fats, meats, fish and beverages.

In a preferred version, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to GLP-1 analogs described herein, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art. An enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutritional formulas are well known in the art and are commercially available (e.g., Similac®-brand and Ensure®-brand formulas from Ross Products Division, Abbott Laboratories, Columbus, Ohio). A GLP-1 analog produced in accordance with the present disclosure may be added to commercial formulas of this type.

The energy density of the nutritional compositions in liquid form may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

Also disclosed herein are pharmaceutical compositions comprising one or more of the compounds or a pharmaceutically suitable salt thereof as described herein. The pharmaceutical compositions are useful to treat disease states mediated by the arylhydrocarbon receptor (AhR). More specifically, the pharmaceutical composition may comprise one or more of the compounds disclosed herein as well as a standard, well-known, non-toxic pharmaceutically suitable carrier, adjuvant or vehicle such as, for example, phosphate-buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, injectible, suppository, or topical ointment or cream. Proper fluidity can be maintained, for example, by maintaining appropriate particle size in the case of dispersions and by the use of surfactants. It may also be desirable to include isotonic agents, for example, sugars, sodium chloride, and the like. Besides such inert diluents, the composition may also include adjuvants, such as wetting agents, emulsifying and suspending agents, sweetening agents, flavoring agents, perfuming agents, and the like.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art of pharmacy. For example, one or more compounds produced as described herein can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant active ingredient(s) as described herein.

For intravenous administration, the compounds may be incorporated into commercial formulations such as Intralipid©-brand fat emulsions for intravenous injection. ("Intralipid" is a registered trademark of Fresenius Kabi AB, Uppsalla, Sweden.) Where desired, the individual components of the formulations may be provided individually, in kit form, for single or multiple use. A typical intravenous dosage of a representative compound as described herein is from about 0.1 mg to 100 mg daily and is preferably from 0.5 mg to 3.0 mg daily. Dosages above and below these stated ranges are specifically within the scope of the claims.

Possible routes of administration of the pharmaceutical compositions include, for example, enteral (e.g., oral and rectal) and parenteral. For example, a liquid preparation may be administered, for example, orally or rectally. Additionally, a homogenous mixture can be completely dispersed in water (or other suitable vehicle), admixed under sterile conditions with physiologically acceptable diluents, preservatives, buffers or propellants in order to form a spray or inhalant. The route of administration will, of course, depend upon the desired effect and the medical state of the subject being treated. The dosage of the composition to be administered to the patient may be determined by one of ordinary skill in the art and depends upon various factors such as weight of the patient, age of the patient, immune status of the patient, etc., and is ultimately at the discretion of the medical professional administering the treatment.

With respect to form, the composition may be, for example, a solution, a dispersion, a suspension, an emulsion, or a sterile powder which is then reconstituted. The composition may be administered in a single daily dose or multiple doses.

The present disclosure also includes treating neoplastic disorders in mammals, including humans, by administering an anti-neoplastic-effective amount of one or more the compounds described herein. In particular, the compositions of the present invention may be used to treat neoplasms of any and all description, but most specifically those that involve a signaling pathway mediated by AhR, and most specifically prostate cancer. Additionally, the compositions of the present invention may also be used to prevent the apoptotic death of cells in the prostate.

It should be noted that the above-described pharmaceutical and nutritional compositions may be utilized in connection with non-human animals, both domestic and non-domestic, as well as humans.

EXAMPLES

The following examples are included solely to provide a more complete disclosure of the methods, compounds, and compositions described herein. The examples are not intended to limit the scope of the disclosure or the attached claims 1. General Remarks:

All reactions in non-aqueous media were conducted under a positive pressure of dry argon in glassware that had been oven dried prior to use unless noted otherwise. Anhydrous solutions were transferred via an oven dried syringe or cannula. All solvents were dried prior to use unless noted otherwise. Thin layer chromatography was performed using precoated silica gel plates (EMD Chemicals Inc., Gibbstown, N.J., USA, catalog no. 60, F254). Flash column chromatography was performed with silica gel (SiliCycle, Inc., Quebec City (Quebec), Canada; 40-63 µm). Infrared spectra (IR) were obtained on a Bruker Equinox 55 Spectrophotometer (Bruker AXS, Inc., Madison, Wis., USA). $^1$H and $^{13}$C nuclear magnetic resonance spectra (NMR) were obtained on a Varian Unity-Inova (Varian Instruments, a division of Agilent Technologies, Inc., Santa Clara, Calif., USA) 400 MHz or 500 MHz recorded in ppm (δ) downfield of TMS (δ=0) in CDCl$_3$ unless noted otherwise. Signal splitting patterns were described as singlet (s), doublet (d), triplet(t), quartet (q), quintet (quint), or multiplet (m), with coupling constants (J) in hertz. High resolution mass spectra (HRMS) were performed by Analytical Instrument Center at the School of Pharmacy on an Electron Spray Injection (ESI) mass spectrometer. The optical rotation was determined using a Perkin-Elmer 241 Polarimeter (PerkinElmer, Inc. Waltham, Mass., USA).

2. Experimental Procedure for the Preparation of Propargylic Alcohol Substrates:

Preparation of Substrates 7 and 11a-11c:

(2.1) Ketones S2 and S3 were prepared from S1.

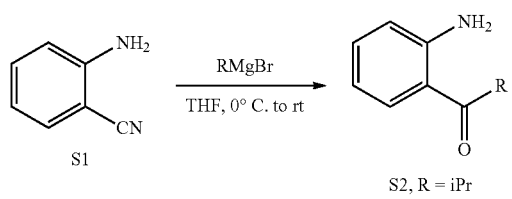

S2, R = iPr
S3, R = nBu

To a solution of 2-aminobenzonitrile S1 (0.50 g, 4.2 mmol) in THF (4 mL) was added isopropylmagnesium bromide (16.8 mL, 0.5 M in THF, 8.4 mmol) at 0° C. over 5 min. The reaction was then allowed to warm to ambient temperature and stir at this temperature for 1 h. The reaction was quenched by slow addition of 1 M HCl. The mixture was extracted by EtOAc. The combined organic layers was washed with NaHCO$_3$ and brine, dried over Na$_2$SO$_4$, and concentrated under vacuum. The residue was purified by flash column chromatography (10-30% EtOAc in hexanes) to give S2 (0.60 g, 88%) as colorless oil. Zhang, J.; Zhu, D.; Yu, C.; Wan, C.; Wang, Z., Org. Lett. 2010, 12, 2841. Gabriele, B.; Mancuso, R.; Lupinacci, E.; Spina, R.; Salerno, G.; Veltri, L.; Dibenedetto, A. Tetrahedron 2009, 65, 8507. Clavier, H.; Lepronier, A.; Bengobesse-Mintsa, N.; Gatineau, D.; Pellissier, H.; Giordano, L.; Tenaglia, A.; Buono, G. Adv. Synth. Catal. 2013, 355, 403. Kothandaraman, P.; Lauw, S. J. L.; Chan, P. W. H. Tetrahedron, 2013, 69, 7471.

Following the same procedure, S3 was prepare from S1 in 44.3 mmol scale (4.61 g, 59%) as colorless oil.

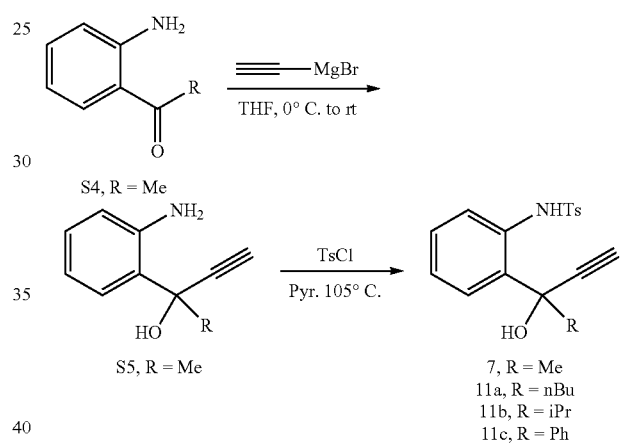

S4, R = Me

S5, R = Me

7, R = Me
11a, R = nBu
11b, R = iPr
11c, R = Ph

Commercially available 1-(2-aminophenyl)ethanone S4 (2.12 g, 15.7 mmol) was dissolved in dry THF (100 mL). To the above solution was added ethynylmagnesium bromide (157 mL, 0.5 M in THF, 78.5 mmol) at 0° C. over 30 min with stirring. After additional stirring at 0° C. for 15 min, the mixture was allowed to warm up to room temperature, and stirred over night. The reaction was quenched by saturated aqueous NH$_4$Cl. The mixture was extracted with EtOAc and the combined organic layers were washed with brine and dried over Na$_2$SO$_4$. The solvent was removed under vacuum and the crude product S5 was directly used for the next step.

To a solution of crude S5 was added tosyl chloride (1.05 equiv) in pyridine (0.8 M) and the resulting solution was stirred at 105° C. for 30 min under argon. The reaction mixture was cooled to room temperature and diluted with EtOAc. The mixture was washed with 3 M HCl and brine, dried over Na$_2$SO$_4$ and concentrated under vacuum. The resulting residue was purified with flash column chromatography (10-30% EtOAc in hexanes) to give the pure product 7 (2.56 g, 62% for two steps) as white solid.

Other substrates were prepared following the same procedure. 11a (0.69 g, 48%); 11b (0.94 g, 69%); 11c (1.87 g, 56%). Kothandaraman, P.; Rao, W.; Foo, S. J.; Chan, P. W. H. Angew. Chem. Int. Ed. 2010, 49, 4619.

(2.2) Preparation of Substrate 11d:

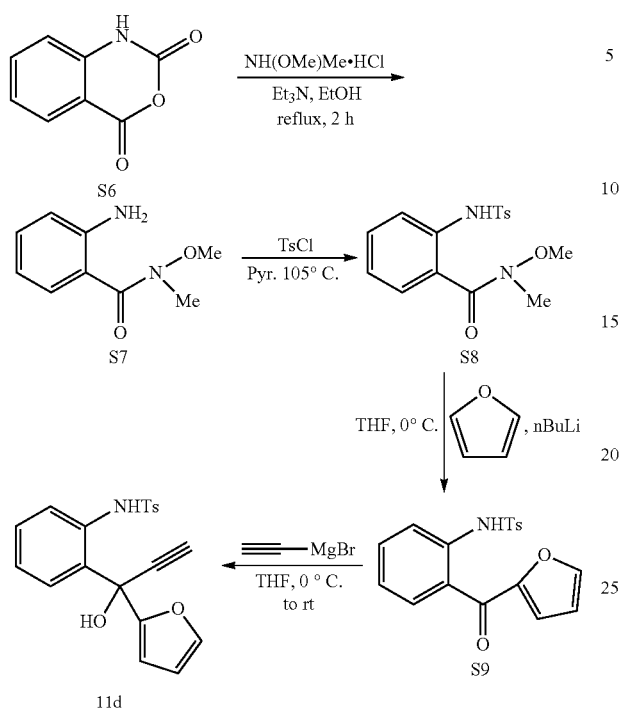

3. General Procedures for the Pt-Catalyzed Tandem Indole Annulation/Arylation:

To an oven-dried flask was added PtCl$_2$ (10 mol %), Na$_2$CO$_3$ (1.5 equiv), indole 5 (2.0 equiv), 4 (1.0 equiv) and dioxane (0.2 M for 4). The flask was degassed with Ar, sealed and heated to 100° C. overnight. After the reaction was completed, the solvent was evaporated under reduced pressure. The residue was purified by flash column chromatography on silica gel.

4. General Experimental Procedure for the Preparation of Diindolylmethanes:

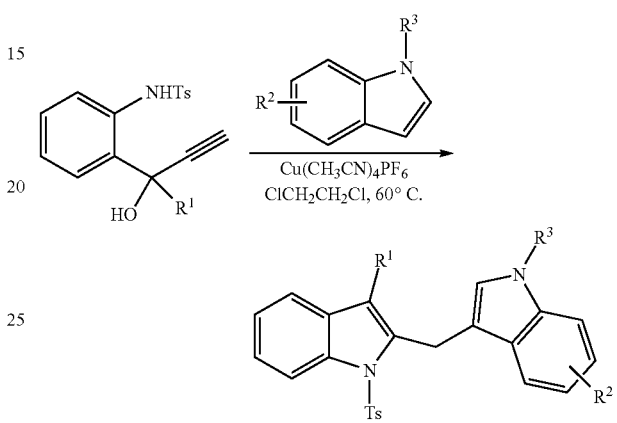

To a solution of N,O-dimethylhydroxylamine hydrochloride (14.6 g, 0.15 mol) in 90% aqueous ethanol (57 mL) was added triethylamine (20.8 mL, 0.15 mol) and after 10 min of stirring at room temperature. To the above solution was added isatonic anhydride S6 (16.3 g, 0.1 mol) in several portions. The reaction was then heated at reflux for 2 h and poured onto an equal volume of ice and saturated aqueous Na$_2$CO$_3$. The ethanol was then removed under vacuum and the resulting aqueous mixture was extracted with EtOAc. The combined organic layers were washed with water and brine, dried over Na$_2$SO$_4$ and concentrated. The resulting residue was purified by column chromatography on silica gel (10-30% EtOAc in hexanes) to give S7 as a yellow oil (14.4 g, 80%).

Following the same procedure for the preparation of 7 from S5, we prepared S8 from S7 in 50 mmol scale to obtain (8.16 g, 49%) of the product.

We adapted literature procedure for the preparation of S9. Kothandaraman, P.; Rao, W.; Foo, S. J.; Chan, P. W. H. *Angew. Chem. Int. Ed.* 2010, 49, 4619. To a solution of furan (0.48 mL, 6.0 mmol) in THF (20 mL) was added nBuLi (1.2 mL, 2.5 M in hexanes, 3.0 mmol) dropwise at −78° C. The solution was then allowed to warm to rt and stirred over night. The solution was then cooled to 0° C. To this solution was added S8 (0.67 g, 2.0 mmol) in THF (2 mL). After the addition was complete, the reaction was stirred at 0° C. for 4 h. Reaction was diluted with EtOAc and quenched with saturated aqueous NH$_4$Cl. The aqueous phase was extracted with EtOAc and the combined organic layers were washed with brine and dried over Na$_2$SO$_4$. The solvent was removed under vacuum and the resulting residue was purified by flash column chromatography (10-30% EtOAc in hexanes) to give product S9 (0.61 g, 89%) as colorless oil.

Following the same procedure for the preparation of S5 from S4, we prepared 11d from S9 in 0.59 mmol scale to obtain (0.18 g, 67%) of the product.

Propargylic alcohol (1.0 equiv) and tetrakis(acetonitrile) copper (I) hexafluorophosphate (10 mol %) were dissolved in 1,2-dichloroethane (0.1 M). To the above solution was added indole substrate (2.0 equiv). The mixture was stirred under argon at 60° C. for overnight. After the reaction was completed, the solvent was removed under reduced pressure. The crude product was purified by flash column chromatography (5% to 20% EtOAc in hexanes) to give the corresponding diindolylmethane.

5. Characterization Data for New Compounds:

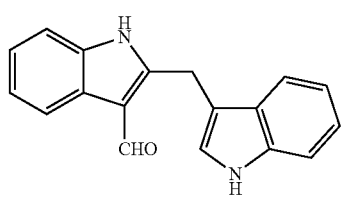

2-((1H-indol-3-yl)methyl)-1H-indole-3-carbaldehyde

To 0.3 mL of DMF was added POCl$_3$ (10 ul, 0.11 mmol) dropwise over 5 min at 0° C. After 10 min, a solution of bisindole 10 (25 mg, 0.1 mmol) in 0.2 ml of DMF was added. The solution was stirred at room temperature overnight and was poured into NaHCO$_3$ solution, extracted with ether, washed with 0.1 M NaOH solution, dried over MgSO$_4$ and purified by flash column chromatography (Hexane/ EtOAc=1.5:1) to provide a pinkish solid (20.5 mg, 75% yield, m.p.=235-236° C.).

$^1$H NMR (400 MHz, CCl$_4$:DMSO-d$_6$=1:4): δ 4.52 (s, 2H), 6.92 (t, J=6.8 Hz, 1H), 7.03 (t, J=7.2 Hz, 1H), 7.11 (m, 2H), 7.21 (s, 1H), 7.33 (m, 2H), 7.47 (d, J=8.0 Hz, 1H), 8.03 (m,

1H), 10.23 (s, 1H), 10.92 (br, 1H), 11.85 (br, 1H). $^{13}$C NMR (100 MHz, CCl$_4$:DMSO-d$_6$=1:4): 185.1, 152.0, 137.1, 136.3, 127.4, 126.4, 124.5, 123.4, 122.6, 122.0, 121.1, 119.4, 119.0, 113.9, 112.5, 112.3, 111.6, 22.9. IR (film): 3412, 2910, 1643, 1465, 1390, 1246, 822. All spectroscopic data are in accordance with literature. (Wille, G; Mayser, P; Thoma, W; Monsees, T; Baumgart, A; Schmitz, H. J.; Schrenk, D; Polborn, K; Steglich, W. *Bioorg. Med. Chem.* 2001, 9, 955.)

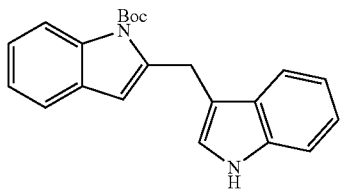

tert-butyl 2-((1H-indol-3-yl)methyl)-1H-indole-1-carboxylate

6a 205 mg, 83% yield; brown solid, m.p.=134-135° C. $^1$H NMR (400 MHz, CDCl$_3$, TMS): δ 1.60 (s, 9H), 4.49 (s, 2H), 6.17 (s, 1H), 7.01 (d, J=2.4 Hz, 1H), 7.09 (ddd, J=8.0, 6.8, 1.2 Hz, 1H), 7.14 (ddd, J=8.0, 6.8, 1.2 Hz, 1H), 7.21 (m, 2H), 7.33 (m, 1H), 7.39 (m, 1H), 7.56 (dd, J=8.4, 0.8 Hz, 1H), 8.00 (br, 1H), 8.11 (dd, J=8.4, 0.8 Hz, 1H). $^{13}$C NMR (125 MHz, CDCl$_3$): 26.7, 28.3, 83.9, 108.7, 111.3, 113.8, 115.6, 119.4, 119.5, 120.0, 122.2, 122.7, 122.8, 123.4, 127.6, 129.4, 136.4, 137.0, 141.0, 150.9. IR (film): v 3418, 2979, 1727, 1454, 1370, 1326, 1159, 1115, 1083, 906 cm$^{-1}$. HRMS (ESI) m/z calcd. for C$_{22}$H$_{22}$N$_2$O$_2$ (M+Na)$^+$ 369.1573, found 369.1580.

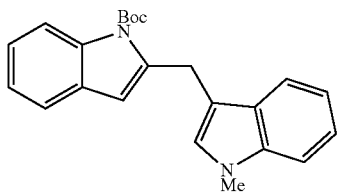

tert-butyl 2-((1-methyl-1H-indol-3-yl)methyl)-1H-indole-1-carboxylate

6b 49 mg, 88% yield; gray solid, m.p.=92-94° C. $^1$H NMR (500 MHz, CDCl$_3$, TMS): δ 1.64 (s, 9H), 3.78 (s, 3H), 4.51 (s, 2H), 6.20 (s, 1H), 6.90 (s, 1H), 7.12 (ddd, J=8.0, 7.2, 0.8 Hz, 1H), 7.18 (td, J=8.0, 1.2 Hz, 1H), 7.26 (m, 2H), 7.36 (m, 2H), 7.58 (dt, J=8.0, 1.2 Hz, 1H), 8.16 (dd, J=8.0, 0.8 Hz, 1H). $^{13}$C NMR (100 MHz, CDCl$_3$): 26.6, 28.3, 32.8, 83.8, 108.7, 109.3, 112.2, 115.6, 119.0, 119.5, 120.0, 121.7, 122.7, 123.0, 127.6, 128.0, 129.4, 137.0, 137.2, 141.3, 150.9. IR (film): v 2976, 1727, 1453, 1369, 1324, 1156, 1114, 1081, 907 cm$^{-1}$. HRMS (ESI) m/z calcd. for C$_{23}$H$_{25}$N$_2$O$_2$ (M+H)$^+$ 361.1911, found 361.1916.

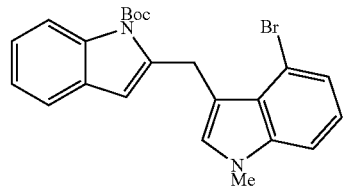

tert-butyl 2-((4-bromo-1-methyl-1H-indol-3-yl)methyl)-1H-indole-1-carboxylate

6c 66 mg, 68% yield; brown solid, m.p.=161-162° C. $^1$H NMR (500 MHz, CDCl$_3$, TMS): δ 1.61 (s, 9H), 3.76 (s, 3H), 4.79 (s, 2H), 6.19 (s, 1H), 6.79 (s, 1H), 7.11 (t, J=8.0 Hz, 1H), 7.23 (td, J=7.5, 1.0 Hz, 1H), 7.31 (m, 3H), 7.44 (d, J=7.0 Hz, 1H), 8.26 (dd, J=8.0, 1.0 Hz, 1H). $^{13}$C NMR (125 MHz, CDCl$_3$): 150.9, 141.6, 138.5, 137.2, 129.5, 128.9, 125.9, 123.5, 123.4, 122.7, 122.6, 120.0, 115.6, 114.8, 113.8, 109.1, 108.7, 83.8, 33.0, 29.9, 28.2. IR (film): v 2916, 1728, 1454, 1369, 1334, 1162, 1115, 1082, 908, 769, 736 cm$^{-1}$. HRMS (ESI) m/z calcd. for C$_{23}$H$_{24}$BrN$_2$O$_2$ (M+H)$^+$ 439.1016, found 439.1016.

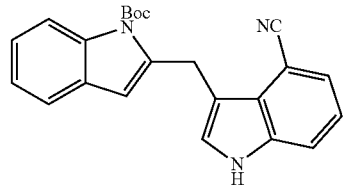

tert-butyl 2-((4-cyano-1H-indol-3-yl)methyl)-1H-indole-1-carboxylate

6d 62 mg, 81% yield; yellow solid, m.p.=155-157° C. $^1$H NMR (400 MHz, CDCl$_3$, TMS): δ 1.52 (s, 9H), 4.75 (s, 2H), 6.20 (s, 1H), 6.99 (s, 1H), 7.20 (m, 3H), 7.38 (dd, J=7.6, 0.4 Hz, 1H), 7.45 (dd, J=7.2, 0.8 Hz, 1H), 7.57 (dd, J=8.0, 0.8 Hz, 1H), 8.17 (d, J=8.0 Hz, 1H), 8.46 (br, 1H). $^{13}$C NMR (100 MHz, CDCl$_3$): 150.8, 140.2, 137.2, 136.6, 129.3, 126.7, 126.4, 125.7, 123.6, 122.7, 121.8, 120.0, 119.3, 116.3, 115.7, 114.6, 109.0, 102.3, 83.9, 28.2, 26.5. IR (film): v 3359, 2980, 2217, 1728, 1454, 1325, 1159, 1114, 1082, 907 cm$^{-1}$. HRMS (ESI) m/z calcd. for C$_{23}$H$_{22}$N$_3$O$_2$ (M+H)$^+$ 372.1707, found 372.1706.

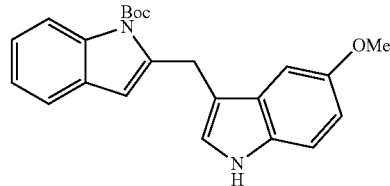

tert-butyl 2-((5-methoxy-1H-indol-3-yl)methyl)-1H-indole-1-carboxylate

6e 56 mg, 77% yield.; yellow solid, m.p.=98-99° C. $^1$H NMR (500 MHz, CDCl$_3$, TMS): δ 1.60 (s, 9H), 3.86 (s, 3H), 4.51

(s, 2H), 6.23 (s, 1H), 6.94 (dd, J=8.5, 2.5 Hz, 1H), 7.03 (t, J=2.5 Hz, 2H), 7.22 (dd, J=8.0, 1.0 Hz, 1H), 7.30 (m, 1H), 7.33 (d, J=9.0 Hz, 1H), 7.41 (d, J=8.0 Hz, 1H), 7.98 (br, 1H), 8.20 (dd, J=8.0, 1.0 Hz, 1H). $^{13}$C NMR (125 MHz, CDCl$_3$): 26.8, 28.3, 56.1, 83.9, 101.1, 108.7, 112.0, 112.5, 113.5, 115.6, 120.1, 122.7, 123.4, 123.6, 128.0, 129.4, 131.6, 137.0, 141.0, 150.9, 154.2. IR (film): v 3418, 2979, 1727, 1485, 1453, 1369, 1326, 1215, 1160, 1115, 1082, 907 cm$^{-1}$. HRMS (ESI) m/z calcd. for C$_{23}$H$_{25}$N$_2$O$_3$ (M+H)$^+$ 377.1860, found 377.1855.

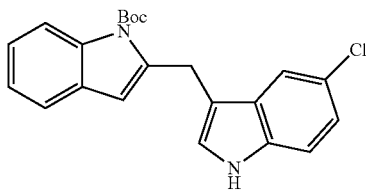

6f tert-butyl 2-((5-chloro-1H-indol-3-yl)methyl)-1H-indole-1-carboxylate 200 mg, 84% yield; yellow solid, m.p.=162-163° C. $^1$H NMR (400 MHz, CDCl$_3$, TMS): δ 1.60 (s, 9H), 4.43 (s, 2H), 6.13 (s, 1H), 6.98 (d, J=2.4 Hz, 1H), 7.23 (m, 4H), 7.35 (d, J=7.6 Hz, 1H), 7.53 (d, J=2.0 Hz, 1H), 8.01 (br, 1H), 8.11 (dd, J=8.4, 0.8 Hz, 1H). $^{13}$C NMR (100 MHz, CDCl$_3$): 150.9, 140.6, 137.0, 134.8, 129.3, 128.7, 125.4, 124.2, 123.6, 122.8, 122.5, 120.1, 118.8, 115.6, 113.7, 112.3, 108.7, 84.0, 28.3, 26.5. IR (film): 3416, 2981, 1728, 1707, 1453, 1368, 1327, 1220, 1157, 1115, 1080, 797, 746. HRMS (ESI) m/z calcd. for C$_{22}$H$_{22}$ClN$_2$O$_2$ (M+H)$^{+0}$ 381.1365, found 381.1348.

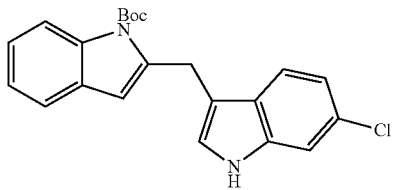

6g tert-butyl 2-((6-chloro-1H-indol-3-yl)methyl)-1H-indole-1-carboxylate 65 mg, 85%. yield; white solid, m.p.=155-156° C. $^1$H NMR (400 MHz, CDCl$_3$, TMS): δ 1.61 (s, 9H), 4.47 (s, 2H), 6.16 (s, 1H), 6.95 (m, 1H), 7.08 (m, 1H), 7.18 (m, 1H), 7.25 (m, 1H), 7.35 (m, 2H), 7.46 (m, 1H), 7.98 (br, 1H), 8.13 (m, 1H). $^{13}$C NMR (100 MHz, CDCl$_3$): 150.9, 140.6, 137.0, 136.8, 129.3, 128.1, 126.2, 123.6, 123.4, 122.8, 120.39, 120.33, 120.1, 115.6, 114.1, 111.2, 108.7, 84.0, 28.3, 26.6. IR (film): v 3427, 2977, 1728, 1453, 1393, 1325, 1157, 1115, 1063, 905, 803 cm$^{-1}$. HRMS (ESI) m/z calcd. for C$_{22}$H$_{22}$ClN$_2$O$_2$ (M+H)$^+$ 381.1365, found 381.1360.

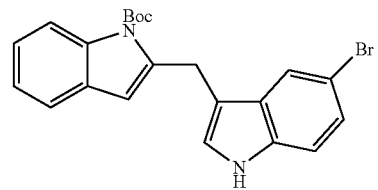

6h tert-butyl 2-((5-bromo-1H-indol-3-yl)methyl)-1H-indole-1-carboxylate 70 mg, 82% yield; brown solid, m.p.=159-160° C. $^1$H NMR (500 MHz, CDCl$_3$, TMS): δ 1.62 (s, 9H), 4.34 (s, 2H), 6.04 (s, 1H), 6.86 (s, 1H), 7.07 (t, J=7.5 Hz, 1H), 7.15 (m, 3H), 7.27 (d, J=7.5 Hz, 1H), 7.60 (d, J=2.0 Hz, 1H), 7.96 (br, 1H), 8.07 (dd, J=8.0, 1.5 Hz, 1H). $^{13}$C NMR (125 MHz, CDCl$_3$): 150.9, 140.6, 137.0, 135.0, 129.38, 129.32, 125.1, 124.1, 123.6, 122.8, 121.9, 120.1, 115.6, 113.5, 112.9, 112.8, 108.7, 84.0, 28.3, 26.5. IR (film): 3421, 2980, 1728, 1454, 1369, 1327, 1156, 1115, 1084, 907, 795. HRMS (ESI) m/z calcd. for C$_{22}$H$_{22}$BrN$_2$O$_2$ (M+H)$^+$ 425.0860, found 425.0860.

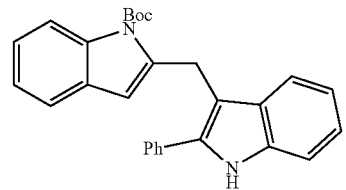

6i tert-butyl 2-((2-phenyl-1H-indol-3-yl)methyl)-1H-indole-1-carboxylate 270 mg, 80%.yield; white solid, m.p.=145-146° C. $^1$H NMR (400 MHz, CDCl$_3$, TMS): δ 1.68 (s, 9H), 4.55 (s, 2H), 6.05 (s, 1H), 7.11 (m, 2H), 7.21-7.41 (m, 7H), 7.49 (m, 3H), 8.14 (br, 2H), 8.17 (dd, J=8.4, 0.8 Hz, 1H). $^{13}$C NMR (100 MHz, CDCl$_3$): 26.6, 28.5, 84.1, 108.9, 109.7, 111.0, 115.7, 119.6, 120.0, 120.1, 122.6, 122.7, 123.4, 127.7, 128.0, 129.1, 129.5, 132.7, 135.8, 136.1, 137.1, 141.6, 151.1. IR (film): v 3412, 2997, 2974, 1730, 1454, 1369, 1326, 1248, 1161, 1114, 1082, 908, 737, 698 cm$^{-1}$. HRMS (ESI) m/z calcd. for C$_{28}$H$_{27}$N$_2$O$_2$ (M+H)$^+$ 423.2068, found 423.2059.

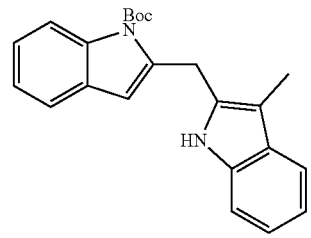 [SMILES: Cc1c(Cc2cc3ccccc3n2C(=O)OC(C)(C)C)[nH]c2ccccc12]

6j tert-butyl 2-((3-methyl-1H-indol-2-yl)methyl)-1H-indole-1-carboxylate 105 mg, 60% yield; brown solid, m.p.=144-145° C. $^1$H NMR (500 MHz, CDCl$_3$, TMS): δ 1.76 (s, 9H), 2.37 (s, 3H), 4.56 (s, 2H), 6.31 (s, 1H), 7.15 (td, J=7.5, 1.0 Hz, 1H), 7.19 (td, J=7.0, 1.5 Hz, 1H), 7.23 (td, J=7.5, 1.0 Hz, 1H), 7.29 (m, 2H), 7.46 (dd, J=7.5, 1.0 Hz, 1H), 7.58 (d, J=8.0 Hz, 1H), 8.08 (dd, J=8.0, 1.0 Hz, 1H), 8.23 (br, 1H). $^{13}$C NMR (125 MHz, CDCl$_3$): 151.2, 138.9, 136.6, 135.3, 131.7, 129.3, 129.3, 123.8, 123.0, 121.5, 120.2, 119.1, 118.5, 115.8, 110.6, 109.2, 108.4, 84.6, 28.4, 27.3, 8.7. IR (film): 3418, 2980, 1732, 1454, 1371, 1330, 1163, 1117, 1083, 909. HRMS (ESI) m/z calcd. for C$_{23}$H$_{25}$N$_2$O$_2$ (M+H)$^+$ 361.1911, found 361.1901.

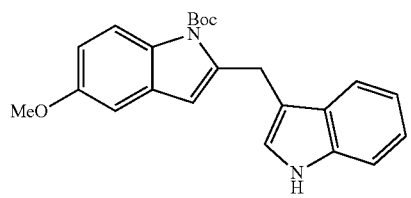

8a tert-butyl 2-((1H-indol-3-yl)methyl)-5-methoxy-1H-indole-1-carboxylate 58 mg, 77% yield; yellow solid, m.p.=97-98° C. $^1$H NMR (400 MHz, CDCl$_3$, TMS): δ 1.62 (s, 9H), 3.80 (s, 3H), 4.48 (s, 2H), 6.10 (s, 1H), 6.83 (d, J=2.8 Hz, 1H), 6.85 (dd, J=9.2, 2.8 Hz, 1H), 7.00 (d, J=2.4 Hz, 1H), 7.11 (ddd, J=8.0, 7.2, 0.8 Hz, 1H), 7.22 (ddd, J=8.0, 7.2, 1.2 Hz, 1H), 7.39 (dt, J=8.4, 0.8 Hz, 1H), 7.57 (d, J=7.6 Hz, 1H), 8.11 (br, 1H), 8.02 (d, J=8.8 Hz, 1H). $^{13}$C NMR (100 MHz, CDCl$_3$): 155.9, 150.8, 141.8, 136.4, 131.7, 130.2, 127.6, 122.8, 122.2, 119.5, 119.4, 116.4, 113.8, 111.9, 111.3, 108.6, 102.8, 83.7, 55.8, 28.3, 26.8. IR (film): 3414, 2979, 1727, 1477, 1450, 1370, 1162, 1122, 1084, 908, 734. HRMS (ESI) m/z calcd. for C$_{23}$H$_{24}$N$_2$O$_3$Na(M+Na) 399.1680, found 399.1666.

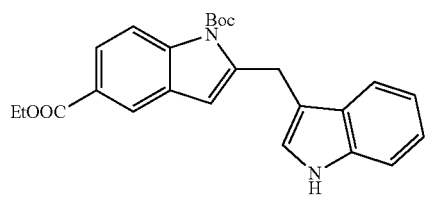

8b 2-(1H-Indol-3-ylmethyl)-indole-1,5-dicarboxylic acid 1-tert-butyl ester 5-ethyl Ester 49 mg, 62% yield; green solid, m.p.=100-102° C. $^1$H NMR (400 MHz, CDCl$_3$): δ 1.38 (t, J=7.08 Hz, 3H), 1.6 (s, 9H), 4.36 (q, J=7.16 Hz, 2H), 4.48 (s, 2H), 6.25 (s, 1H), 6.99 (d, J=2.32 Hz, 1H), 7.09 (ddd, J=8.00, 7.09, 1.00 Hz, 1H), 7.22 (ddd, J=8.16, 7.00, 1.2 Hz, 1H) 7.38 (d, J=8.2, 1H), 7.54 (d, J=7.92 Hz, 1H), 7.94 (dd, J=8.84, 1.80 Hz, 1H) 8.08 (d, J=1.6 Hz, 2H), 8.15 (d, J=8.84 Hz, 1H); $^{13}$C NMR (CDCl$_3$, 100 MHz): δ 14.61, 26.81, 28.33, 60.94, 84.67, 109.09, 111.42, 113.47, 115.26, 119.36, 119.71, 122.24, 122.36, 122.90, 124.88, 125.01, 127.53, 129.13, 136.55, 139.80, 142.50, 150.62, 161.39. IR (film) 730.94, 906.99, 1086.17, 1159.77, 1242.33, 1370.15, 1709.71 v cm$^{-1}$. HRMS (ESI) m/z calcd for C$_{25}$H$_{26}$N$_2$O$_4$ (M+H)$^+$ 419.1966, found 419.1980.

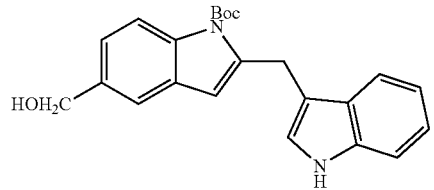

8c

5-Hydroxymethyl-2-(1H-indol-3-ylmethyl)-indole-1-carboxylic Acid tert-butyl Ester 25 mg, 55% yield; brown oil. $^1$H NMR (400 MHz, CDCl$_3$): δ 1.59 (s, 9H), 4.46 (s, 2H), 4.69 (s, 2H), 6.14 (s, 1H), 6.94 (d, J=2.40 Hz, 1H), 7.08 (ddd, J=7.96, 7.00, 1.04 Hz, 1H), 7.17-7.23 (m, 2H) 7.38 (d, J=1.04 Hz, 1H), 7.36 (dt, J=8.16, 1.00 Hz, 1H), 7.56 (dq, J=7.92, 1.00 Hz, 1H) 8.03 (s, 1H), 8.09 (d, J=9.64 Hz, 1H); $^{13}$C NMR (CDCl$_3$, 100 MHz): δ 26.82, 28.38, 65.92, 84.13, 108.77, 111.38, 113.79, 115.78, 118.80, 119.44, 119.63, 122.27, 122.88, 1229, 127.61, 129.64, 135.47, 136.54, 136.70, 141.67, 150.90. IR (film) 731.67, 908.08, 1032.86, 1252.46, 1315.52, 1726.58 v cm$^{-1}$. HRMS (ESI) m/z calcd for C$_{23}$H$_{24}$N$_2$O$_3$ (M+H)$^+$ 377.1860, found 377.1863.

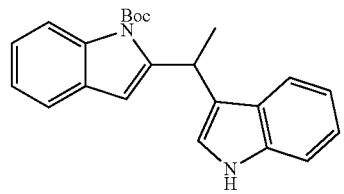 [SMILES: c1ccc2[nH]c(Cc3c[nH]c4ccccc34)cc2c1]

8d tert-butyl 2-(1-(1H-indol-3-yl)ethyl)-1H-indole-1-carboxylate 25 mg, 70% yield, brown solid, m.p.=141-142° C. $^1$H NMR (400 MHz, CDCl$_3$, TMS): δ 1.47 (s, 9H), 1.75 (d, J=7.2 Hz, 3H), 5.19 (q, J=7.2 Hz, 1H), 6.35 (s, 1H), 6.78 (dd, J=2.4, 0.8 Hz, 1H), 7.07 (ddd, J=8.0, 6.7, 0.8 Hz, 1H), 7.17 (m, 2H), 7.23 (ddd, J=8.8, 6.8, 1.6 Hz, 1H), 7.34 (dt, J=8.0, 0.8 Hz, 1H), 7.40 (ddd, J=7.6, 1.6, 0.8 Hz, 1H), 7.56 (d, J=8.0 Hz, 1H), 7.90 (br, 1H), 8.10 (dd, J=8.4, 0.8 Hz, 1H). $^{13}$C NMR (100 MHz, CDCl$_3$): 150.7, 146.0, 137.3, 136.7, 129.2, 126.8, 123.5, 122.6, 122.1, 121.3, 121.0, 120.2, 119.8, 119.4, 115.5, 111.3, 107.3, 83.8, 30.8, 28.1, 21.4. IR (film): v 3421, 2976, 2362, 1728, 1454, 1368, 1326, 1156, 1116, 908 cm$^{-1}$; HRMS (ESI) m/z calcd. for C$_{23}$H$_{24}$N$_2$O$_2$ (M+H)$^+$ 361.1911, found 361.1908.

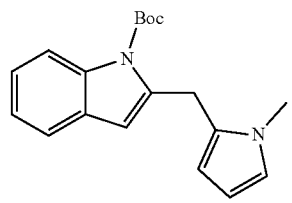

9 tert-butyl 2-((1-methyl-1H-pyrrol-2-yl)methyl)-1H-indole-1-carboxylate 21 mg, 68% yield; brown oil. $^1$H NMR (400 MHz, CDCl$_3$, TMS): δ 1.66 (s, 9H), 3.52 (s, 3H), 4.29 (s, 2H), 5.92 (s, 1H), 5.98 (m, 1H), 6.12 (m, 1H), 6.64 (m, 1H), 7.22 (m, 2H), 7.35 (d, J=8.0 Hz, 1H), 8.11 (d, J=8.0 Hz, 1H). $^{13}$C NMR (100 MHz, CDCl$_3$): 28.1, 28.4, 33.8, 84.1, 107.0, 108.2, 108.6, 115.7, 120.1, 121.8, 122.8, 123.6, 129.3, 129.7, 136.9, 140.1, 150.8. IR (film): v 2976, 1729, 1454, 1369, 1161, 1081, 744 cm$^{-1}$. HRMS (ESI) m/z calcd. for C$_{19}$H$_{22}$N$_2$O$_2$ (M+Na)$^+$ 333.1573, found 333.1575.

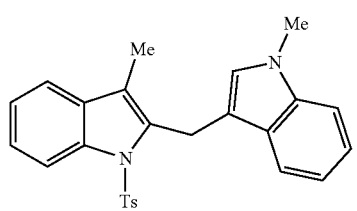

9a

Compound 9a was isolated as brown oil (16 mg, 76%, [0.05 mmol]; 62 mg, 73% [0.2 mmol]). $^1$H NMR (500 MHz, CDCl$_3$, TMS): δ 8.23 (d, J=5.0 Hz, 1H), 7.60 (d, J=10.0 Hz, 1H), 7.44 (d, J=10.0 Hz, 1H), 7.30-7.24 (m, 4H), 7.22-7.19 (m, 2H), 7.11-7.08 (m, 1H), 6.86 (d, J=10.0 Hz, 2H), 6.39 (s, 1H), 4.51 (s, 2H), 3.53 (s, 3H), 2.24 (s, 3H), 2.23 (s, 3H). $^{13}$C NMR (100 MHz, CDCl$_3$): δ 144.1, 137.1, 137.0, 136.5, 135.7, 131.4, 129.3, 127.74, 127.69, 126.5, 124.5, 123.5, 121.7, 119.2, 119.1, 118.8, 117.3, 115.4, 112.1, 109.2, 32.7, 22.1, 21.7, 9.5. IR (neat) v 3681, 3639, 2928, 1652, 1537. HRMS (ESI) m/z calcd for C$_{26}$H$_{24}$N$_2$O$_2$S (M+Na)$^+$ 451.1451, found 451.1460.

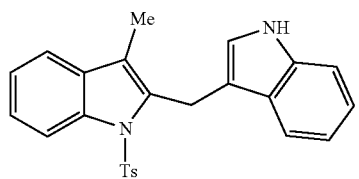

9b

Compound 9b was isolated as white solid (15 mg, 75%). mp=176-178° C. $^1$H NMR (500 MHz, CDCl$_3$, TMS): δ 8.20 (d, J=10.0 Hz, 1H), 7.80 (s, 1H), 7.58 (d, J=10.0, 1H), 7.42 (d, J=5.0 Hz, 1H), 7.33 (d, J=10.0 Hz, 2H), 7.30-7.22 (m, 3H), 7.14 (t, J=10.0 Hz, 1H), 7.07 (t, J=10.0 Hz, 1H), 6.87 (d, J=5.0 Hz, 2H), 6.60 (s, 1H), 4.51 (s, 2H), 2.21 (s, 3H), 2.19 (s, 3H). $^{13}$C NMR (125 MHz, CDCl$_3$): δ 144.2, 136.9, 136.4, 136.2, 135.5, 131.5, 129.4, 127.3, 126.5, 124.5, 123.5, 123.0, 122.1, 119.6, 119.0, 118.8, 117.6, 115.4, 113.7, 111.3, 22.3, 21.7, 9.5. IR (neat) v 3676, 2948, 1734, 1692, 1660, 1530. HRMS (ESI) m/z calcd for C$_{25}$H$_{22}$N$_2$O$_2$S (M+Na)$^+$ 437.1294, found 437.1297. X-ray structure (CCDC 1016687).

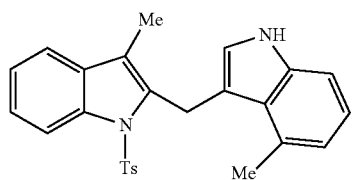

9c

Compound 9c was isolated as pink oil (33 mg, 77%). $^1$H NMR (400 MHz, CDCl$_3$, TMS): δ 8.28 (d, J=8.0 Hz, 1H), 7.64 (s, 1H), 7.46 (d, J=8.0 Hz, 1H), 7.40 (d, J=8.0 Hz, 2H), 7.36-7.26 (m, 2H), 7.14-7.13 (m, 1H), 7.06 (d, J=8.0 Hz, 1H), 6.93 (d, J=8.0 Hz, 2H), 6.88 (d, J=8.0 Hz, 1H), 6.13 (s, 1H), 4.78 (s, 2H), 2.84 (s, 3H), 2.24 (s, 3H), 2.15 (s, 3H). $^{13}$C NMR (125 MHz, CDCl$_3$): δ 144.3, 137.1, 136.8, 136.5, 135.5, 131.4, 131.3, 129.5, 126.8, 126.0, 124.5, 123.4, 122.44, 122.38, 121.3, 118.7, 117.4, 115.3, 115.0, 109.2, 24.4, 21.8, 21.0, 9.1. IR (neat) v 3361, 2925, 1717, 1685, 1647, 1521. HRMS (ESI) m/z calcd for C$_{26}$H$_{24}$N$_2$O$_2$S (M+Na)$^+$ 451.1451, found 451.1454.

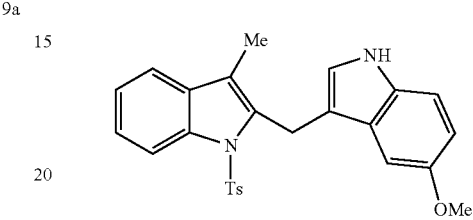

9d

Compound 9d was isolated as yellow oil (21 mg, 95%). $^1$H NMR (500 MHz, CDCl$_3$, TMS): δ 8.20 (d, J=5.0 Hz, 1H), 7.69 (s, 1H), 7.43 (d, J=10.0 Hz, 1H), 7.34 (d, J=5.0 Hz, 2H), 7.31-7.28 (m, 1H), 7.18 (d, J=5.0 Hz, 1H), 7.03 (d, J=2.5 Hz, 1H), 6.91 (d, J=10.0 Hz, 2H), 6.82 (dd, J=10.0, 2.5 Hz, 1H), 6.63 (s, 1H), 4.50 (s, 2H), 3.82 (s, 3H), 2.25 (s, 3H), 2.23 (s, 3H). $^{13}$C NMR (125 MHz, CDCl$_3$): δ 154.3, 144.2, 136.9, 136.3, 135.5, 131.6, 131.5, 129.4, 127.7, 126.6, 124.5, 123.7, 123.5, 118.7, 117.6, 115.4, 113.6, 112.4, 111.9, 101.0, 56.1, 22.4, 21.7, 9.5. IR (neat) v 3662, 3447, 2943, 1717, 1652, 1537, 1521. HRMS (ESI) m/z calcd for C$_{26}$H$_{24}$N$_2$O$_3$S (M+Na)$^+$ 467.1400, found 467.1403.

9e

Compound 9e was isolated as a yellow oil (29 mg, 68% yield). $^1$H NMR (400 MHz, CDCl$_3$, TMS): δ 8.21 (d, J=8.0 Hz, 1H), 7.69 (s, 1H), 7.45-7.34 (m, 4H), 7.33-7.26 (m, 2H), 7.20 (d, J=8.4 Hz, 1H), 7.00 (d, J=8.0 Hz, 1H), 6.93 (d, J=8.4 Hz, 2H), 6.56 (d, J=1.2 Hz, 1H), 4.50 (s, 2H), 2.46 (s, 3H), 2.24 (s, 3H), 2.20 (s, 3H). $^{13}$C NMR (126 MHz, CDCl$_3$): δ 144.2, 136.9, 136.3, 135.6, 134.8, 131.5, 129.5, 128.9, 127.6, 126.6, 124.4, 123.9, 123.5, 123.0, 118.8, 118.7, 117.6, 115.4, 113.4, 110.9, 22.2, 21.9, 21.7, 9.5. IR (neat) v 3360, 2944, 2925, 1652, 1521 cm$^{-1}$. HRMS (ESI) for C$_{26}$H$_{24}$N$_2$O$_2$S (M+Na), 451.1451 (Calc.), found 451.1448

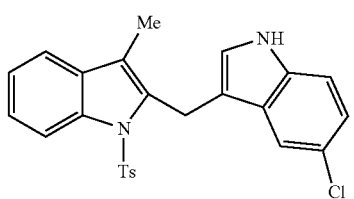

9f

Compound 9f was isolated as yellow oil (14 mg, 63%). $^{1}$H NMR (500 MHz, CDCl$_3$, TMS): δ 8.20 (d, J=5.0 Hz, 1H), 7.86 (s, 1H), 7.54 (d, J=2.0 Hz, 1H), 7.44 (d, J=5.0 Hz, 1H), 7.38 (d, J=10.0 Hz, 2H), 7.32-7.27 (m, 2H), 7.20 (d, J=10.0 Hz, 1H), 7.11 (dd, J=10.0, 2.0 Hz, 1H), 6.96 (d, J=10.0 Hz, 2H), 6.71 (s, 1H), 4.46 (s, 2H), 2.25 (s, 3H), 2.23 (s, 3H). $^{13}$C NMR (125 MHz, CDCl$_3$): δ 144.4, 137.0, 136.3, 135.0, 134.7, 131.5, 129.6, 128.4, 126.5, 125.4, 124.6, 124.4, 123.6, 122.5, 118.9, 118.6, 117.8, 115.4, 113.8, 112.2, 22.3, 21.8, 9.5. IR (neat) ν 3399, 2926, 2253, 1726, 1598. HRMS (ESI) m/z calcd for C$_{25}$H$_{21}$ClN$_2$O$_2$S (M+Na)$^+$ 471.0904, found 471.0905.

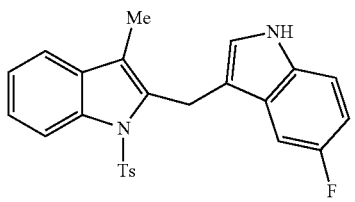

9g

Compound 9g was isolated as a brown solid (43 mg, 70% yield). mp=55-60° C. $^{1}$H NMR (500 MHz, CDCl$_3$): δ 2.158 (s, 3H), 2.161 (s, 3H), 4.38 (s, 2H), 6.67 (d, J=0.5 Hz, 1H), 6.81 (td, J=7.5, 2.5 Hz, 1H), 6.86 (d, J=8.5 Hz, 2H), 7.09-7.12 (m, 2H), 7.18-7.23 (m, 2H), 7.28 (d, J=8.5 Hz, 2H), 7.36 (d, J=8.5 Hz, 1H), 7.78 (broad s, 1H), 8.12 (d, J=7.5, 1H). $^{13}$C NMR (100 MHz, CDCl$_3$): δ 9.5, 21.7, 22.4, 104.0 (d, J=22.9 Hz), 110.5 (d, J=26.7 Hz), 111.8 (d, J=9.1 Hz), 114.1, 115.4, 117.8, 118.9, 123.6, 124.6, 124.9, 126.5, 129.5, 131.5, 132.9, 135.1, 136.3, 137.0, 144.3, 158.0 (d, J=232.9 Hz). 6 IR (neat) 1358.92, 1486.49, 1581.04, 1597.66, 1710.37, 2853.40, 2923.35, 3422.05 ν cm$^{-1}$. HRMS (ESI) M/Z calcd. for C$_{25}$H$_{21}$FN$_2$O$_2$S (M+Na)$^+$ 455.1200, found 455.1200.

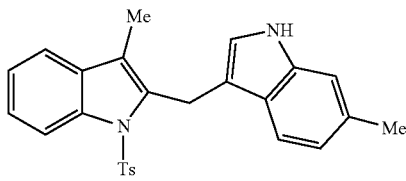

9h

Compound 9h was isolated as yellow oil (33 mg, 77%). $^{1}$H NMR (400 MHz, CDCl$_3$, TMS): δ 8.20 (d, J=4.0 Hz, 1H), 7.67 (s, 1H), 7.46 (d, J=8.0 Hz, 1H), 7.43-7.41 (m, 1H), 7.34 (d, J=8.0 Hz, 2H), 7.31-7.25 (m, 1H), 7.23-7.19 (m, 1H), 7.08 (s, 1H), 6.93-6.90 (m, 3H), 6.58 (s, 1H), 4.50 (s, 2H), 2.44 (s, 3H), 2.23 (s, 3H), 2.22 (s, 3H). $^{13}$C NMR (100 MHz, CDCl$_3$): δ 144.2, 136.93, 136.91, 136.3, 135.7, 132.0, 131.5, 129.5, 126.6, 125.3, 124.4, 123.5, 122.3, 121.5, 118.8, 118.7, 117.5, 115.4, 113.7, 111.2, 22.3, 22.0, 21.7, 9.5. IR (neat) ν 3663, 3446, 2949, 2882, 1734, 1717, 1652, 1537. HRMS (ESI) m/z calcd for C$_{26}$H$_{24}$N$_2$O$_2$S (M+Na)$^+$ 451.1451, found 451.1445.

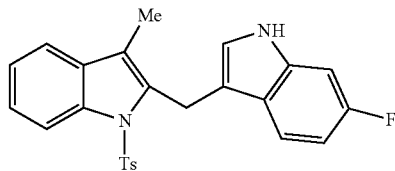

9i

Compound 9i was isolated as colorless oil (30 mg, 70%). $^{1}$H NMR (400 MHz, CDCl$_3$, TMS): δ 8.20 (d, J=8.0 Hz, 1H), 7.80 (s, 1H), 7.49-7.43 (m, 2H), 7.33 (d, J=8.0 Hz, 2H), 7.30-7.25 (m, 2H), 6.98 (dd, J=9.6, 2.4 Hz, 1H), 6.93 (d, J=8.0 Hz, 2H), 6.88-6.83 (m, 1H), 6.66-6.65 (m, 1H), 4.50 (s, 2H), 2.25 (s, 3H), 2.24 (s, 3H). $^{13}$C NMR (100 MHz, CDCl$_3$): δ 160.3 (d, J=236.8 Hz), 144.3, 137.0, 136.3, 135.2, 131.4, 129.5, 126.5, 124.6, 124.0, 123.6, 123.2, 119.9 (d, J=10 Hz), 118.8, 117.7, 115.4, 114.1, 108.5 (d, J=24 Hz), 97.5 (d, J=26 Hz), 22.3, 21.7, 9.5. IR (neat) ν 3649, 2948, 1734, 1692, 1641, 1513. HRMS (ESI) m/z calcd for C$_{25}$H$_{22}$N$_2$O$_2$SF (M+Na)$^+$ 455.1200, found 455.1198.

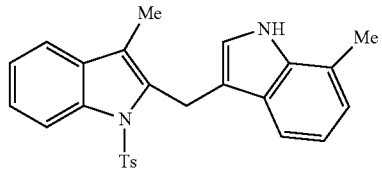

9j

Compound 9j was isolated as a yellow oil (28 mg, 67% yield). $^{1}$H NMR (400 MHz, CDCl$_3$, TMS): δ 8.20 (d, J=8.0 Hz, 1H), 7.69 (s, 1H), 7.43 (d, J=7.6 Hz, 2H), 7.37-7.22 (m, 4H), 6.98 (m, 2H), 6.88 (d, J=8.4 Hz, 2H), 6.63 (d, J=1.2 Hz, 1H), 4.51 (s, 2H), 2.42 (s, 3H), 2.22 (s, 3H), 2.22 (s, 3H). $^{13}$C NMR (100 MHz, CDCl$_3$): δ 144.1, 137.0, 136.4, 135.6, 131.5, 129.4, 126.9, 126.5, 124.5, 123.5, 122.73, 122.69, 120.3, 119.9, 118.8, 117.6, 116.9, 115.4, 114.4, 22.5, 21.7, 16.8, 9.5. IR (neat) ν 3388, 2922, 2854, 1652, 1457 cm$^{-1}$. HRMS (ESI) for C$_{26}$H$_{24}$N$_2$O$_2$S (M+Na), 451.1451 (Calc.), found 451.1449.

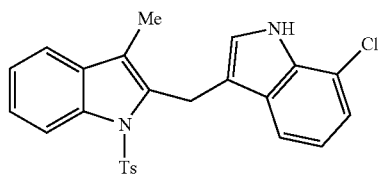

9k

Compound 9k was isolated as colorless oil (26 mg, 59%). $^{1}$H NMR (500 MHz, CDCl$_3$, TMS): δ 8.21 (d, J=5.0 Hz, 1H), 7.95 (s, 1H), 7.47-7.43 (m, 2H), 7.33-7.24 (m, 3H), 7.14 (d, J=5.0 Hz, 1H), 7.01-6.98 (m, 1H), 6.85 (d, J=10.0 Hz, 2H), 6.67 (s, 1H), 4.50 (s, 2H), 2.26 (s, 3H), 2.22 (s, 3H). $^{13}$C NMR (125 MHz, CDCl$_3$): δ 144.2, 137.1, 136.4, 135.0, 133.6, 131.2, 129.3, 128.8, 126.2, 124.7, 123.7, 123.5, 121.5, 120.5, 118.8, 117.6, 116.7, 115.3, 114.9, 22.4, 21.7, 9.5. IR (neat) ν 3674, 3384, 2949, 1734, 1717, 1678, 1641, 1631, 1513. HRMS (ESI) m/z calcd for C$_{25}$H$_{21}$ClN$_2$O$_2$S (M+Na)$^+$ 471.0904, found 471.0897.

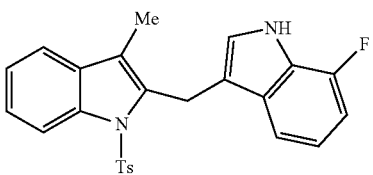

91

Compound 91 was isolated as brown oil (35 mg, 81%). $^1$H NMR (400 MHz, CDCl$_3$, TMS): δ 8.13 (d, J=8.0 Hz, 1H), 7.87 (s, 1H), 7.39-7.37 (m, 1H), 7.25-7.18 (m, 6H), 6.91 (ddd, J=20.0, 12.0, 4.0 Hz, 1H), 6.83 (d, J=8.0 Hz, 2H), 6.62 (s, 1H), 4.44 (s, 2H), 2.18 (s, 3H), 2.16 (s, 3H). $^{13}$C NMR (100 MHz, CDCl$_3$): δ 149.7 (d, J=242.8 Hz), 144.3, 137.1, 136.4, 135.1, 131.2 (d, J=29.8 Hz), 129.9, 129.2 (d, J=40 Hz), 126.4, 124.6, 123.7, 123.6, 120.0 (d, J=6.1 Hz), 118.8, 117.7, 115.4, 115.0, 114.9, 114.8, 107.0 (d, J=15 Hz), 22.4, 21.7, 9.5. IR (neat) v 3801, 3344, 1749, 1734, 1652, 1530. HRMS (ESI) m/z calcd for C$_{25}$H$_{21}$FN$_2$O$_2$S (M+Na)$^+$ 455.1200, found 455.1202.

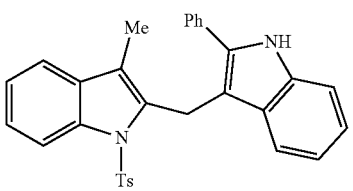

9m

Compound 9m was isolated as colorless oil (35 mg, 71%). $^1$H NMR (500 MHz, CDCl$_3$, TMS): δ 8.25 (d, J=5.0 Hz, 1H), 8.04 (s, 1H), 7.51 (d, J=10.0 Hz, 2H), 7.41-7.22 (m, 9H), 7.08 (t, J=10.0 Hz, 1H), 7.00-6.94 (m, 3H), 6.84-6.81 (m, 1H), 4.66, (s, 2H), 2.26 (s, 3H), 1.81 (s, 3H). $^{13}$C NMR (125 MHz, CDCl$_3$): δ 144.3, 137.0, 136.6, 135.9, 135.2, 134.3, 133.2, 131.7, 129.6, 129.3, 129.1, 128.4, 128.0, 126.3, 124.5, 123.4, 122.4, 120.0, 119.6, 118.6, 118.0, 115.2, 110.9, 109.4, 24.0, 21.8, 9.0. IR (neat) v 3675, 2948, 1749, 1734, 1661, 1513. HRMS (ESI) m/z calcd for C$_{31}$H$_{26}$N$_2$O$_2$S (M+Na)$^+$ 513.1607, found 513.1617.

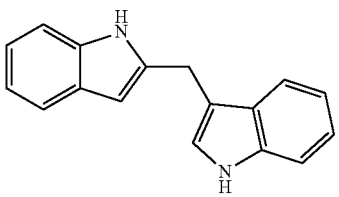

10

3-((1H-indol-2-yl)methyl)-1H-indole

Neat compound 6a (49 mg, 0.18 mmol) was heated at 160° C. for 45 min, the residue was purified by flash column chromatography on silica gel (Hexane/EtOAc=8:1 to 4:1) to provide 25 mg of free bisindole 10 (70% yield) as a pinkish solid (m.p.=136-137° C.).

$^1$H NMR (400 MHz, CDCl$_3$, TMS): δ 4.26 (s, 2H), 6.38 (m, 1H), 7.00 (m, 1H), 7.07 (m, 3H), 7.20 (m, 2H), 7.34 (d, J=8.0 Hz, 1H), 7.53 (m, 2H), 7.79 (br, 1H), 7.92 (br, 1H). $^1$H NMR (400 MHz, DMSO-d$_6$): δ 4.19 (s, 2H), 6.17 (s, 1H), 6.95 (m, 3H), 7.07 (td, J=6.4, 0.8 Hz, 1H), 7.24 (d, J=1.6 Hz, 1H), 7.27 (d, J=6.4 Hz, 1H), 7.37 (d, J=6.4 Hz, 1H), 7.39 (d, J=6.4 Hz, 1H), 7.50 (d, J=6.4 Hz, 1H), 10.89 (br, 2H). $^{13}$C NMR (100 MHz, CDCl$_3$): 138.4, 136.6, 136.1, 129.0, 127.4, 122.8, 122.5, 121.1, 120.0, 119.9, 119.7, 119.2, 113.0, 111.4, 110.6, 100.2, 24.6. IR (film): 3403, 2926, 1458, 1418, 1342, 1285, 908 cm$^{-1}$. All spectroscopic data are in accordance with literature. Zhang, J.; Zhu, D.; Yu, C.; Wan, C.; Wang, Z., Org. Lett. 2010, 12, 2841.

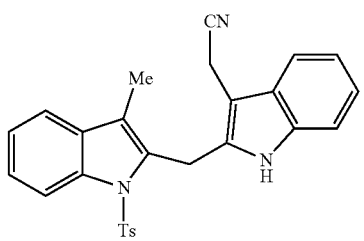

10a

Compound 10a was isolated as colorless oil (35 mg, 78%). $^1$H NMR (400 MHz, CDCl$_3$, TMS): δ 8.20 (d, J=8.0 Hz, 1H), 8.17 (s, 1H), 7.58-7.56 (m, 1H), 7.47 (d, J=8.0 Hz, 1H), 7.38-7.25 (m, 4H), 7.17-7.14 (m, 3H), 6.84 (d, J=8.0 Hz, 2H), 4.56 (s, 2H), 3.89 (s, 2H), 2.33 (s, 3H), 2.19 (s, 3H). $^{13}$C NMR (100 MHz, CDCl$_3$): δ 145.1, 137.1, 135.6, 135.2, 132.9, 131.6, 131.0, 129.8, 127.4, 126.2, 125.5, 124.1, 122.6, 120.5, 119.3, 119.2, 118.4, 118.0, 115.5, 111.3, 100.6, 23.3, 21.7, 13.3, 9.6. IR (neat) v 3337, 1734, 1717, 1652, 1513. HRMS (ESI) m/z calcd for C$_{27}$H$_{23}$N$_3$O$_2$S (M+Na)$^+$ 476.1403, found 476.1407.

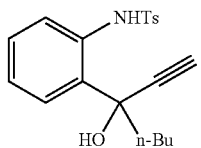

11a

Compound 11a was isolated as white solid (1.86 g, 61%). mp=85-86° C. $^1$H NMR (400 MHz, CDCl$_3$, TMS): δ 9.08 (s, 1H), 7.73 (d, J=8.0 Hz, 2H), 7.65 (d, J=8.0 Hz, 1H), 7.56 (dd, J=8.0, 1.6 Hz, 1H), 7.26-7.21 (m, 3H), 7.01 (t, J=8.0 Hz, 1H), 3.02 (s, 1H), 2.78 (s, 1H), 2.36 (s, 3H), 1.79-1.71 (m, 1H), 1.67-1.60 (m, 1H), 1.38-1.32 (m, 1H), 1.17-0.98 (m, 3H), 0.80 (t, J=8.0 Hz, 3H). $^{13}$C NMR (100 MHz, CDCl$_3$): δ 143.9, 137.1, 135.7, 130.2, 129.8, 129.1, 128.7, 127.2, 123.5, 120.2, 84.8, 76.2, 76.0, 42.6, 27.0, 22.5, 21.6, 14.1. IR (neat) v 3675, 2949, 2877, 1734, 1717, 1692, 1641, 1513. HRMS (ESI) m/z calcd for C$_{20}$H$_{23}$NO$_3$S (M+Na)$^+$ 380.1291, found 380.1293.

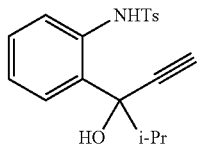

11b

Compound 11b was isolated as colorless solid (2.15 g, 76%). mp=111-113° C. $^1$H NMR (400 MHz, CDCl$_3$, TMS): δ 8.97 (s, 1H), 7.70 (d, J=8.0 Hz, 2H), 7.65 (d, J=8.0 Hz, 1H), 7.56 (d, J=8.0 Hz, 1H), 7.26-7.21 (m, 3H), 7.00 (t, J=8.0 Hz, 1H), 2.99 (s, 1H), 2.78 (s, 1H), 2.37 (s, 3H), 1.79 (m, 1H), 1.04 (d, J=8.0 Hz, 3H), 0.44 (d, J=8.0 Hz, 3H). $^{13}$C NMR (100 MHz, CDCl$_3$): δ 144.0, 137.4, 135.8, 130.0, 129.9, 129.8, 129.3, 127.3, 123.4, 120.9, 82.6, 80.4, 77.6, 37.2, 21.7, 18.5, 17.2. IR (neat) ν 3676, 2947, 1734, 1717, 1678, 1641, 1530. HRMS (ESI) m/z calcd for C$_{19}$H$_{21}$NO$_3$S (M+Na)$^+$ 366.1134, found 366.1137.

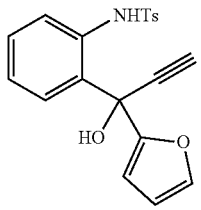

11d

Compound 11d was isolated as colorless solid (0.15 g, 67%). mp=123-124° C. $^1$H NMR (500 MHz, CDCl$_3$, TMS): δ 8.69 (s, 1H), 7.69 (d, J=5.0 Hz, 2H), 7.62 (d, J=10 Hz, 1H), 7.40-7.34 (m, 2H), 7.28-7.24 (m, 1H), 7.20 (d, J=10 Hz, 2H), 7.01-6.98 (m, 1H), 6.30-6.29 (m, 1H), 6.17 (d, J=5.0 Hz, 1H), 3.43 (s, 1H), 2.84 (s, 1H), 2.37 (s, 3H). $^{13}$C NMR (100 MHz, CDCl$_3$): δ 152.9, 143.9, 143.8, 137.1, 136.5, 130.1, 129.8, 129.0, 127.8, 127.7, 123.5, 119.6, 110.9, 109.2, 82.4, 76.9, 71.3, 21.8. IR (neat) ν 3681, 2944, 1734, 1652, 1537. HRMS (ESI) m/z calcd for C$_{20}$H$_{17}$NO$_4$S (M+Na)$^+$ 390.0771, found 390.0790.

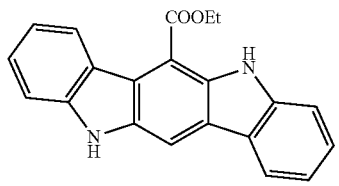

12

Ethyl 5,11-dihydroindolo[3,2-b]carbazole-6-carboxylate

To a solution of bisindole 10 (57 mg, 0.23 mmol) in 1.5 ml of THF at 0° C. under Ar was added 0.03 ml of pyridine quickly followed by ethyl oxalyl chloride (0.054 ml, 0.35 mmol) slowly over 10 min. The reaction was stirred for 6 h. The mixture was diluted with EtOAc, washed with 1 M HCl, then NaHCO$_3$ and dried over MgSO$_4$. The residue was purified by flash column chromatography on silica gel (Hexane/EtOAc=3:1 to 2:1). The purified intermediate was dissolved in 4 mL of dioxane and 0.1 mL of MeSO$_3$H was added dropwise. The solution was heated to reflux for 1 h and then cooled down to room temperature. Silica was added and the residue was purified by flash column chromatography on silica gel (Hexane/CH$_2$Cl$_2$=1:1) to yield a yellow solid (40 mg, 52% yield for two steps, m.p.=217-218° C.).

$^1$H NMR (400 MHz, acetone-d$_6$): δ 1.43 (t, J=6.8 Hz, 3H), 4.57 (q, J=6.8 Hz, 2H), 7.04 (qd, J=7.6, 0.8 Hz, 2H), 2.95 (td, J=7.2, 1.2 Hz, 2H), 7.40 (d, J=8.0 Hz, 1H), 7.51 (d, J=8.0 Hz, 1H), 8.04 (d, J=8.0 Hz, 1H), 8.35 (s, 1H), 8.83 (d, J=8.0 Hz, 1H), 10.40 (br, 2H). $^{13}$C NMR (100 MHz, acetone-d$_6$): 168.9, 143.4, 142.7, 138.3, 137.1, 127.7, 127.6, 127.2, 125.1, 123.7, 123.5, 122.5, 121.5, 120.3, 119.4, 112.5, 111.9, 108.2, 106.7, 62.2, 15.5. IR (film): 3393, 2976, 1675, 1610, 1510, 1455, 1416, 1295, 1111, 908, 870. All spectroscopic data are in accordance with literature. (Tholander, J; Bergman, J. *Tetrahedron*, 1999, 55, 6243.)

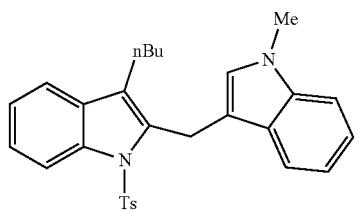

12a

Compound 12a was isolated as yellow oil (16 mg, 65%). $^1$H NMR (400 MHz, CDCl$_3$, TMS): δ 8.24 (d, J=8.0 Hz, 1H), 7.61 (d, J=8.0 Hz, 1H), 7.48 (d, J=8.0 Hz, 1H), 7.32-7.24 (m, 4H), 7.20 (d, J=4.0 Hz, 2H), 7.10 (ddd, J=20.0, 12.0, 4.0 Hz, 1H), 6.86 (d, J=8.0 Hz, 2H), 6.34 (s, 1H), 4.51 (s, 2H), 3.51 (s, 3H), 2.69 (t, J=8.0 Hz, 2H), 2.24 (s, 3H), 1.51 (m, 2H), 1.28 (m, 2H), 0.84 (t, J=8.0 Hz, 3H). $^{13}$C NMR (100 MHz, CDCl$_3$): δ 144.0, 137.3, 137.1, 136.4, 135.6, 130.9, 129.2, 127.74, 127.68, 126.5, 124.3, 123.4, 122.3, 121.7, 119.2, 119.1, 119.0, 115.6, 112.4, 109.2, 32.7, 32.4, 24.4, 22.9, 22.1, 21.7, 14.2. IR (neat) ν 3675, 2949, 1734, 1678, 1513. HRMS (ESI) m/z calcd for C$_{29}$H$_{30}$N$_2$O$_2$S (M+Na)$^+$ 493.1920, found 493.1932.

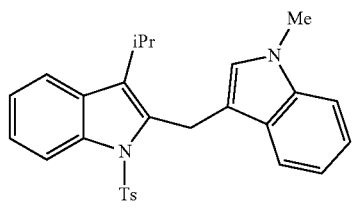

12b

Compound 12b was isolated as brown oil (38 mg, 83%). $^1$H NMR (400 MHz, CDCl$_3$, TMS): δ 8.32 (d, J=8.0 Hz, 1H), 7.67 (q, J=8.0 Hz, 2H), 7.32-7.21 (m, 6H), 7.15-7.11 (m, 1H), 6.86 (d, J=8.0 Hz, 2H), 6.18 (s, 1H), 4.54 (s, 2H), 3.49 (s, 3H), 3.22 (m, 1H), 2.25 (s, 3H), 1.36 (s, 3H), 1.34 (s, 3H). $^{13}$C NMR (100 MHz, CDCl$_3$): δ 144.0, 137.7, 137.2, 136.5, 134.1, 129.23, 129.17, 127.6, 127.4, 126.9, 126.6, 124.0, 123.0, 121.8, 120.6, 119.2, 119.1, 115.7, 112.8, 109.2, 32.7, 26.3, 22.5, 21.9, 21.7. IR (neat) ν 2969, 2936, 2875, 1722, 1679, 1612. HRMS (ESI) m/z calcd for C$_{28}$H$_{28}$N$_2$O$_2$S (M+Na)$^+$ 479.1764, found 479.1770.

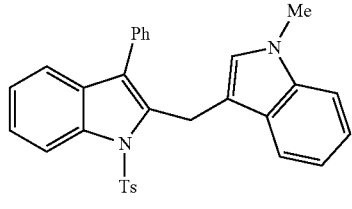

12c

Compound 12c was isolated as colorless oil (21 mg, 42%). $^1$H NMR (500 MHz, CDCl$_3$, TMS): δ 8.29 (d, J=10.0 Hz, 1H), 7.48 (d, J=5.0 Hz, 2H), 7.44-7.17 (m, 11H), 7.02 (m, 1H), 6.91 (d, J=5.0 Hz, 2H), 6.46 (s, 1H), 4.55 (s, 2H), 3.52 (s, 3H), 2.28 (s, 3H). $^{13}$C NMR (125 MHz, CDCl$_3$): δ 144.0, 137.2, 137.0, 136.4, 133.4, 130.3, 130.0, 129.3, 128.9, 127.9, 127.8, 127.6, 127.4, 126.5, 124.8, 123.8, 123.7, 121.7, 119.9, 119.3, 119.1, 115.4, 113.0, 109.1, 32.7, 22.7, 21.8. IR (neat) v 3764, 2923, 1738, 1711, 1530, 1513. HRMS (ESI) m/z calcd for $C_{31}H_{26}N_2O_2S$ (M+Na)$^+$ 513.1607, found 513.1609.

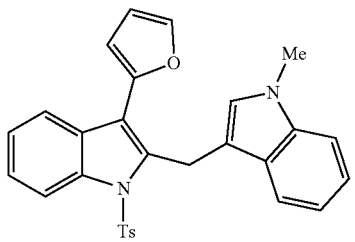

12d

Compound 12d was isolated as brown oil (29 mg, 60%). $^1$H NMR (500 MHz, CDCl$_3$, TMS): δ 8.31 (d, J=10.0 Hz, 1H), 7.94 (d, J=10.0 Hz, 1H), 7.56-7.53 (m, 2H), 7.38-7.29 (m, 4H), 7.23-7.21 (m, 2H), 7.11-7.08 (m, 1H), 6.87 (d, J=10.0 Hz, 2H), 6.48-6.43 (m, 2H), 6.38 (s, 1H), 4.74 (s, 2H), 3.51 (s, 3H), 2.24 (s, 3H). $^{13}$C NMR (125 MHz, CDCl$_3$): δ 148.4, 144.4, 142.3, 137.1, 137.0, 136.9, 136.3, 129.4, 128.3, 127.72, 127.70, 126.6, 125.0, 124.1, 121.8, 120.9, 119.3, 119.2, 115.3, 114.0, 111.7, 111.5, 109.2, 108.8, 32.7, 23.2, 21.7. IR (neat) v 3763, 2947, 1739, 1692, 1642, 1550. HRMS (ESI) m/z calcd for $C_{31}H_{24}N_2O_2S$ (M+Na)$^+$ 503.1400, found 503.1400.

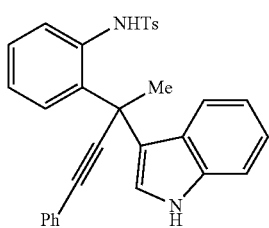

13

Compound 13 was isolated as white solid (30 mg, 63%). mp=161-163° C. $^1$H NMR (500 MHz, CDCl$_3$, TMS): δ 8.27 (s, 1H), 7.98 (s, 1H), 7.73 (d, J=10.0 Hz, 1H), 7.50-7.48 (m, 2H), 7.44 (d, J=2.5 Hz, 1H), 7.38-7.36 (m, 2H), 7.32-7.30 (m, 3H), 7.19-7.14 (m, 2H), 7.10-7.06 (m, 3H), 7.03 (d, J=5.0 Hz, 1H), 6.88-6.85 (m, 1H), 6.80 (d, J=10.0 Hz, 2H), 2.23 (s, 3H), 2.12 (s, 3H). $^{13}$C NMR (125 MHz, CDCl$_3$): δ 143.5, 137.7, 136.4, 132.1, 131.3, 129.5, 128.62, 128.60, 128.55, 127.5, 127.3, 125.0, 123.5, 123.1, 122.8, 122.2, 120.6, 120.1, 120.0, 118.4, 111.9, 92.8, 85.0, 38.1, 29.6, 21.7. IR (neat) v 2929, 2820, 1726, 1550. HRMS (ESI) m/z calcd for $C_{31}H_{26}N_2O_2S$ (M+Na)$^+$ 513.1607, found 513.1609. X-ray structure (CCDC 1016688).

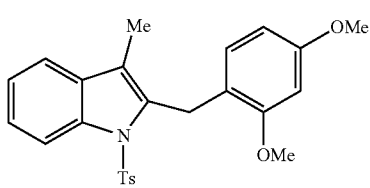

14

Compound 14 was isolated as colorless oil (14 mg, 64%). $^1$H NMR (400 MHz, CDCl$_3$, TMS): δ 8.23 (d, J=8.0 Hz, 1H), 7.47 (d, J=8.0 Hz, 2H), 7.43 (d, J=8.0 Hz, 1H), 7.33-7.24 (m, 2H), 7.04 (d, J=8.0 Hz, 2H), 6.51 (d, J=8.0 Hz, 1H), 6.46 (d, J=4.0 Hz, 1H), 6.18 (dd, J=8.0, 4.0 Hz, 1H), 4.32 (s, 2H), 3.88 (s, 3H), 3.75 (s, 3H), 2.28 (s, 3H), 2.11 (s, 3H). $^{13}$C NMR (125 MHz, CDCl$_3$): δ 159.5, 158.0, 144.4, 137.0, 136.4, 134.7, 131.5, 129.7, 129.0, 126.7, 124.4, 123.5, 119.9, 118.7, 115.4, 110.0, 104.0, 98.6, 55.8, 55.6, 25.1, 21.8, 9.2. IR (neat) v 3763, 2941, 2839, 1613, 1589, 1505. HRMS (ESI) m/z calcd for $C_{25}H_{25}NO_4S$ (M+Na)$^+$ 458.1397, found 458.1396.

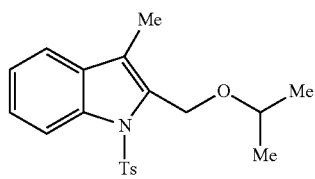

15

Compound 15 was isolated as colorless oil (17 mg, 48%). $^1$H NMR (400 MHz, CDCl$_3$, TMS): δ 8.09 (d, J=8.0 Hz, 1H), 7.88 (d, J=8.0 Hz, 2H), 7.43 (d, J=8.0 Hz, 1H), 7.31-7.27 (m, 1H), 7.24-7.20 (m, 1H), 7.15 (d, J=8.0 Hz, 2H), 4.86 (s, 2H), 3.82 (m, 1H), 2.31 (s, 3H), 2.27 (s, 3H), 1.24 (s, 3H), 1.22 (s, 3H). $^{13}$C NMR (100 MHz, CDCl$_3$): δ 144.5, 136.5, 133.4, 130.8, 129.7, 127.4, 125.3, 123.4, 120.3, 119.4, 115.1, 71.8, 60.0, 22.3, 21.8, 9.3. IR (neat) v 2941, 2839, 1613, 1589, 1505. HRMS (ESI) m/z calcd for $C_{20}H_{23}NO_3S$ (M+Na)$^+$ 380.1291, found 380.1292.

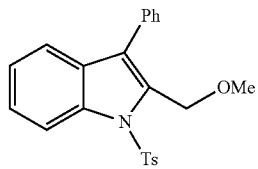

16

Compound 16 was isolated as colorless oil (24 mg, 62%). $^1$H NMR (500 MHz, CDCl$_3$, TMS): δ 8.20 (d, J=10.0 Hz, 1H), 7.96 (d, J=10.0 Hz, 2H), 7.50-7.45 (m, 5H), 7.42-7.39 (m, 1H), 7.37-7.33 (m, 1H), 7.23-7.19 (m, 3H), 4.73 (s, 2H), 3.36 (s, 3H), 2.33 (s, 3H). $^{13}$C NMR (125 MHz, CDCl$_3$): δ 144.8, 136.5, 136.4, 133.1, 132.7, 130.4, 129.8, 129.3, 128.9, 128.1, 127.5, 126.7, 125.7, 123.8, 120.6, 115.1, 64.6, 58.1, 21.8. The spectra of compound 16 are in accordance with literature. Kothandaraman, P.; Rao, W.; Foo, S. J.; Chan, P. W. H. *Angew. Chem. Int. Ed.* 2010, 49, 4619.

6. Biological Activity:

Glucagon-like peptide 1 (GLP-1) is derived from transcription of the proglucagon gene followed by posttranslational modifications of proglucagon to the following biologically active peptides: GLP-1 {7-37} and GLP-1 (7-36) NH2. GLP-1 secretion by ileal L cells is dependent on the presence of nutrients in the lumen of the small intestine. GLP-1 is a potent anti-hyperglycemic hormone inducing glucose-dependent insulin secretion and suppressing glucagon secretion. The glucose dependency of this mechanism is particularly important because GLP-1 does not stimulate insulin secretion and cause hypoglycemia when plasma glucose concentrations are in the normal fasting range.

The GLP-1 secretion assay identifies compounds that stimulate secretion of glucagonlikepeptide one (GLP-1) in mouse and human cell lines derived from gastrointestinal tract tissue. GLP-1 secretion is measured using an ELISA designed to detect the appropriate forms of GLP-1 secreted from these cells. If active in the cell-based GLP-1 assay, molecules can be further tested for selectivity in assays that measure activation of G-protein-coupled receptors (GPCRs) known to stimulate GLP-1 secretion. See, for example, "Glucagon-Like Peptide 1-Based Therapies for Type 2 Diabetes: A Focus on Exenatide," Kathleen Dungan and John B. Buse; *Clinical Diabetes* 29 (1), (Winter 2011); and "Glucagon-Like Peptide 1 Secretion by the L-Cell," Gareth E. Kim and Patricia L. Brubaker; *Diabetes:* 55 (supplement 2), (December, 2006).

Proprotein convertase subtilisin kexin type 9 (PCSK9) belongs to the proteinase K subfamily of secretory proteases. This protein plays a major regulatory role in cholesterol homeostasis. PCSK9 regulates plasma LDL-cholesterol (LDL-C) levels by directing LDL receptor (LDLR) to lysosomal degradation, resulting in reduced LDL clearance and accumulation of LDL in the circulation. Gain of function mutations of PCSK9 lead to hyperlipidemia and premature coronary artery disease (CAD) in humans, whereas loss of function mutations of PCSK9 are associated with lower levels of LDL and protection from CAD.

PCSK9 expression is actively regulated at transcription levels. Statins are known to stimulate PCSK9 transcription which in turn curbs the efficacy of statins in LDL lowering in humans. A few other molecules including berberine and oncostatin have been shown to suppress PCSK9 transcription which in turn contributes to the hypolipidemic effects of these agents. The PCSK9 SI phenotypic assay is designed to identify compounds that inhibit synthesis of PCSK9 in human hepatoma cell lines (HepG2). See, for example, Horton, J. D., Cohen, J. C., and Hobbs, H. H., "PCSK9: a convertase that coordinates LDL catabolism," *J. Lipid Res.* 50 Suppl, S172-177, (2009); Crunkhorn, S. "Trial watch: PCSK9 antibody reduces LDL cholesterol," *Nat Rev Drug Discov* 11, 11, (2012); Vogel, R. A., "PCSK9 inhibition: the next statin," *J Am Coll Cardiol* 59, 2354-2355, (2012); Li, H., Dong, B., Park, S. W., Lee, H. S., Chen, W., and Liu, J., "Hepatocyte nuclear factor 1alpha plays a critical role in PCSK9 gene transcription and regulation by the natural hypocholesterolemic compound berberine," *J Biol Chem* 284, 28885-28895, (2009); and Cao, A., Wu, M., Li, H., and Liu, J., "Janus Kinase activation by cytokine oncostatin M decreases PCSK9 expression in liver cells," *J Lipid Res* 52, 518-530, (2011).

The IL-17 pathway plays an essential pathological role in many autoimmune diseases including arthritis, multiple sclerosis, psoriasis, and inflammatory bowel disease. IL-17 is produced and secreted by at least two classes of lymphocytes, δγ and CD4+ T cells (Th17). The orphan nuclear receptor RORg is required for the differentiation of Th17 cells where over-expression in human and rodent T cells induces transcripts found in Th17 cells encoding key cytokines for the IL23 receptor and chemokines for the CCR6 receptor. In addition to RORg, recent global analysis of transcription factors has highlighted the molecular complexity of the Th17 differentiation program.

The IL-17 phenotypic assay seeks to identify inhibitors of IL-17 secretion from human peripheral blood mononuclear cells (PBMCs) following stimulation of memory T cells by IL-23, anti-CD3, and anti-CD28. Compounds of interest will inhibit IL-17. See W. Ouyang, J. K. Kolls, V. Zheng, "The biological functions of T helper 17 cell effector cytokines in inflammation," *Immunity*, 28, 454-467 (2008); I. I. Ivanov, L. Zhou, D. R. Littman, "Transcriptional regulation of Th17 cell differentiation," *Semin Immunol*, 19, 409-417 (2007); N. Manel, D. Unutmaz, D. R. Littman, "The differentiation of human T(H)-17 cells requires transforming growth factor-beta and induction of the nuclear receptor RORgammat," *Nat Immunol*, 9, 641-649 (2008); and M. Ciofani, A. Madar, C. Galan, M. Sellars, K. Mace, F. Pauli, A. Agarwal, W. Huang, C. N. Parkurst, M. Muratet, K. M. Newberry, S. Meadows, A. Greenfield, V. Vang, P. Jain, F. K. Kirigin, C. Birchmeier, E. F. Wagner, K. M. Murphy, R. M. Myers, R. Bonneau, D. R. Littman, "A validated regulatory network for Th17 cell specification." *Cell*, 151, 289-303 (2012).

(6.1) GLP-1 mSTC Assay:

(6.1.1) Materials:

The mouse enteroendocrine-like STC-1 cell line is described in (*Am. J. Pathol.* 1990 June; 136(6):1349-63. Rindi G, Grant S G, Yiangou Y, Ghatei M A, Bloom S R, Bautch V L, Solcia E, Polak J M.). The GLP-1 peptide used as standards in the "AlphaLISA"®-brand assay ("AlphaLISA" is a registered trademark of PerkinElmer.): 7-37 was purchased from Bachem, Inc., Redwood City, Calif., USA (catalog no. H67950). Bovine serum albumin was purchased from MP Biomedicals, LLC (Santa Ana, Calif., USA; catalog no. #15240). Plates for cell growth were purchased from Greiner Bio-One North America, Inc. (Monroe, N.C., USA) and the Proxi-plates plus for reading the AlphaLISA were from Perkin Elmer.

(6.1.2) Cell Culture Conditions:

STC-1 cells were grown adherently at 37° C. in a humidified incubator at 5% CO2 using DMEM (with high glucose and L-glutamine; Hyclone, a division of GE Life Sciences; Logan, Utah, USA) containing 10% US Certified heat inactivated fetal bovine serum (Invitrogen, a division of Thermo Fisher Scientific Inc., Grand Island, N.Y., USA), 10 mM HEPES (Invitrogen), and anti-biotic/anti mycotic (Invitrogen) for cell maintenance. For GLP-1 secretion experiments cells were plated at 12,000 per well in 80 µl of media on poly-D-lysine 384 well plates black with clear bottom (Greiner).

(6.1.3) GLP-1 Secretion Studies:

On the day of the assay the cells are washed three times with 80 µl/well HBSS plus 0.1% BSA using a plate washer (BioTech). 50 ul per well HBSS plus 0.1% BSA is added to cells and then 100 nl of compound is dispensed onto cells (PinTool, V&P Scientific, Inc., San Diego, Calif., USA). Cells were treated with compound at a starting concentration of 40 uM with a 2-fold serial dilution for a dose response. Cells were incubated with compound for 2 hours at 37° C. GLP-1 in supernatants was quantified using a homogenous "AlphaLISA"®-brand assay in a 384-well format. Samples were read on an Envision photometer (Perkin Elmer) and the assay was calibrated to synthetic GLP-1 peptide.

(6.1.4) Data Processing and Statistical Analysis:

For single point activity the % stimulation is calculated based on normalizing the GLP-1 secreted to a compound which produces a robust and reproducible response of GLP-1 secretion in the mSTC cells.

Percent stimulation and percent inhibition were calculated by Equation 1 and Equation 2, respectively, using the Maximum (Max) and Minimum (Min) response conditions for each assay.

$$\text{Stimulation (\%)} = \frac{\text{Signal} - \text{Min}}{\text{Max} - \text{Min}} * 100 \qquad \text{Equation 1}$$

$$\text{Inhibition (\%)} = \left(1 - \frac{\text{Signal} - \text{Min}}{\text{Max} - \text{Min}}\right) * 100 \qquad \text{Equation 2}$$

The EC50 or IC50 of test compounds was determined by fitting the calculated percent activation or inhibition values using a standard 4 parameter logistic and non-linear regression analysis.

(6.2) GLP-1 NCI Assay (6.2.1) Materials:

NCI-H716 cells (ATCC, CCL-251) were obtained from the American Type Culture Collection (Manassas, Va., USA). Cells were grown at 37° C., in a humidified incubator at 5% CO2 unless otherwise noted. Cell Culture reagents were purchased from either HyClone or Invitrogen. The GLP-1 peptides used as standards in the "AlphaLISA"®-brand assay; 7-36 and 7-37 were purchased from BACHEM (H9560 and H67950). BSA is purchased from MP (#15240). DPP-IV inhibitor was purchased from Millipore (Waltham, Mass., USA; catalog no. DDP4-010). Plates for cell growth were purchased from Greiner and the Proxi-plates plus for reading the "AlphaLISA"®-brand assay were from Perkin Elmer™.

(6.2.2) Cell Culture Conditions:

Human NCI-H716 cells were grown in suspension at 37° C., in a humidified incubator at 5% CO2 in RPMI 1640 medium (Invitrogen) supplemented with 10% US Certified heat inactivated FBS (Invitrogen), 2 mM L-glutamine (Invitrogen), 10 mM HEPES (Hyclone) and Anti Biotic/Anti Mycotic (Hyclone) for cell maintenance. The cells were then grown in a "differentiation" media prior to being tested for GLP-1 secretion. The "differentiation" media was comprised of DMED High Modified (Hi-glucose, +L-glu, –Phenol Red), 10 mM HEPES, 10% US Certified heat inactivated FBS (HyClone), and Anti Biotic/Anti Mycotic (Hyclone). For GLP-1 secretion experiments cells were seeded on poly-D-lysine 384 well plates black with clear bottom (Greiner).

(6.2.3) GLP-1 Secretion Studies in NCI-H716 Cells:

Human NCI-H716 cells were grown in "differentiation" media prior to being used in the assay for GLP-1 secretion. On the day of the assay the cells are washed twice in HBSS plus 0.1% BSA plus 1% DPPIV Inhibitor and re-suspended in HBSS plus 0.1% BSA plus 1% DPP-IV Inhibitor. Cells were seeded at 10,000 cells per well in 384 well PD plates in 50 ul per well. Cells were treated with compound at a starting concentration of 40 uM with a 3 fold serial dilution for a dose response. Cells were incubated with compound for 2 hours at 37° C. GLP-1 in supernatants was quantified using a homogenous "AlphaLISA"®-brand assay in a 384-well format. Samples were read on an Envision (Perkin Elmer and the assay was calibrated to synthetic GLP-1 peptides.

(6.2.4) Data Processing and Statistical Analysis:

For single point activity the % stimulation is calculated based on normalizing the GLP-1 secreted to a compound which produces a maximum response of GLP-1 secretion in the NCI cells.

Percent stimulation and percent inhibition were calculated by Equation 1 and Equation 2, respectively, using the Maximum (Max) and Minimum (Min) response conditions for each assay (Supplementary Information).

$$\text{Stimulation (\%)} = \frac{\text{Signal} - \text{Min}}{\text{Max} - \text{Min}} * 100 \qquad \text{Equaton 1}$$

$$\text{Inhibition (\%)} = \left(1 - \frac{\text{Signal} - \text{Min}}{\text{Max} - \text{Min}}\right) * 100 \qquad \text{Equaton 2}$$

The EC50 or IC50 of test compounds was determined by fitting the calculated percent activation or inhibition values using a standard 4 parameter logistic and non-linear regression analysis.

(6.3) PCSK9 Inhibition Assay:

Inhibition of secreted PCSK9 was measured in human hepatocellular carcinoma (HepG2) cells using an "AlphaLISA"®-brand assay. Given that this assay is run in an inhibition mode, the viability of cells was also assessed to rule out compounds whose PCSK9 inhibition resulted from deleterious effects on cell health. Freshly cultured HepG2 cells were harvested from poly-d-lysine-coated T225 cell culture flasks and plated in biocoat poly-d-lysine coated 384 black with clear bottom microtiter plates (BD BioCoat #356663; Becton, Dickinson and Company, Franklin Lakes, N.J., USA) at 20,000 cells/well in 60 ul of growth media (MEM+10% heat inactivated FBS+1% NEAA+1% sodium pyruvate+1% GlutaMAX). Cell plates were incubated overnight at 37° C. and 5% CO2 prior to compound treatment.

Compounds were serially diluted 3-fold in 100% DMSO to achieve a starting final assay plate concentration of 50 uM following a 20-fold dilution in assay media (MEM+5% heat inactivated FBS+1% NEAA+1% sodium pyruvate+1% GlutaMAX) and a 10-fold dilution into the cell plates. While the compounds were diluting, the cell plates were washed twice with 75 ul of assay media and refilled with 45 ul of assay media. The cell plates were incubated for 48 hrs at 37° C. and 5% $CO_2$ prior to running the "AlphaLISA"®-brand assay. The "AlphaLISA"® bead mix was assembled in water and left to incubate 1 hr in the dark prior to use (1×"AlphaLISA"® buffer, 5 mg/ml mAb-PCSK9-A4 conjugated acceptor beads, 3.4 uM bioti-mAb-anti-PCSK9-B9, 5 mg/ml streptavidin-coated donor beads). Following the cell incubation, 15 ul of supernatant was transferred from the cell plates to 384 ProxiPlates. 15 ul of warm assay media was immediately added back to the cell plates. In the dark, 5 ul of the bead mix was added to the ProxiPlates, and then the plates were left to incubate at ambient temperature in the dark overnight before being read on an Envision (excitation 680 nm and emission 615 nm). 10 ul of stain (serum-free MEM, Hoechst stain, propidium iodide) was added to the cell plates followed by an incubation at 37° C. and 5% $CO_2$ for 3 hours. The plates were removed from the incubator, sealed with black tape, and read for propidium iodide stained nuclei using an Acumen-brand cell imaging system (TTP Labtech Ltd., Melbourn, Hertfordshire United Kingdom). Percent inhibitions at all concentrations tested were calculated relative to 0.5% DMSO (min effect), and the effect of 50 uM of a fully efficacious PCSK9 inhibitor for the PCSK9 inhibition assay (max effect), or 50 uM Brefeldin A for the viability assay (max effect). IC50 values were calculated using a 4 parameter logistic curve fitting equation.

In order to rule out compounds that nonspecifically inhibit secretion of proteins, a Metridia luciferase (24 kDa protein containing an N-terminal secretory signal peptide) assay was conducted in HepG2 cells. Freshly cultured HepG2 cells stably transfected with Metridia luciferase were harvested from poly-d-lysine coated T225 cell culture flasks and plated in 384 well, black, clear bottom, poly-d-lysine coated plates at 20,000 cells/well in 60 ul of assay media (MEM+10% heat inactivated FBS+2% NEAA+2% sodium pyruvate+1% GlutaMAX+2% penicillin streptomycin+2% G418). The compounds of interest were dosed as previously described excluding the washing of cells.

The cell plates were incubated at 37° C. and 5% CO2 for 5 hours. Next, 15 ul of the supernatant was added to 384-well Perkin Elmer Optiplates. The plates were then incubated at ambient temperature for 10 minutes and the luciferase signal was quantified on an Envision-brand photometer (Perkin Elmer). Percent inhibitions at all concentrations tested were calculated relative to 0.5% DMSO (min effect) and the effect of 50 uM Brefeldin A (max effect). $IC_{50}$ values were calculated using a 4 parameter logistic curve fitting equation.

7. Representative Procedure for the Formation of Diindolylmethane and Removing of Boc-Protecting Group:

To a vial under argon atmosphere containing propargyl ether 7 (0.38 mmol, 100 mg) in dioxane (0.2 M) was added 5-chloroindole (0.76 mmol, 117 mg), platinum dichloride (10 mol %, 10 mg), and sodium bicarbonate (0.57 mmol, 61 mg). The reaction was stirred at 100° C. overnight. The crude mixture was filtered and washed with ethyl acetate. The volatiles were removed under reduced pressure. The crude mixture was then heated to 160° C. for 2 h. The product was purified by flash column chromatography eluting with 5:1 hexanes/ethyl acetate to give an off-white solid 10a (56 mg, 52% yield, m.p.=140-143° C.).

8. Representative Procedure for the Formylation Reaction:

To a round bottom flask under argon atmosphere containing N,N-dimethylformamide (0.2 M, 0.5 ml) at 0° C., was added phosphoryl chloride (0.12 mmol, 11 ul). The mixture was allowed to stir for 15 min. Diindolylmethane 10a (0.1 mmol, 30 mg) was dissolved in minimal DMF and the solution was added dropwise to the reaction mixture at 0° C. the reaction was warmed to room temperature and allowed to stir for 6 h.

The crude reaction mixture was poured into a separatory funnel containing saturated sodium bicarbonate solution. The products were extracted 4× with diethyl ether and washed with 0.1M sodium hydroxide. The organic phase was collected and all volatiles were removed under reduced pressure. The product was purified by flash column chromatography eluting with 3:1 hexanes/ethyl acetate to give a bright orange solid 11a (18 mg, 55% yield, m.p.=162-163° C.).

9. Representative Procedure for the Biological Assay:

The human Hep G2 cell line from the Small Molecule Screening and Synthesis Facility (UWCCC, Madison, Wis.) and was maintained in DMEM medium supplemented with 10% FBS. Cells were incubated at 37° C. in a humidified atmosphere supplemented with 5% $CO_2$.

Preparation of cells: Cells were cleaved from T75 flasks with 0.05% trypsin. The cells were then collected by spinning at 1 g for 4 min. Excess media containing trypsin was removed from the pellet, which was then re-suspended in growth media. The cells were then counted using a hemocytometer. Cells were plated in sterile 96-well clear bottom black culture plates at a density of 20,000 cells per well in 0.1 mL of media. The cells were then incubated for 24 h at 37° C. in a humidified atmosphere supplemented with 5% $CO_2$.

The ethoxyresorufin-O-deethylase (EROD) assay was performed on cell cultures of human Hep G2 cells. Briefly, 24 h after plating, cells in 96-well plates were treated with AhR agonists and allowed to incubate for 24 h. Each well was then rinsed with 200 uL of PBS buffer twice. To each well was then added 100 uL of 150 nM solution of 7-ethoxyresurufin and allowed to incubate for 2 h. Fluorescence measurements were obtained with a Safire II micro plate reader with excitation at 520 nm with a 25 nm bandwidth and emission at 595 nm with a 20 nm bandwidth.

10. Characterization Data for New Compounds:

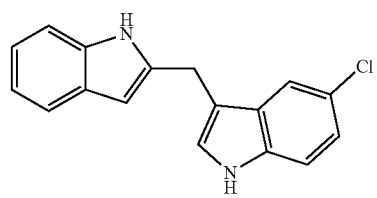 [SMILES: Clc1ccc2[nH]cc(Cc3cc4ccccc4[nH]3)c2c1]

10a $^1$H NMR (400 MHz, $CDCl_3$): δ 4.23 (s, 2H), 6.37 (s, 1H), 7.04-7.12 (m, 3H), 7.16 (dd, J=8.4, 2 Hz, 1H), 7.21-7.24 (m, 1H), 7.29 (d, J=8.8 Hz, 1H), 7.51 (d, J=2 Hz, 1H), 7.53-7.56 (m, 1H), 7.83 (s, 1H), 8.04 (s, 1H); $^{13}$C NMR (100 MHz, $CDCl_3$) δ 137.85, 136.21, 134.96, 129.04, 128.59, 125.75, 124.16, 122.99, 121.38, 120.18, 119.90, 118.69, 113.01, 112.43, 110.67, 100.57, 24.58. IR (neat) 670.07, 734.21, 798.73, 1160.22, 1454.79, 1729.59, 2852.67, 3414.90 $cm^{-1}$. HRMS (ESI) M/Z calcd. for $C_{17}H_{13}ClN_2$ $(M+H)^+$ 281.0841 found: 281.0841.

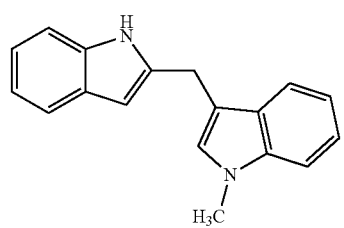 [SMILES: Cn1cc(Cc2cc3ccccc3[nH]2)c2ccccc21]

10d

Pale yellow solid (m.p.=185-188° C.), 74 mg, 70% yield.

$^1$H NMR (400 MHz, acetone): δ 3.68 (s, 3H), 4.21 (s, 2H), 6.24 (s, 1H), 6.72 (dd, J=8.8, 2.4 Hz, 1H), 6.87-6.97 (m, 2H), 6.99 (d, J=2.4 Hz, 1H), 7.14 (s, 1H), 7.22-7.28 (m, 2H) 7.40 (d, J=8.8, 1H), 9.89 (s, 2H) $^{13}$C NMR (100 MHz, acetone): δ 153.97, 139.58, 136.86, 132.21, 129.26, 128.12, 124.00, 120.40, 119.51, 118.95, 112.43, 112.05, 111.60, 110.74, 100.79, 99.54, 55.12, 24.40.6 IR (acetone) 747.49, 790.29, 890.19, 1025.00, 1168.98, 1214.05, 1455.68, 1694.21, 2360.77, 3397.12 v $cm^{-1}$. HRMS (ESI) M/Z calcd. for $C_{18}H_{16}N_2O$ $(M+H)^+$ 277.1336 found: 277.1324.

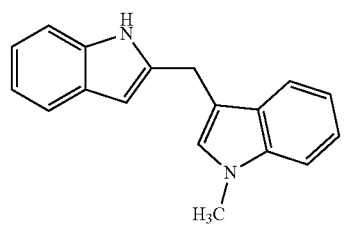

10d

Orange oil, 65 mg, 67% yield.

$^1$H NMR (400 MHz, $CDCl_3$): δ 3.74 (s, 3H), 4.26 (s, 2H), 6.38 (s, 1H), 6.91 (s, 1H), 7.04-7.09 (m, 3H), 7.15-7.18 (m, 1H) 7.21-7.25 (m, 1H), 7.33 (d, J=8.00 Hz, 1H), 7.49-7.55 (m, 2H) 7.83 (s, 1H); $^{13}$C NMR ($CDCl_3$, 100 MHz): δ 138.59, 137.32, 136.05, 129.03, 127.83, 127.56, 122.02, 121.07, 119.97, 119.68, 119.33, 119.20, 111.31, 110.59, 109.43, 100.10, 32.82, 24.51. IR (neat) 737.42, 779.57, 908.07, 1011.12 1292.42, 1372.54, 1472.64, 3400.12 $cm^{-1}$.

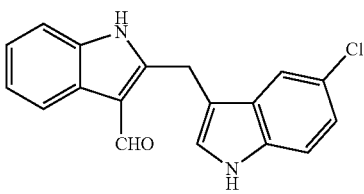

11a

¹H NMR (400 MHz, d6-acetone): δ 4.74 (s, 2H), 7.13-7.18 (m, 1H), 7.18-7.23 (m, 2H), 7.32-7.39 (m, 2H), 7.49 (s, 1H), 7.71 (s, 1H), 8.23 (s, 1H), 9.27 (s, 1H), 10.42 (s, 1H), 11.02 (s, 1H). ¹³C NMR (100 MHz, d6-acetone) δ 184.06, 150.03, 135.96, 131.96, 129.31, 125.39, 123.51, 123.02, 122.18, 121.36, 120.80, 120.28, 117.75, 116.59, 114.16, 112.42, 111.58, 22.31. IR (neat) 747.35, 795.21, 1227.57, 1382.07, 1634.18, 1706.07, 2360.11, 2921.17, 3260.71 cm⁻¹. HRMS (ESI) M/Z calcd. for $C_{18}H_{13}ClN_2O$ (M+H)⁺ 309.0790, found: 309.0783.

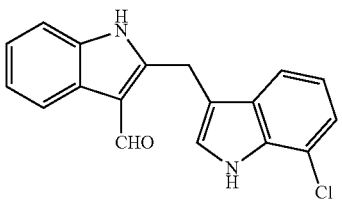

11b

Pale orange solid, m.p.=170-172° C., 19 mg, 52% yield.

¹H NMR (400 MHz, d6-acetone): δ 4.73 (s, 2H), 7.00 (t, J=7.6 Hz, 1H), 7.13-7.20 (m, 3H), 7.30-7.34 (m, 1H), 7.45 (s, 1H), 7.49 (d, J=8.0 Hz, 1H) 8.21 (d, J=6.4 Hz, 1H), 10.42 (s, 1H), 10.55 (s, 1H), 10.85 (s, 1H) ¹³C NMR (CDCl₃, 100 MHz): δ 184.59, 148.48, 134.92, 134.03, 128.50, 126.69, 124.25, 123.64, 123.05, 122.47, 121.37, 120.87, 117.56, 117.27, 114.24, 111.52, 111.23, 23.13. IR (neat) 731.76, 907.67, 1382.91, 1457.99, 1635.54, 2925.03, 3265.54 cm⁻¹. HRMS (ESI) M/Z calcd. for $C_{18}H_{13}ClN_2O$ (M+H)⁺ 309.0790, found: 309.0789.

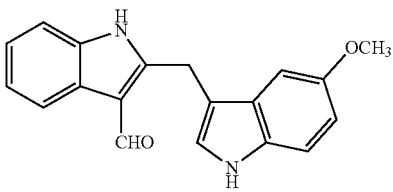

11c

Pale yellow solid, decomposed at 183° C., 15 mg, 53% yield.

¹H NMR (400 MHz, d6-acetone): 3.65 (s, 3H), 4.57 (s, 2H), 6.87 (d, J=8.6, 1H), 7.03-7.11 (m, 3H), 7.230 (d, J=7.5 Hz, 1H), 7.47 (s, 1H), 8.08 (s, 2H), 9.05 (s, 1H), 10.27 (s, 1H), 10.88 (s, 1H); ¹³C NMR (100 MHz, d6-acetone) δ 184.15, 154.26, 132.18, 124.63, 124.47, 123.25, 122.94, 122.31, 122.12, 120.81, 113.51, 112.34, 112.29, 111.97, 111.67, 111.57, 100.45, 55.28, 22.32. IR (neat) 748.59, 1228.73, 1365.64, 1466.37, 1642.24, 1708.78, 2360.38, 3003.91, 3423.55 cm⁻¹. HRMS (ESI) M/Z calcd. for $C_{19}H_{16}N_2O_2$ (M+H)⁺ 305.1285, found: 305.1284.

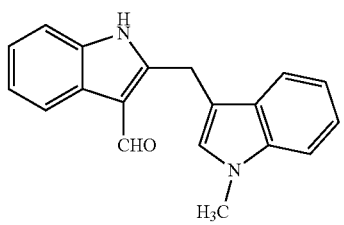

11d

Red solid, m.p.=130-131° C., 16 mg, 56% yield.

¹H NMR (400 MHz, CDCl₃): δ 3.82 (s, 3H), 4.66 (s, 2H), 7.04 (s, 1H), 7.12 (t, J=7.6 Hz, 1H), 7.17 (d, J=3.6 Hz, 2H), 7.31 (d, J=7.6 Hz, 1H) 7.38 (d, J=8 Hz, 2H), 7.47 (d, J=8.00 Hz, 1H), 8.25 (d, J=8, 1H) 8.33 (s, 1H), 10.41 (s, 1H); ¹³C NMR (125 MHz, CDCl₃) δ 184.69, 149.66, 137.56, 134.97, 128.42, 127.62, 126.78, 123.54, 123.01, 122.65, 121.02, 120.05, 119.01, 114.12, 111.27, 109.89, 108.54, 33.11, 22.91. IR (neat) 700.76, 749.62, 1222.43, 1399.13, 1465.59, 1657.61, 1712.41, 2359.57, 2821.52, 3360.22 cm⁻¹. HRMS (ESI) M/Z calcd. for $C_{19}H_{16}N_2O$ (M+H)⁺ 289.1336, found: 289.1338.

11. Pharmacological Activity:

The arylhrydrocarbon receptor (AhR) is a basic helix-loop-helix transcription factor that is well conserved across many species. Hahn, M. E. Chem. Biol. Interact. 2002, 141, 131. AhR readily binds to various endogenous and xenobiotic polyaromatic heterocycles. Denison, M. S.; Soshilov, A. A.; He, G.; DeGroot, D. E.; Zhao, B. Toxicol. Sci. 2011, 124, 1. It is perhaps best known for its role in conferring the toxicity of environmental pollutant 2,3,7,8-tetrachlorodibenzo-p-dioxin (TCDD or dioxin) 1 (see below). Bock, K. W. Biol. Chem. 2013, 394, 729. AhR binds to TCDD with remarkably high affinity and upon binding, the ligand-receptor complex travels to the nucleus where AhR then dimerizes with the aryl hydrocarbon receptor translocator (ARNT). Knutson, J. C.; Poland, A. Cell 1982, 30, 225; Poland, A.; Knutson, J. C. Annu. Rev. Pharmacol. Toxicol. 1982, 22, 517. It is this active dimer that functions to promote or repress the transcription of a multitude of different genes, most notably CYP1A1. Schmidt, J. V.; Bradfield, C. A. Annu. rev. Cell Dev. Biol. 1996, 12, 55.

AhR activation is highly regulated by a negative feedback mechanism to prevent continuous signaling. Chang, C. Y.; Puga, A. Mol. Cell Biol. 1998, 18, 525. It is believed that prolonged AhR signaling is very unfavorable. Mitchell, K. A.; Elferink, C. J. Biochem. Pharmacol. 2009, 77, 947. Therefore, it has been proposed that the toxicity of dioxin is due to its exceptionally long metabolic stability (half-life of 7-10 years in human), resulting in a continuously activated AhR. Bock, K. W. Biol. Chem. 2013, 394, 729.

It has been postulated that AhR is a target for the treatment of benign prostatic hyperplasia, (Mehta, V.; Vezina, C. M.

Differentiation 2011, 82, 211) reduction of undesired immune responses during organ transplantation, (Van Voorhis, M.; Fechner, J. H.; Zhang, X.; Mezrich, J. D. Transplantation 2013, 95, 983) inflammation disorders, (Beamer, C. A.; Shepherd, D. M. Semin. Immunopathol. 2013, 35, 693; Busbee, P. B.; Rouse, M.; Nagarkatti, M.; Nagarkatti, P. S. Nutrition Rev. 2013, 71, 353) and certain types of cancer. Safe, S.; Lee, S.-O.; Jin, U.-H. Toxicol. Sci. 2013, 135, 1. Peterson and Safe reported that synthetic AhR agonist 6-methyl-1,3,8-trichlorodibenzofuran (MCDF) 2 blocked vascular endothelial growth factor in prostate and conferred protection against prostate cancer in vivo. Fritz, W. A.; Lin, T.-M.; Safe, S.; Moore, R. W.; Peterson, R. E. Biochem. Pharmacol. 2009, 77, 1151. Safe also showed that a variety of substituted 3,3'-diindolylmethanes (DIMs) 3, which are also AhR agonists, inhibit tumor growth in rat models. McDougal, A.; Gupta, M. S.; Morrow, D.; Ramamoorthy, K.; Lee, J. E.; Safe, S. H. Breast Cancer Res. Treat. 2001, 66, 147. Natural products indolo[3,2-b]carbazole (ICZ) 4, 6-formylindolo[3,2-b]carbazole (FICZ) 5, and malassezin 6 have been demonstrated to be agonists of AhR. Both ICZ and FICZ are categorized as indolocarbazoles, (Knölker, H.-J.; Reddy, K. R. Chem. Rev. 2002, 102, 4303; Schmidt, A. W.; Reddy, K. R.; Knölker, H.-J. Chem. Rev. 2012, 112, 3193; Wincent, E.; Amini, N.; Luecke, S.; Glatt, H.; Bergman, J.; Crescenzi, C.; Rannug, A.; Rannug, U. J. Biol. Chem. 2009, 284, 2690) while malassezin (Wille, G.; Mayser, P.; Thoma, W.; Monsees, T.; Baumgart, A.; Schmitz, H. J.; Schrenk, D.; Polborn, K.; Steglich, W. Bioorg. Med. Chem. 2001, 9, 955; Kramer, H. J.; Podobinska, M.; Bartsch, A.; Battmann, A.; Thoma, W.; Bernd, A.; Kummer, W.; Irlinger, B.; Steglich, W.; Mayser, P. Chembiochem 2005, 6, 860) is a formylated 2,3'-diindolylmethane. Nguyen, L. P.; Bradfield, C. A. Chem. Res. Toxicol. 2008, 21, 102. Recent studies suggested that FICZ had antiasthmatic effects by inhibiting Th2 cytokine production in a mouse model. Jeong, K.-T.; Hwang, S.-J.; Oh, G.-S.; Park, J.-H. Int. *Immunopharmacol.* 2012, 13, 377. Herein we the development of selective AhR modulators by preparing an assortment of 2,3'-diindolylmethanes.

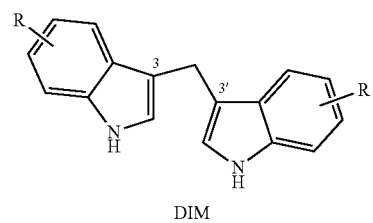

TCDD or Dioxin

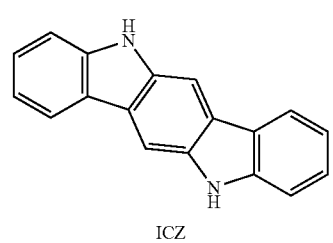

MCDF

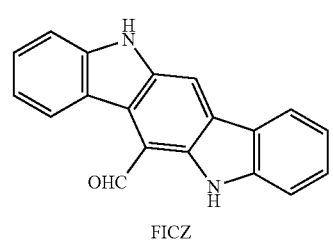

DIM

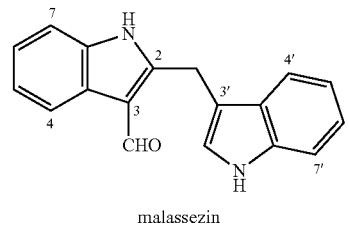

ICZ

5

FICZ

6 malassezin

The platinum-catalyzed indole annulation/arylation cascade reaction for the synthesis of diindolylmethane 9 from propargylic ether 7 is shown in Reaction Scheme 4. As described above, this route has demonstrated utility in the total synthesis of the natural product malassezin. Based on this method, a collection of malassezin analogues 10 and 11 were prepared following the sequence in Reaction Scheme 4. After the formation of 9 using the indole annulation/arylation protocol, the Boc protecting group was cleaved under thermal conditions to produce diindolylmethanes 10, which were then treated with POCl$_3$ and DMF to give the formylated malassezin analogues 11. Shu, D.; Winston-McPherson, G. N.; Song, W.; Tang, W. Org. Lett. 2013, 15, 4162.

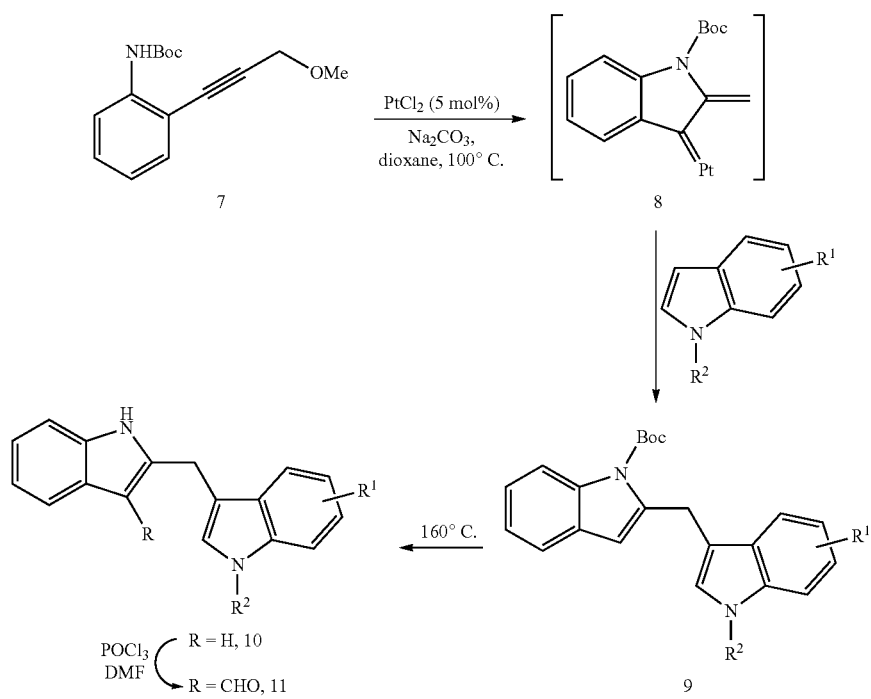

Reaction Scheme 4. Synthesis of 2,3'-Diindolylmethanes

The bioactivity of malassezin analogs was then investigated. The well-documented ethoxyresorufin-O-deethylase (EROD) assay was used to determine the $EC_{50}$ values of the compounds towards AhR activation in HepG2 cells. Donato, M. T.; Gomezlechon, M. J.; Castell, J. V. Anal. Biochem. 1993, 213, 29; van Tonder, J. J., University of Pretoria Z.A., Thesis, 2011. This assay measures the induction of cytochrome P450-1A1 (CYP1A1), which is a major outcome of AhR activation. Whyte, J. J.; Jung, R. E.; Schmitt, C. J.; Tillitt, D. E. Crit. Rev. Toxicol. 2000, 30, 347. CYP1A1 selectively converts 7-ethoxyresorufin to the fluorescent product resorufin.

Malassezin served as the positive control (Table 4). The $EC_{50}$ values of the malassezin analogs varied quite dramatically depending on their respective substitution pattern. For the halogenated 2,3'-diindolylmethanes 11a-c, 5'-chlorination resulted in a compound (11a) more potent than the positive control, while 7'-chlorination gave a slightly weaker agonist (11b). Compound 11c, with a methoxy substitution on the 5'-position, behaved similarly to malassezin. Interestingly, compound 11d with an N-methyl group on the 1'-position was surprisingly potent; its $EC_{50}$ value was about five times lower than that of malassezin.

The importance of the formyl group in malassezin analogues for AhR activation was also investigated. In the case of compound pair 10a/11a, the formyl group contributed significantly to the potency of 11a. In contrast, other non-formylated compounds including 6', 10c, and 10d have similar potency as their formylated counterparts (6, 11c, and 11d).

Up to 12-fold increase of signal over DMSO treatment was observed for many of the malassezing analogs. Even at 10 nM concentration, compounds 11a and 11d could induce 5- and 6-fold increase of signals, respectively (data not shown).

TABLE 4

AhR Activity of Diindolylmethanes

| Compounds | | $EC_{50}$ (μM) |
|---|---|---|
| 6 | | 0.27 ± 0.1 |
| 11a | | 0.093 ± 0.15 |
| 11b | | 0.32 ± 0.1 |
| 11c | | 0.23 ± 0.1 |

TABLE 4-continued

AhR Activity of Diindolylmethanes

| Compounds | | $EC_{50}$ (μM) |
|---|---|---|
| 11d | (structure: 2-((1-methyl-1H-indol-3-yl)methyl)-1H-indole-3-carbaldehyde) | 0.055 ± 0.03 |
| 6' | (structure: 2-(1H-indol-3-ylmethyl)-1H-indole) | 0.215 ± 0.46 |
| 10a | (structure: 5-chloro-3-((1H-indol-2-yl)methyl)-1H-indole) | >6.7 |
| 10c | (structure: 5-methoxy-3-((1H-indol-2-yl)methyl)-1H-indole) | 0.094 ± 0.27 |
| 10d | (structure: 3-((1-methyl-1H-indol-3-yl)methyl)-1H-indole) | 0.086 ± 0.04 |

Selected compounds were also tested for their ability to induce glucagon-like peptide 1 (GLP-1) in standard in vivo testing. Glucagon-like peptide 1 (GLP-1) is derived from transcription of the proglucagon gene followed by post-translational modifications of proglucagon to the following biologically active peptides: GLP-1 (7-37) and GLP-1 (7-36) NH2. GLP-1 secretion by ileal L cells is dependent on the presence of nutrients in the lumen of the small intestine. GLP-1 is a potent anti-hyperglycemic hormone inducing glucose-dependent insulin secretion and suppressing glucagon secretion. The glucose dependency of this mechanism is particularly important because GLP-1 does not stimulate insulin secretion and cause hypoglycemia when plasma glucose concentrations are in the normal fasting range.

The GLP-1 secretion, diabetes phenotypic testing identifies compounds that stimulate secretion of glucagon-like peptide one (GLP-1) in mouse and human cell lines derived from gastrointestinal tract tissue. GLP-1 secretion is measured using an Eli Lilly & Company (Indianapolis, Ind., USA) proprietary ELISA assay that was specifically designed to detect the appropriate forms of GLP-1 secreted from these cells. (Eli Lilly operates a program known Open Innovation Drug Discovery that performs such testing. See https://openinnovation.lilly.com/dd/.) If active in the cell-based GLP-1 assay, molecules are further tested for selectivity in assays that measure activation of GPCRs known to stimulate GLP-1 secretion. See Glucagon-Like Peptide 1-Based Therapies for Type 2 Diabetes: A Focus on Exenatide; Kathleen Dungan and John B. Buse; Clinical Diabetes: 29 (1), (Winter 2011); and Glucagon-Like Peptide 1 Secretion by the L-Cell; Gareth E. Kim and Patricia L. Brubaker; Diabetes: 55 (supplement 2), (December, 2006).

The compounds were also tested for their inhibitory activity against proprotein convertase subtilisin/kexin type 9 (PCSK9). PCSK9 plays a major regulatory role in cholesterol homeostasis, and thus is an important drug target for treating hypercholesterolemia. See, for example, Steinberg D, Witztum J L (June 2009). "Inhibition of PCSK9: a powerful weapon for achieving ideal LDL cholesterol levels". Proc. Natl. Acad. Sci. U.S.A. 106 (24): 9546-7. The results are shown in Table 5.

TABLE 5

PCSK9 and GLP-1 Activity.

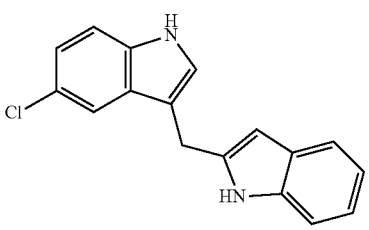

2351377819
PCSK9, IC50 = 10 uM
GLP-1, EC50 = 14.8 uM

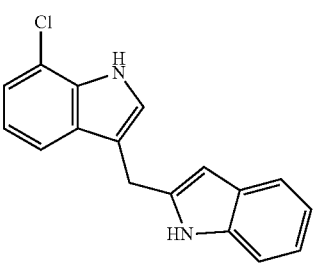

2351377820
PCSK9, IC50 = 2.8 uM
GLP-1, EC50 = 7.2 uM

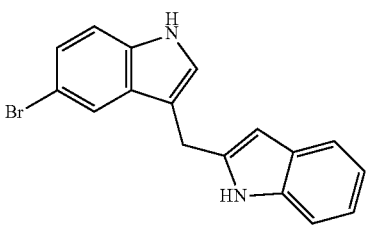

2351377823
GLP-1, EC50 = 6.8 uM

TABLE 5-continued

PCSK9 and GLP-1 Activity.

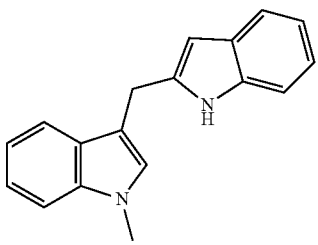

2351377824
PCSK9, IC50 = 17.9 uM
(AhR, EC50 = 0.09 uM)

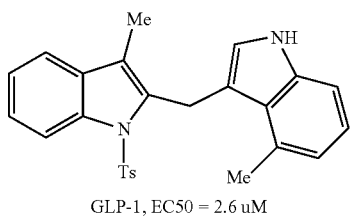 [SMILES: Cc1ccc(S(=O)(=O)n2c(Cc3c[nH]c4cccc(C)c34)c(C)c3ccccc32)cc1]

GLP-1, EC50 = 2.6 uM

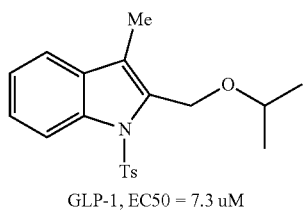 [SMILES: Cc1ccc(S(=O)(=O)n2c(COC(C)C)c(C)c3ccccc32)cc1]

GLP-1, EC50 = 7.3 uM

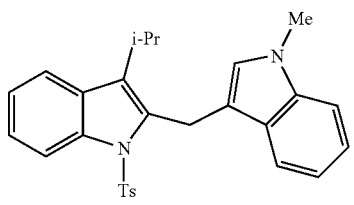

PCSK9, IC50 = 1.1 uM

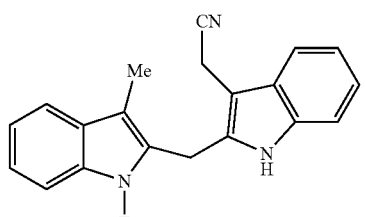

IL17, IC50 = 3.1 uM
IL5, IC50 > 30 uM

TABLE 5-continued

PCSK9 and GLP-1 Activity.

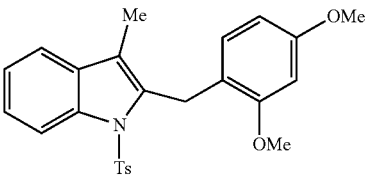

PCSK9, IC50 = 1.1 uM
GLP-1, EC50 = 2.9 uM

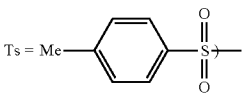

These examples demonstrate the utility of the disclosed compounds to treat ailments in mammals that are mediated by the arylhydrocarbon receptor, GLP-1, and/or PCSK9.

12. X-Ray Crystallography Studies:

(12.1) Structural Report on Compound 9b (12.1.1) Data Collection:

A colorless crystal with approximate dimensions 0.56× 0.48×0.41 mm$^3$ was selected under oil under ambient conditions and attached to the tip of a MiTeGen MicroMount (MiTeGen, LLC, Ithaca, N.Y., USA). The crystal was mounted in a stream of cold nitrogen at 100(1) K and centered in the X-ray beam by using a video camera.

The crystal evaluation and data collection were performed on a Bruker Quazar SMART APEXII diffractometer (Bruker AXS, Inc., Madison, Wis., USA) with Mo $K_\alpha$ ($\lambda$=0.71073 Å) radiation and the diffractometer-to-crystal distance of 4.96 cm.

The initial cell constants were obtained from three series of ω scans at different starting angles. Each series consisted of 12 frames collected at intervals of 0.5° in a 6° range about ω with the exposure time of 2 seconds per frame. The reflections were successfully indexed by an automated indexing routine built in the APEXII program suite. The final cell constants were calculated from a set of 9673 strong reflections from the actual data collection.

The data were collected by using the full sphere data collection routine to survey the reciprocal space to the extent of a full sphere to a resolution of 0.70 Å. A total of 48251 data were harvested by collecting 6 sets of frames with 0.5° scans in ω and φ with exposure times of 20 sec per frame. These highly redundant datasets were corrected for Lorentz and polarization effects. The absorption correction was based on fitting a function to the empirical transmission surface as sampled by multiple equivalent measurements. Bruker-AXS. (2007-2014) APEX2 (Ver. 2014.1-1), SAD-ABS (2012-1), and SAINT+ (Ver. 8.32A) Software Reference Manuals. Bruker-AXS, Madison, Wis., USA.

(12.1.2) Structure Solution and Refinement:

The systematic absences in the diffraction data were uniquely consistent for the space group $P2_1/n$ that yielded chemically reasonable and computationally stable results of refinement. Sheldrick, G. M. (2008) SHELXL. *Acta Cryst.* *A*64, 112-122. Dolomanov, O. V.; Bourhis, L. J.; Gildea, R. J.; Howard, J. A. K.; Puschmann, H. "OLEX2: a complete structure solution, refinement and analysis program". *J. Appl. Cryst.* (2009) 42, 339-341. Guzei, I. A. (2013). Internal laboratory computer programs Gn.

A successful solution by the direct methods provided most non-hydrogen atoms from the E-map. The remaining non-hydrogen atoms were located in an alternating series of least-squares cycles and difference Fourier maps. All non-hydrogen atoms were refined with anisotropic displacement coefficients. All hydrogen atoms except H2(N2) were included in the structure factor calculation at idealized positions and were allowed to ride on the neighboring atoms with relative isotropic displacement coefficients. The H2 atom was located in the difference Fourier map and refined independently.

The final least-squares refinement of 277 parameters against 4971 data resulted in residuals R (based on $F^2$ for I≥2σ) and wR (based on $F^2$ for all data) of 0.0370 and 0.1014, respectively. The final difference Fourier map was featureless.

(12.1.3) Summary for 9b:

Crystal Data for $C_{25}H_{22}N_2O_2S$ (M=414.50): monoclinic, space group $P2_1/n$ (no. 14), a=13.247(3) Å, b=11.312(3) Å, c=14.218(4) Å, β=109.780(16)°, V=2005.0(9) Å$^3$, Z=4, T=100.01 K, μ(MoKα)=0.187 mm$^{-1}$, Dcalc=1.373 g/mm$^3$, 48251 reflections measured (3.634≤2Θ≤56.666), 4971 unique ($R_{int}$=0.0212, $R_{sigma}$=0.0096) which were used in all calculations. The final $R_1$ was 0.0370 (I>2σ(I)) and $wR_2$ was 0.1014 (all data).

TABLE 6

Crystal data and structure refinement for 9b.

| | |
|---|---|
| Identification code | 9b |
| Empirical formula | $C_{25}H_{22}N_2O_2S$ |
| Formula weight | 414.50 |
| Temperature/K | 100.01 |
| Crystal system | monoclinic |
| Space group | $P2_1/n$ |
| a/Å | 13.247(3) |
| b/Å | 11.312(3) |
| c/Å | 14.218(4) |
| α/° | 90 |
| β/° | 109.780(16) |
| γ/° | 90 |
| Volume/Å$^3$ | 2005.0(9) |
| Z | 4 |
| $\rho_{calc}$mg/mm$^3$ | 1.373 |
| m/mm$^{-1}$ | 0.187 |
| F(000) | 872.0 |
| Crystal size/mm$^3$ | 0.56 × 0.48 × 0.41 |
| Radiation | MoKα (λ = 0.71073) |
| 2Θ range for data collection | 3.634 to 56.666° |

TABLE 6-continued

Crystal data and structure refinement for 9b.

| | |
|---|---|
| Index ranges | −17 ≤ h ≤ 17, −15 ≤ k ≤ 15, −18 ≤ l ≤ 18 |
| Reflections collected | 48251 |
| Independent reflections | 4971 [$R_{int}$ = 0.0212, $R_{sigma}$ = 0.0096] |
| Data/restraints/parameters | 4971/0/277 |
| Goodness-of-fit on $F^2$ | 1.046 |
| Final R indexes [I >= 2σ (I)] | $R_1$ = 0.0370, $wR_2$ = 0.1000 |
| Final R indexes [all data] | $R_1$ = 0.0384, $wR_2$ = 0.1014 |
| Largest diff. peak/hole/e Å$^{-3}$ | 0.42/−0.37 |

TABLE 7

Fractional Atomic Coordinates (×10$^4$) and Equivalent Isotropic Displacement Parameters (Å$^2$ × 10$^3$) for 9b. $U_{eq}$ is defined as ⅓ of of the trace of the orthogonalised $U_{IJ}$ tensor.

| Atom | x | y | z | U(eq) |
|---|---|---|---|---|
| S1 | 5203.5(2) | 2906.9(2) | 7821.4(2) | 16.03(9) |
| O1 | 4426.5(7) | 3399.6(8) | 8208.3(6) | 20.49(18) |
| O2 | 6123.7(7) | 2323.2(8) | 8489.8(6) | 21.52(19) |
| N1 | 5672.5(8) | 4022.4(9) | 7323.6(7) | 17.15(19) |
| N2 | 4941.6(9) | 6834.2(10) | 9582.1(8) | 21.0(2) |
| C1 | 4542.4(9) | 1943.3(10) | 6846.3(8) | 15.6(2) |
| C2 | 5069.0(9) | 930.1(11) | 6711.4(9) | 18.5(2) |
| C3 | 4529(1) | 153.3(11) | 5951.7(9) | 20.7(2) |
| C4 | 3481(1) | 380.1(11) | 5329.1(9) | 20.3(2) |
| C5 | 2970.8(10) | 1407.1(11) | 5486.5(9) | 20.8(2) |
| C6 | 3488.6(9) | 2187.9(10) | 6246.2(9) | 18.7(2) |
| C7 | 2898.2(11) | −481.8(13) | 4521.2(11) | 29.8(3) |
| C8 | 6562.0(9) | 3887.2(10) | 6989.1(9) | 17.8(2) |
| C9 | 7359.5(10) | 3023.6(11) | 7206.9(10) | 21.9(2) |
| C10 | 8149.9(10) | 3154.1(12) | 6770.9(11) | 25.6(3) |
| C11 | 8145.1(10) | 4106.2(13) | 6143.7(11) | 26.7(3) |
| C12 | 7347.8(10) | 4959.2(12) | 5930.9(10) | 23.5(2) |
| C13 | 6544.0(9) | 4846.2(10) | 6358.4(9) | 18.4(2) |
| C14 | 5618.7(9) | 5564.8(10) | 6283.4(8) | 18.0(2) |
| C15 | 5332.3(11) | 6691.0(11) | 5700.7(10) | 23.5(2) |
| C16 | 5092.3(9) | 5054.7(10) | 6847.5(8) | 16.9(2) |
| C17 | 4114.4(9) | 5513.7(11) | 7031.2(9) | 18.4(2) |
| C18 | 4345.8(9) | 6235.3(10) | 7974.0(9) | 17.8(2) |
| C19 | 3989.4(9) | 7426.2(11) | 8024.3(9) | 18.0(2) |
| C20 | 3392.2(10) | 8242.7(11) | 7312(1) | 21.7(2) |
| C21 | 3204.6(11) | 9355.7(12) | 7622.9(10) | 24.8(3) |
| C22 | 3585.4(10) | 9663.8(11) | 8640.2(10) | 25.0(3) |
| C23 | 4162.8(10) | 8875.9(11) | 9365(1) | 21.8(2) |
| C24 | 4368.4(9) | 7764.6(11) | 9043.6(9) | 18.7(2) |
| C25 | 4920.2(10) | 5917.3(11) | 8936.3(9) | 20.1(2) |

TABLE 8

Anisotropic Displacement Parameters (Å$^2$ × 10$^3$) for 9b. The Anisotropic displacement factor exponent takes the form: $-2\pi^2[h^2a^{*2}U_{11} + 2hka^* b^* U_{12} + \ldots]$.

| Atom | $U_{11}$ | $U_{22}$ | $U_{33}$ | $U_{23}$ | $U_{13}$ | $U_{12}$ |
|---|---|---|---|---|---|---|
| S1 | 18.20(15) | 15.47(14) | 13.91(14) | −0.78(9) | 4.77(10) | −0.36(9) |
| O1 | 24.3(4) | 20.4(4) | 19.2(4) | −1.8(3) | 10.5(3) | −0.3(3) |
| O2 | 22.6(4) | 21.6(4) | 16.4(4) | 0.7(3) | 1.3(3) | 0.9(3) |
| N1 | 17.3(4) | 15.0(4) | 20.1(5) | −0.2(4) | 7.6(4) | 0.5(3) |
| N2 | 24.8(5) | 19.3(5) | 18.9(5) | −2.3(4) | 7.4(4) | 0.0(4) |
| C1 | 18.3(5) | 14.8(5) | 13.5(5) | −0.5(4) | 5.1(4) | −1.8(4) |
| C2 | 17.5(5) | 18.9(5) | 18.6(5) | 0.1(4) | 5.6(4) | 1.1(4) |
| C3 | 22.6(6) | 18.6(5) | 21.9(6) | −3.3(4) | 8.8(5) | 0.9(4) |
| C4 | 22.5(6) | 21.2(6) | 17.4(5) | −2.4(4) | 6.8(4) | −3.5(4) |
| C5 | 18.9(5) | 22.2(6) | 18.5(5) | 1.0(4) | 2.6(4) | −0.1(4) |
| C6 | 19.2(5) | 16.6(5) | 19.3(5) | 1.1(4) | 5.4(4) | 1.4(4) |
| C7 | 27.3(6) | 31.0(7) | 27.3(6) | −11.4(5) | 4.5(5) | −4.2(5) |
| C8 | 16.0(5) | 18.1(5) | 19.1(5) | −4.9(4) | 5.7(4) | −2.5(4) |
| C9 | 18.1(5) | 19.4(5) | 27.3(6) | −3.0(5) | 6.7(5) | −0.2(4) |
| C10 | 17.8(5) | 24.7(6) | 34.5(7) | −7.0(5) | 9.0(5) | 0.4(5) |
| C11 | 21.7(6) | 28.8(7) | 33.9(7) | −8.2(5) | 15.0(5) | −5.0(5) |

TABLE 8-continued

Anisotropic Displacement Parameters (Å$^2$ × 10$^3$) for 9b. The Anisotropic displacement factor exponent takes the form: $-2\pi^2[h^2a*^2U_{11} + 2hka*b*U_{12} + ...]$.

| Atom | $U_{11}$ | $U_{22}$ | $U_{33}$ | $U_{23}$ | $U_{13}$ | $U_{12}$ |
|---|---|---|---|---|---|---|
| C12 | 24.7(6) | 22.7(6) | 26.2(6) | −4.7(5) | 12.5(5) | −5.6(5) |
| C13 | 19.2(5) | 17.0(5) | 19.0(5) | −5.5(4) | 6.5(4) | −2.9(4) |
| C14 | 20.5(5) | 16.1(5) | 17.3(5) | −3.3(4) | 6.5(4) | −1.1(4) |
| C15 | 28.2(6) | 19.3(6) | 23.4(6) | 2.0(5) | 9.5(5) | −0.1(5) |
| C16 | 18.3(5) | 14.8(5) | 16.6(5) | −2.4(4) | 4.6(4) | 0.1(4) |
| C17 | 18.6(5) | 17.5(5) | 19.1(5) | −0.9(4) | 6.5(4) | 1.4(4) |
| C18 | 17.6(5) | 17.2(5) | 20.6(5) | −1.3(4) | 8.9(4) | 0.0(4) |
| C19 | 17.0(5) | 17.9(5) | 22.1(5) | −0.5(4) | 10.6(4) | −0.7(4) |
| C20 | 22.3(5) | 22.7(6) | 23.5(6) | 2.5(5) | 12.2(5) | 2.5(5) |
| C21 | 26.2(6) | 21.5(6) | 31.1(6) | 6.3(5) | 15.2(5) | 5.0(5) |
| C22 | 26.0(6) | 18.1(6) | 35.8(7) | −2.3(5) | 17.0(5) | 0.1(5) |
| C23 | 22.6(5) | 19.7(6) | 26.8(6) | −5.0(5) | 12.9(5) | −3.1(4) |
| C24 | 18.1(5) | 18.2(5) | 22.3(6) | −1.1(4) | 10.2(4) | −1.3(4) |
| C25 | 21.9(5) | 17.2(5) | 21.3(6) | −2.4(4) | 7.5(4) | 0.5(4) |

TABLE 9

Bond Lengths for 9b.

| Atom | Atom | Length/Å |
|---|---|---|
| S1 | O1 | 1.4339(9) |
| S1 | O2 | 1.4287(9) |
| S1 | N1 | 1.6664(11) |
| S1 | C1 | 1.7480(12) |
| N1 | C8 | 1.4204(15) |
| N1 | C16 | 1.4354(15) |
| N2 | C24 | 1.3703(16) |
| N2 | C25 | 1.3793(16) |
| C1 | C2 | 1.3885(16) |
| C1 | C6 | 1.3954(16) |
| C2 | C3 | 1.3884(17) |
| C3 | C4 | 1.3947(17) |
| C4 | C5 | 1.3997(18) |
| C4 | C7 | 1.5054(17) |
| C5 | C6 | 1.3842(17) |
| C8 | C9 | 1.3947(17) |
| C8 | C13 | 1.4026(17) |
| C9 | C10 | 1.3935(18) |
| C10 | C11 | 1.397(2) |
| C11 | C12 | 1.3863(19) |
| C12 | C13 | 1.3992(17) |
| C13 | C14 | 1.4444(16) |
| C14 | C15 | 1.4969(17) |
| C14 | C16 | 1.3569(16) |
| C16 | C17 | 1.4984(16) |
| C17 | C18 | 1.5096(16) |
| C18 | C19 | 1.4373(16) |
| C18 | C25 | 1.3696(17) |
| C19 | C20 | 1.4009(17) |
| C19 | C24 | 1.4165(17) |
| C20 | C21 | 1.3846(18) |
| C21 | C22 | 1.405(2) |
| C22 | C23 | 1.3814(19) |
| C23 | C24 | 1.3954(17) |

TABLE 10

Bond Angles for 9b.

| Atom | Atom | Atom | Angle/° | Atom | Atom | Atom | Angle/° |
|---|---|---|---|---|---|---|---|
| O1 | S1 | N1 | 106.72(5) | C11 | C12 | C13 | 118.50(12) |
| O1 | S1 | C1 | 108.34(6) | C8 | C13 | C14 | 108.24(10) |
| O2 | S1 | O1 | 119.08(6) | C12 | C13 | C8 | 119.84(11) |
| O2 | S1 | N1 | 106.01(6) | C12 | C13 | C14 | 131.92(12) |
| O2 | S1 | C1 | 108.97(6) | C13 | C14 | C15 | 124.73(11) |
| N1 | S1 | C1 | 107.11(5) | C13 | C14 | C16 | 108.06(11) |
| C8 | N1 | S1 | 122.10(8) | C16 | C14 | C15 | 127.18(11) |
| C8 | N1 | C16 | 107.59(9) | N1 | C16 | C17 | 123.79(10) |
| C16 | N1 | S1 | 126.82(8) | C14 | C16 | N1 | 108.94(10) |
| C24 | N2 | C25 | 108.85(11) | C14 | C16 | C17 | 127.10(11) |
| C2 | C1 | S1 | 118.95(9) | C16 | C17 | C18 | 114.48(10) |
| C2 | C1 | C6 | 121.65(11) | C19 | C18 | C17 | 125.42(11) |
| C6 | C1 | S1 | 119.36(9) | C25 | C18 | C17 | 128.48(11) |
| C3 | C2 | C1 | 118.64(11) | C25 | C18 | C19 | 106.10(10) |
| C2 | C3 | C4 | 121.16(11) | C20 | C19 | C18 | 134.16(11) |
| C3 | C4 | C5 | 118.82(11) | C20 | C19 | C24 | 118.64(11) |
| C3 | C4 | C7 | 120.56(12) | C24 | C19 | C18 | 107.20(10) |
| C5 | C4 | C7 | 120.59(11) | C21 | C20 | C19 | 119.16(12) |
| C6 | C5 | C4 | 121.05(11) | C20 | C21 | C22 | 120.91(12) |
| C5 | C6 | C1 | 118.66(11) | C23 | C22 | C21 | 121.54(12) |
| C9 | C8 | N1 | 130.77(11) | C22 | C23 | C24 | 117.20(12) |
| C9 | C8 | C13 | 122.11(11) | N2 | C24 | C19 | 107.55(10) |
| C13 | C8 | N1 | 107.11(10) | N2 | C24 | C23 | 129.91(12) |
| C10 | C9 | C8 | 116.99(12) | C23 | C24 | C19 | 122.53(11) |
| C9 | C10 | C11 | 121.59(12) | C18 | C25 | N2 | 110.29(11) |
| C12 | C11 | C10 | 120.97(12) | | | | |

TABLE 11

Hydrogen Bonds for 9b.

| D H A | d(D − H)/Å | d(H − A)/Å | d(D − A)/Å | D − H − A/° |
|---|---|---|---|---|
| N2H2O1[1] | 0.877(18) | 2.123(19) | 2.9766(16) | 164.2(16) |

[1] 1 − X, 1 − Y, 2 − Z

TABLE 12

Torsion Angles for 9b.

| A | B | C | D | Angle/° | A | B | C | D | Angle/° |
|---|---|---|---|---|---|---|---|---|---|
| S1 | N1 | C8 | C9 | −18.46(17) | C9 | C10 | C11 | C12 | −0.1(2) |
| S1 | N1 | C8 | C13 | 162.66(8) | C10 | C11 | C12 | C13 | −0.05(19) |
| S1 | N1 | C16 | C14 | −161.64(9) | C11 | C12 | C13 | C8 | 0.25(18) |
| S1 | N1 | C16 | C17 | 22.74(16) | C11 | C12 | C13 | C14 | −179.65(12) |
| S1 | C1 | C2 | C3 | 178.36(9) | C12 | C13 | C14 | C15 | −1.9(2) |

TABLE 12-continued

Torsion Angles for 9b.

| A | B | C | D | Angle/° | A | B | C | D | Angle/° |
|---|---|---|---|---|---|---|---|---|---|
| S1 | C1 | C6 | C5 | −179.06(9) | C12 | C13 | C14 | C16 | 179.71(12) |
| O1 | S1 | N1 | C8 | 171.33(9) | C13 | C8 | C9 | C10 | 0.21(18) |
| O1 | S1 | N1 | C16 | −32.44(11) | C13 | C14 | C16 | N1 | 1.73(13) |
| O1 | S1 | C1 | C2 | −145.08(9) | C13 | C14 | C16 | C17 | 177.17(11) |
| O1 | S1 | C1 | C6 | 32.69(11) | C14 | C16 | C17 | C18 | −94.30(14) |
| O2 | S1 | N1 | C8 | 43.43(10) | C15 | C14 | C16 | N1 | −176.62(11) |
| O2 | S1 | N1 | C16 | −160.33(9) | C15 | C14 | C16 | C17 | −1.2(2) |
| O2 | S1 | C1 | C2 | −14.13(11) | C16 | N1 | C8 | C9 | −178.67(12) |
| O2 | S1 | C1 | C6 | 163.64(9) | C16 | N1 | C8 | C13 | 2.44(12) |
| N1 | S1 | C1 | C2 | 100.13(10) | C16 | C17 | C18 | C19 | 123.67(12) |
| N1 | S1 | C1 | C6 | −82.10(10) | C16 | C17 | C18 | C25 | −56.27(17) |
| N1 | C8 | C9 | C10 | −178.53(12) | C17 | C18 | C19 | C20 | −0.9(2) |
| N1 | C8 | C13 | C12 | 178.66(10) | C17 | C18 | C19 | C24 | 179.35(11) |
| N1 | C8 | C13 | C14 | −1.42(12) | C17 | C18 | C25 | N2 | −179.92(11) |
| N1 | C16 | C17 | C18 | 80.51(14) | C18 | C19 | C20 | C21 | −178.79(12) |
| C1 | S1 | N1 | C8 | −72.81(10) | C18 | C19 | C24 | N2 | 1.01(13) |
| C1 | S1 | N1 | C16 | 83.42(11) | C18 | C19 | C24 | C23 | −179.74(11) |
| C1 | C2 | C3 | C4 | 0.32(18) | C19 | C18 | C25 | N2 | 0.13(14) |
| C2 | C1 | C6 | C5 | −1.35(18) | C19 | C20 | C21 | C22 | −1.32(19) |
| C2 | C3 | C4 | C5 | −0.55(18) | C20 | C19 | C24 | N2 | −178.77(10) |
| C2 | C3 | C4 | C7 | −178.82(12) | C20 | C19 | C24 | C23 | 0.49(17) |
| C3 | C4 | C5 | C6 | −0.19(19) | C20 | C21 | C22 | C23 | 0.3(2) |
| C4 | C5 | C6 | C1 | 1.11(18) | C21 | C22 | C23 | C24 | 1.02(18) |
| C6 | C1 | C2 | C3 | 0.64(18) | C22 | C23 | C24 | N2 | 177.63(12) |
| C7 | C4 | C5 | C6 | 178.08(12) | C22 | C23 | C24 | C19 | −1.44(18) |
| C8 | N1 | C16 | C14 | −2.63(13) | C24 | N2 | C25 | C18 | 0.51(14) |
| C8 | N1 | C16 | C17 | −178.24(10) | C24 | C19 | C20 | C21 | 0.91(17) |
| C8 | C9 | C10 | C11 | −0.01(19) | C25 | N2 | C24 | C19 | −0.94(13) |
| C8 | C13 | C14 | C15 | 178.20(11) | C25 | N2 | C24 | C23 | 179.88(12) |
| C8 | C13 | C14 | C16 | −0.20(13) | C25 | C18 | C19 | C20 | 179.03(13) |
| C9 | C8 | C13 | C12 | −0.34(18) | C25 | C18 | C19 | C24 | −0.69(13) |
| C9 | C8 | C13 | C14 | 179.58(11) | | | | | |

TABLE 13

Hydrogen Atom Coordinates (Å × 10⁴) and Isotropic Displacement Parameters (Å² × 10³) for 9b.

| Atom | x | y | z | U(eq) |
|---|---|---|---|---|
| H2 | 5253(14) | 6801(16) | 10233(14) | 30(4) |
| H2A | 5784 | 772 | 7130 | 22 |
| H3 | 4880 | −545 | 5854 | 25 |
| H5 | 2258 | 1571 | 5065 | 25 |
| H6 | 3134 | 2876 | 6357 | 22 |
| H7A | 3389 | −1116 | 4488 | 45 |
| H7B | 2636 | −70 | 3877 | 45 |
| H7C | 2290 | −821 | 4673 | 45 |
| H9 | 7364 | 2376 | 7633 | 26 |
| H10 | 8706 | 2582 | 6903 | 31 |
| H11 | 8696 | 4170 | 5859 | 32 |
| H12 | 7347 | 5606 | 5504 | 28 |
| H15A | 5893 | 7281 | 5990 | 35 |
| H15B | 4647 | 6986 | 5727 | 35 |
| H15C | 5269 | 6543 | 5004 | 35 |
| H17A | 3657 | 4835 | 7065 | 22 |
| H17B | 3701 | 6007 | 6455 | 22 |
| H20 | 3119 | 8035 | 6624 | 26 |
| H21 | 2813 | 9919 | 7142 | 30 |
| H22 | 3442 | 10432 | 8834 | 30 |
| H23 | 4410 | 9082 | 10053 | 26 |
| H25 | 5256 | 5172 | 9131 | 24 |

(12.2) Structural Report on Compound 13:

(12.2.1) Data Collection:

A colorless crystal with approximate dimensions 0.56× 0.47×0.44 mm³ was selected under oil under ambient conditions and attached to the tip of a MiTeGen MicroMount©. The crystal was mounted in a stream of cold nitrogen at 100(1) K and centered in the X-ray beam by using a video camera.

The crystal evaluation and data collection were performed on a Bruker SMART APEXII diffractometer with Cu $K_\alpha$ ($\lambda$=1.54178 Å) radiation and the diffractometer to crystal distance of 4.03 cm.

The initial cell constants were obtained from three series of ω scans at different starting angles. Each series consisted of 35 frames collected at intervals of 0.6° in a 25° range about ω with the exposure time of 2 seconds per frame. The reflections were successfully indexed by an automated indexing routine built in the APEXII program. The final cell constants were calculated from a set of 9384 strong reflections from the actual data collection.

The data were collected by using the full sphere data collection routine to survey the reciprocal space to the extent of a full sphere to a resolution of 0.82 Å. A total of 46397 data were harvested by collecting 22 sets of frames with 0.7° scans in ω and φ with an exposure time 5-10 sec per frame. These highly redundant datasets were corrected for Lorentz and polarization effects. The absorption correction was based on fitting a function to the empirical transmission surface as sampled by multiple equivalent measurements. Bruker-AXS. (2007-2014) APEX2 (Ver. 2014.1-1), SAD-ABS (2012-1), and SAINT+ (Ver. 8.32A) Software Reference Manuals. Bruker-AXS, Madison, Wis., USA.

(12.2.2) Structure Solution and Refinement:

The systematic absences in the diffraction data were uniquely consistent for the space group P2₁/c that yielded chemically reasonable and computationally stable results of refinement. Sheldrick, G. M. (2008) SHELXL. Acta Cryst. A64, 112-122. Dolomanov, O. V.; Bourhis, L. J.; Gildea, R. J.; Howard, J. A. K.; Puschmann, H. "OLEX2: a complete structure solution, refinement and analysis program". J. Appl. Cryst. (2009) 42, 339-341. Guzei, I. A. (2013). Internal laboratory computer programs Gn.

A successful solution by the direct methods provided most non-hydrogen atoms from the E-map. The remaining non-hydrogen atoms were located in an alternating series of least-squares cycles and difference Fourier maps. All non-hydrogen atoms were refined with anisotropic displacement coefficients. All hydrogen atoms except H1(N1) and H2(N2) were included in the structure factor calculation at idealized positions and were allowed to ride on the neighboring atoms with relative isotropic displacement coefficients. Atoms H1 and H2 were located in the difference Fourier map and refined independently.

The final least-squares refinement of 333 parameters against 4996 data resulted in residuals R (based on $F^2$ for I≥2σ) and wR (based on $F^2$ for all data) of 0.0348 and 0.0893, respectively. The final difference Fourier map was featureless.

(12.2.3) Summary:

Crystal Data for $C_{31}H_{26}N_2O_2S$ (M=490.60): monoclinic, space group $P2_1/c$ (no. 14), a=14.1262(11) Å, b=9.3818(5) Å, c=20.2526(8) Å, β=108.247(5)°, V=2549.1(3) Å$^3$, Z=4, T=99.98 K, μ(CuKα)=1.370 mm$^{-1}$, Dcalc=1.278 g/mm$^3$, 46397 reflections measured (6.588≤2Θ≥145.99), 4996 unique ($R_{int}$=0.0173, $R_{sigma}$=0.0083) which were used in all calculations. The final $R_1$ was 0.0348 (I>2σ(I)) and wR$_2$ was 0.0893 (all data).

TABLE 14

Crystal data and structure refinement for 13.

| | |
|---|---|
| Identification code | 13 |
| Empirical formula | $C_{31}H_{26}N_2O_2S$ |
| Formula weight | 490.60 |
| Temperature/K | 99.98 |
| Crystal system | monoclinic |
| Space group | $P2_1/c$ |
| a/Å | 14.1262(11) |
| b/Å | 9.3818(5) |
| c/Å | 20.2526(8) |
| α/° | 90 |
| β/° | 108.247(5) |
| γ/° | 90 |
| Volume/Å$^3$ | 2549.1(3) |
| Z | 4 |
| $ρ_{calc}$mg/mm$^3$ | 1.278 |
| m/mm$^{-1}$ | 1.370 |
| F(000) | 1032.0 |
| Crystal size/mm$^3$ | 0.56 × 0.47 × 0.44 |
| Radiation | CuKα (λ = 1.54178) |
| 2Θ range for data collection | 6.588 to 145.99° |
| Index ranges | −17 ≤ h ≤ 16, −11 ≤ k ≤ 11, −25 ≤ l ≤ 25 |
| Reflections collected | 46397 |
| Independent reflections | 4996 [$R_{int}$ = 0.0173, $R_{sigma}$ = 0.0083] |

TABLE 14-continued

Crystal data and structure refinement for 13.

| | |
|---|---|
| Data/restraints/parameters | 4996/0/333 |
| Goodness-of-fit on $F^2$ | 1.055 |
| Final R indexes [I >= 2σ (I)] | $R_1$ = 0.0348, w$R_2$ = 0.0892 |
| Final R indexes [all data] | $R_1$ = 0.0349, w$R_2$ = 0.0893 |
| Largest diff. peak/hole/e Å$^{-3}$ | 0.32/−0.49 |

TABLE 15

Fractional Atomic Coordinates (×10$^4$) and Equivalent Isotropic Displacement Parameters (Å$^2$ × 10$^3$) for 13. $U_{eq}$ is defined as ⅓ of of the trace of the orthogonalised $U_{IJ}$ tensor.

| Atom | x | y | z | U(eq) |
|---|---|---|---|---|
| S1 | 7366.3(2) | 5399.3(3) | 6318.8(2) | 15.13(9) |
| O1 | 8059.2(7) | 5873.2(10) | 6961.2(5) | 23.2(2) |
| O2 | 6353.3(6) | 5887.7(9) | 6118.7(5) | 19.66(19) |
| N1 | 7256.0(8) | 3670.0(11) | 6335.8(5) | 16.1(2) |
| N2 | 5753.8(8) | 3114.4(12) | 4033.4(6) | 21.1(2) |
| C1 | 7877.8(9) | 5798.4(13) | 5654.3(6) | 17.4(2) |
| C2 | 7258.7(10) | 5775.3(13) | 4967.3(7) | 20.7(3) |
| C3 | 7660.2(11) | 6070.6(14) | 4442.0(7) | 25.6(3) |
| C4 | 8668.6(12) | 6382.9(17) | 4590.4(8) | 31.5(3) |
| C5 | 9271.7(11) | 6388.6(19) | 5279.9(9) | 34.9(4) |
| C6 | 8884.6(10) | 6106.6(16) | 5817.5(7) | 26.4(3) |
| C7 | 9097.1(14) | 6719(2) | 4013.2(10) | 50.8(5) |
| C8 | 8022.9(9) | 2633.1(13) | 6456.8(6) | 16.4(2) |
| C9 | 8976.6(9) | 2941.7(15) | 6897.2(6) | 21.8(3) |
| C10 | 9717(1) | 1908.2(17) | 7044.8(7) | 27.1(3) |
| C11 | 9501.1(11) | 563.0(17) | 6760.4(7) | 29.5(3) |
| C12 | 8550.8(11) | 252.4(15) | 6324.1(7) | 25.6(3) |
| C13 | 7794.3(9) | 1274.7(14) | 6152.0(6) | 18.1(3) |
| C14 | 6755.2(9) | 930.3(13) | 5636.0(6) | 17.6(2) |
| C15 | 5990.4(9) | 1242.1(13) | 5976.5(6) | 18.5(3) |
| C16 | 5396.4(9) | 1571.5(13) | 6262.7(6) | 18.8(3) |
| C17 | 4721.5(9) | 1972.1(13) | 6634.6(6) | 17.4(2) |
| C18 | 4892.6(10) | 3213.0(14) | 7038.8(7) | 20.9(3) |
| C19 | 4268(1) | 3557.7(14) | 7424.1(7) | 23.5(3) |
| C20 | 3473.1(10) | 2679.0(15) | 7413.3(7) | 23.4(3) |
| C21 | 3297(1) | 1447.5(15) | 7012.1(7) | 23.4(3) |
| C22 | 3913(1) | 1094.2(14) | 6622.3(7) | 20.5(3) |
| C23 | 6645.8(11) | −658.8(14) | 5420.5(8) | 25.6(3) |
| C24 | 6556.5(9) | 1821.6(12) | 4976.2(6) | 16.0(2) |
| C25 | 7166.8(9) | 1884.9(13) | 4524.8(6) | 17.7(2) |
| C26 | 8093.4(10) | 1300.1(15) | 4544.5(7) | 24.8(3) |
| C27 | 8440.3(12) | 1529.9(18) | 3986.6(8) | 32.8(3) |
| C28 | 7897.5(12) | 2345.5(18) | 3411.2(8) | 33.5(3) |
| C29 | 6991.2(11) | 2937.3(15) | 3378.2(7) | 27.1(3) |
| C30 | 6632.9(10) | 2692.8(13) | 3936.8(6) | 19.9(3) |
| C31 | 5710.5(9) | 2575.0(13) | 4654.1(6) | 18.7(2) |

TABLE 16

Anisotropic Displacement Parameters (Å$^2$ × 10$^3$) for 13. The Anisotropic displacement factor exponent takes the form: $-2\pi^2[h^2a^{*2}U_{11} + 2hka^*b^*U_{12} + \ldots]$.

| Atom | $U_{11}$ | $U_{22}$ | $U_{33}$ | $U_{23}$ | $U_{13}$ | $U_{12}$ |
|---|---|---|---|---|---|---|
| S1 | 13.59(16) | 15.99(15) | 16.54(15) | −4.14(10) | 5.76(12) | −1.95(10) |
| O1 | 19.1(5) | 30.0(5) | 21.0(5) | −10.2(4) | 6.8(4) | −5.5(4) |
| O2 | 17.1(4) | 18.1(4) | 25.0(4) | −3.0(3) | 8.2(4) | 0.8(3) |
| N1 | 11.1(5) | 16.9(5) | 18.9(5) | 0.0(4) | 2.5(4) | −1.3(4) |
| N2 | 19.6(6) | 20.3(5) | 19.2(5) | 3.0(4) | 0.1(4) | 0.6(4) |
| C1 | 19.3(6) | 14.0(5) | 21.5(6) | −1.3(5) | 9.8(5) | −0.8(4) |
| C2 | 23.8(7) | 16.5(6) | 22.5(6) | −1.1(5) | 8.1(5) | −3.1(5) |
| C3 | 34.7(8) | 21.4(6) | 22.1(6) | 2.6(5) | 11.1(6) | 1.5(5) |
| C4 | 35.4(8) | 33.2(8) | 33.1(8) | 10.3(6) | 21.2(7) | 6.7(6) |
| C5 | 22.3(7) | 47.2(9) | 39.5(8) | 9.4(7) | 15.9(6) | −0.6(6) |
| C6 | 20.4(7) | 32.9(7) | 26.9(7) | 1.6(6) | 9.1(5) | −1.8(5) |
| C7 | 45.7(10) | 74.7(13) | 43.1(10) | 23.9(9) | 30.2(9) | 12.8(9) |

TABLE 16-continued

Anisotropic Displacement Parameters (Å² × 10³) for 13. The Anisotropic displacement factor exponent takes the form: $-2\pi^2[h^2a^{*2}U_{11} + 2hka^*b^*U_{12} + \ldots]$.

| Atom | $U_{11}$ | $U_{22}$ | $U_{33}$ | $U_{23}$ | $U_{13}$ | $U_{12}$ |
|------|----------|----------|----------|----------|----------|----------|
| C8   | 14.3(6)  | 22.4(6)  | 13.4(5)  | 4.9(5)   | 5.3(4)   | 3.3(5)   |
| C9   | 16.8(6)  | 33.3(7)  | 14.9(6)  | 2.9(5)   | 4.3(5)   | 0.9(5)   |
| C10  | 15.8(6)  | 48.4(9)  | 15.9(6)  | 8.9(6)   | 3.4(5)   | 7.5(6)   |
| C11  | 24.0(7)  | 43.5(9)  | 21.9(7)  | 12.9(6)  | 8.4(6)   | 19.7(6)  |
| C12  | 30.0(7)  | 26.1(7)  | 22.4(6)  | 6.9(5)   | 10.7(6)  | 12.4(6)  |
| C13  | 18.7(6)  | 21.4(6)  | 15.7(6)  | 5.6(5)   | 7.6(5)   | 4.4(5)   |
| C14  | 19.3(6)  | 12.8(6)  | 20.7(6)  | 1.4(5)   | 6.4(5)   | 1.2(4)   |
| C15  | 18.7(6)  | 14.3(5)  | 21.4(6)  | 3.0(5)   | 4.9(5)   | -2.7(5)  |
| C16  | 18.5(6)  | 16.0(6)  | 20.4(6)  | 3.6(5)   | 3.8(5)   | -2.9(5)  |
| C17  | 18.0(6)  | 17.7(6)  | 15.4(6)  | 4.1(4)   | 3.7(5)   | -0.1(5)  |
| C18  | 19.5(6)  | 19.1(6)  | 21.3(6)  | 1.4(5)   | 2.4(5)   | -3.9(5)  |
| C19  | 29.3(7)  | 20.4(6)  | 18.4(6)  | -1.7(5)  | 3.9(5)   | 0.2(5)   |
| C20  | 27.5(7)  | 26.6(7)  | 18.5(6)  | 4.5(5)   | 10.8(5)  | 3.7(5)   |
| C21  | 23.4(7)  | 23.8(7)  | 25.0(6)  | 4.5(5)   | 10.3(5)  | -4.2(5)  |
| C22  | 22.9(6)  | 18.0(6)  | 20.4(6)  | 0.1(5)   | 6.5(5)   | -3.7(5)  |
| C23  | 32.3(8)  | 13.7(6)  | 31.7(7)  | 0.8(5)   | 11.3(6)  | -0.2(5)  |
| C24  | 15.6(6)  | 13.7(5)  | 17.1(6)  | -2.4(4)  | 3.1(5)   | -3.0(4)  |
| C25  | 20.1(6)  | 15.6(6)  | 16.4(6)  | -4.5(4)  | 4.2(5)   | -3.8(5)  |
| C26  | 22.8(7)  | 29.1(7)  | 22.6(6)  | -3.2(5)  | 7.2(5)   | 2.1(5)   |
| C27  | 28.8(8)  | 43.6(9)  | 30.4(7)  | -7.8(6)  | 15.4(6)  | 0.9(6)   |
| C28  | 41.3(9)  | 41.7(9)  | 23.0(7)  | -6.4(6)  | 17.7(6)  | -8.1(7)  |
| C29  | 36.7(8)  | 26.7(7)  | 17.2(6)  | -1.9(5)  | 7.4(6)   | -6.4(6)  |
| C30  | 22.7(6)  | 16.7(6)  | 17.7(6)  | -4.1(5)  | 2.7(5)   | -5.3(5)  |
| C31  | 17.4(6)  | 16.7(6)  | 21.0(6)  | 0.5(5)   | 4.7(5)   | -2.1(5)  |

TABLE 17

Bond Lengths for 13.

| Atom | Atom | Length/Å    |
|------|------|-------------|
| S1   | O1   | 1.4321(9)   |
| S1   | O2   | 1.4347(9)   |
| S1   | N1   | 1.6313(11)  |
| S1   | C1   | 1.7557(12)  |
| N1   | C8   | 1.4191(15)  |
| N2   | C30  | 1.3743(18)  |
| N2   | C31  | 1.3743(17)  |
| C1   | C2   | 1.3927(18)  |
| C1   | C6   | 1.3861(18)  |
| C2   | C3   | 1.3813(19)  |
| C3   | C4   | 1.392(2)    |
| C4   | C5   | 1.390(2)    |
| C4   | C7   | 1.509(2)    |
| C5   | C6   | 1.388(2)    |
| C8   | C9   | 1.3935(18)  |
| C8   | C13  | 1.4088(18)  |
| C9   | C10  | 1.3884(19)  |
| C10  | C11  | 1.381(2)    |
| C11  | C12  | 1.388(2)    |
| C12  | C13  | 1.3965(18)  |
| C13  | C14  | 1.5461(17)  |
| C14  | C15  | 1.4815(17)  |
| C14  | C23  | 1.5475(17)  |
| C14  | C24  | 1.5260(17)  |
| C15  | C16  | 1.2000(19)  |
| C16  | C17  | 1.4377(17)  |
| C17  | C18  | 1.4000(18)  |
| C17  | C22  | 1.4021(17)  |
| C18  | C19  | 1.3867(19)  |
| C19  | C20  | 1.3876(19)  |
| C20  | C21  | 1.389(2)    |
| C21  | C22  | 1.3858(19)  |
| C24  | C25  | 1.4409(17)  |
| C24  | C31  | 1.3656(17)  |
| C25  | C26  | 1.4082(18)  |
| C25  | C30  | 1.4140(18)  |
| C26  | C27  | 1.382(2)    |
| C27  | C28  | 1.404(2)    |
| C28  | C29  | 1.378(2)    |
| C29  | C30  | 1.3953(19)  |

TABLE 18

Bond Angles for 13.

| Atom | Atom | Atom | Angle/° | Atom | Atom | Atom | Angle/° |
|------|------|------|---------|------|------|------|---------|
| O1   | S1   | O2   | 119.67(5)  | C15 | C14 | C13 | 108.69(10) |
| O1   | S1   | N1   | 109.40(6)  | C15 | C14 | C23 | 107.37(10) |
| O1   | S1   | C1   | 107.57(6)  | C15 | C14 | C24 | 109.78(10) |
| O2   | S1   | N1   | 103.31(5)  | C24 | C14 | C13 | 110.65(10) |
| O2   | S1   | C1   | 109.20(6)  | C24 | C14 | C23 | 107.83(10) |
| N1   | S1   | C1   | 107.05(6)  | C16 | C15 | C14 | 176.17(13) |
| C8   | N1   | S1   | 127.78(9)  | C15 | C16 | C17 | 177.40(13) |
| C31  | N2   | C30  | 108.98(11) | C18 | C17 | C16 | 120.16(11) |
| C2   | C1   | S1   | 118.82(10) | C18 | C17 | C22 | 119.30(12) |
| C6   | C1   | S1   | 119.97(10) | C22 | C17 | C16 | 120.48(11) |
| C6   | C1   | C2   | 121.19(12) | C19 | C18 | C17 | 119.95(12) |
| C3   | C2   | C1   | 119.05(12) | C18 | C19 | C20 | 120.46(12) |
| C2   | C3   | C4   | 121.01(13) | C19 | C20 | C21 | 119.94(12) |
| C3   | C4   | C7   | 120.57(15) | C22 | C21 | C20 | 120.18(12) |
| C5   | C4   | C3   | 118.80(13) | C21 | C22 | C17 | 120.17(12) |
| C5   | C4   | C7   | 120.62(15) | C25 | C24 | C14 | 126.55(11) |
| C6   | C5   | C4   | 121.29(14) | C31 | C24 | C14 | 126.54(11) |
| C1   | C6   | C5   | 118.65(13) | C31 | C24 | C25 | 106.47(11) |
| C9   | C8   | N1   | 120.06(12) | C26 | C25 | C24 | 134.55(12) |
| C9   | C8   | C13  | 120.76(12) | C26 | C25 | C30 | 118.59(12) |
| C13  | C8   | N1   | 119.12(11) | C30 | C25 | C24 | 106.81(11) |
| C10  | C9   | C8   | 120.32(13) | C27 | C26 | C25 | 118.71(13) |
| C11  | C10  | C9   | 119.69(13) | C26 | C27 | C28 | 121.49(14) |
| C10  | C11  | C12  | 120.05(13) | C29 | C28 | C27 | 121.15(13) |
| C11  | C12  | C13  | 121.80(14) | C28 | C29 | C30 | 117.51(13) |
| C8   | C13  | C14  | 121.61(11) | N2  | C30 | C25 | 107.56(11) |
| C12  | C13  | C8   | 117.35(12) | N2  | C30 | C29 | 129.89(13) |
| C12  | C13  | C14  | 121.03(12) | C29 | C30 | C25 | 122.53(13) |
| C13  | C14  | C23  | 112.45(10) | C24 | C31 | N2  | 110.16(11) |

TABLE 19

Hydrogen Bonds for 13.

| D  | H  | A   | d(D – H)/Å | d(H – A)/Å | d(D – A)/Å  | D – H – A/° |
|----|----|-----|------------|------------|-------------|-------------|
| N2 | H2 | O2[1] | 0.859(18)  | 2.453(17)  | 3.0426(15)  | 126.4(14)   |

[1] 1 – X, 1 – Y, 1 – Z

TABLE 20

Torsion Angles for 13.

| A | B | C | D | Angle/° | A | B | C | D | Angle/° |
|---|---|---|---|---|---|---|---|---|---|
| S1 | N1 | C8 | C9 | 32.08(16) | C12 | C13 | C14 | C24 | −114.28(13) |
| S1 | N1 | C8 | C13 | −150.78(10) | C13 | C8 | C9 | C10 | −0.28(18) |
| S1 | C1 | C2 | C3 | −179.18(10) | C13 | C14 | C24 | C25 | 56.04(15) |
| S1 | C1 | C6 | C5 | 178.66(12) | C13 | C14 | C24 | C31 | −132.53(13) |
| O1 | S1 | N1 | C8 | −56.14(11) | C14 | C24 | C25 | C26 | −4.7(2) |
| O1 | S1 | C1 | C2 | −164.22(10) | C14 | C24 | C25 | C30 | 172.53(11) |
| O1 | S1 | C1 | C6 | 16.80(13) | C14 | C24 | C31 | N2 | −173.26(11) |
| O2 | S1 | N1 | C8 | 175.35(10) | C15 | C14 | C24 | C25 | 176.00(11) |
| O2 | S1 | C1 | C2 | −32.91(12) | C15 | C14 | C24 | C31 | −12.57(17) |
| O2 | S1 | C1 | C6 | 148.10(11) | C16 | C17 | C18 | C19 | −176.78(12) |
| N1 | S1 | C1 | C2 | 78.29(11) | C16 | C17 | C22 | C21 | 176.49(12) |
| N1 | S1 | C1 | C6 | −100.69(11) | C17 | C18 | C19 | C20 | 0.1(2) |
| N1 | C8 | C9 | C10 | 176.81(11) | C18 | C17 | C22 | C21 | −0.61(19) |
| N1 | C8 | C13 | C12 | −175.46(11) | C18 | C19 | C20 | C21 | −0.3(2) |
| N1 | C8 | C13 | C14 | 5.70(17) | C19 | C20 | C21 | C22 | 0.0(2) |
| C1 | S1 | N1 | C8 | 60.14(11) | C20 | C21 | C22 | C17 | 0.5(2) |
| C1 | C2 | C3 | C4 | 0.2(2) | C22 | C17 | C18 | C19 | 0.32(19) |
| C2 | C1 | C6 | C5 | −0.3(2) | C23 | C14 | C24 | C25 | −67.32(15) |
| C2 | C3 | C4 | C5 | 0.2(2) | C23 | C14 | C24 | C31 | 104.11(14) |
| C2 | C3 | C4 | C7 | −179.34(15) | C24 | C25 | C26 | C27 | 176.52(14) |
| C3 | C4 | C5 | C6 | −0.8(2) | C24 | C25 | C30 | N2 | 0.91(13) |
| C4 | C5 | C6 | C1 | 0.8(2) | C24 | C25 | C30 | C29 | −178.07(12) |
| C6 | C1 | C2 | C3 | −0.21(19) | C24 | C25 | C31 | N2 | −0.43(14) |
| C7 | C4 | C5 | C6 | 178.82(16) | C25 | C24 | C31 | N2 | 0.9(2) |
| C8 | C9 | C10 | C11 | −0.89(19) | C26 | C25 | C30 | N2 | 178.67(11) |
| C8 | C13 | C14 | C15 | −56.09(14) | C26 | C25 | C30 | C29 | −0.31(19) |
| C8 | C13 | C14 | C23 | −174.83(11) | C26 | C27 | C28 | C29 | −0.6(2) |
| C8 | C13 | C14 | C24 | 64.52(14) | C27 | C28 | C29 | C30 | −0.2(2) |
| C9 | C8 | C13 | C12 | 1.65(17) | C28 | C29 | C30 | N2 | −178.11(13) |
| C9 | C8 | C13 | C14 | −177.19(11) | C28 | C29 | C30 | C25 | 0.6(2) |
| C9 | C10 | C11 | C12 | 0.6(2) | C30 | N2 | C31 | C24 | 1.03(14) |
| C10 | C11 | C12 | C13 | 0.8(2) | C30 | C25 | C26 | C27 | −0.47(19) |
| C11 | C12 | C13 | C8 | −1.95(19) | C31 | N2 | C30 | C25 | −1.19(14) |
| C11 | C12 | C13 | C14 | 176.91(12) | C31 | N2 | C30 | C29 | 177.69(13) |
| C12 | C13 | C14 | C15 | 125.11(12) | C31 | C24 | C25 | C26 | −177.54(14) |
| C12 | C13 | C14 | C23 | 6.37(16) | C31 | C24 | C25 | C30 | −0.30(13) |

TABLE 21

Hydrogen Atom Coordinates (Å × 10⁴) and Isotropic Displacement Parameters (Å² × 10³) for 13.

| Atom | x | y | z | U(eq) |
|---|---|---|---|---|
| H1 | 6676(12) | 3411(17) | 6097(8) | 19 |
| H2 | 5264(13) | 3537(18) | 3736(9) | 25 |
| H2A | 6570 | 5560 | 4861 | 25 |
| H3 | 7242 | 6060 | 3972 | 31 |
| H5 | 9962 | 6589 | 5385 | 42 |
| H6 | 9301 | 6124 | 6288 | 32 |
| H7A | 8901 | 5976 | 3656 | 76 |
| H7B | 9826 | 6757 | 4202 | 76 |
| H7C | 8843 | 7643 | 3807 | 76 |
| H9 | 9121 | 3864 | 7098 | 26 |
| H10 | 10369 | 2125 | 7340 | 33 |
| H11 | 10004 | −150 | 6864 | 35 |
| H12 | 8411 | −681 | 6137 | 31 |
| H18 | 5436 | 3818 | 7049 | 25 |
| H19 | 4385 | 4401 | 7697 | 28 |
| H20 | 3050 | 2919 | 7680 | 28 |
| H21 | 2753 | 846 | 7005 | 28 |
| H22 | 3787 | 255 | 6346 | 25 |
| H23A | 6746 | −1255 | 5834 | 38 |
| H23B | 7145 | −902 | 5195 | 38 |
| H23C | 5977 | −826 | 5096 | 38 |
| H26 | 8473 | 758 | 4934 | 30 |
| H27 | 9060 | 1127 | 3993 | 39 |
| H28 | 8160 | 2492 | 3038 | 40 |
| H29 | 6624 | 3491 | 2990 | 33 |
| H31 | 5170 | 2707 | 4833 | 22 |

What is claimed is:

1. A pharmaceutical composition comprising an amount of a compound of formula:

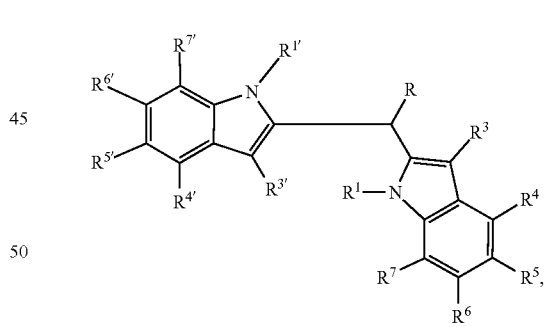

wherein $R^1$ and $R^{1\prime}$ are independently hydrogen or alkyl, provided that at least one of $R^1$ and $R^{1\prime}$ is hydrogen;

R is selected from the group consisting of halogen, hydroxyl, substituted or unsubstituted alkoxy, substituted or unsubstituted aryl, substituted or unsubstituted arylalkyl, substituted or unsubstituted heteroaryl, substituted or unsubstituted heteroarylalkyl, substituted or unsubstituted heterocyclyl, or substituted or unsubstituted heterocyclylalkyl; and $R^3$, $R^4$, $R^5$, $R^6$, $R^7$, $R^{3\prime}$, $R^{4\prime}$, $R^{5\prime}$, $R^{6\prime}$, and $R^{7\prime}$ are independently selected from hydrogen, halogen, hydroxyl, substituted or unsubstituted alkyl, substituted or unsubstituted alkoxy, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, or substituted or unsubstituted heterocyclylalkyl;

or a pharmaceutically suitable salt thereof;

in combination with a pharmaceutically suitable carrier;

wherein the amount is effective to modulate activity of arylhydrocarbon receptors in mammals, or the amount is effective to inhibit activity of PCSK9 in mammals, or the amount is effective to stimulate secretion of glucagon-like peptide 1 in mammals.

2. The pharmaceutical composition of claim 1, wherein $R^1$ and $R^{1\prime}$ are hydrogen.

3. The pharmaceutical composition of claim 1, wherein one of $R^1$ or $R^{1\prime}$ is hydrogen and the other of $R^1$ or $R^{1\prime}$ is alkyl.

4. The pharmaceutical composition of claim 1, wherein at least one of $R^3$, $R^4$, $R^5$, $R^6$, $R^7$, $R^{3\prime}$, $R^{4\prime}$, $R^{5\prime}$, $R^{6\prime}$, and $R^{7\prime}$ is not hydrogen.

5. The pharmaceutical composition of claim 1, wherein at least one of $R^3$, $R^4$, $R^5$, $R^6$, $R^7$, $R^{3\prime}$, $R^{4\prime}$, $R^{5\prime}$, $R^{6\prime}$, and $R^{7\prime}$ is selected from the group consisting of substituted or unsubstituted alkyl, substituted or unsubstituted alkoxy, and substituted or unsubstituted aryl.

6. A method to inhibit activity of proprotein convertase subtilisin/kexin type 9 (PCSK9) in mammals, the method comprising administering to the mammal a PCSK9 inhibitory-effective amount of a compound of formula:

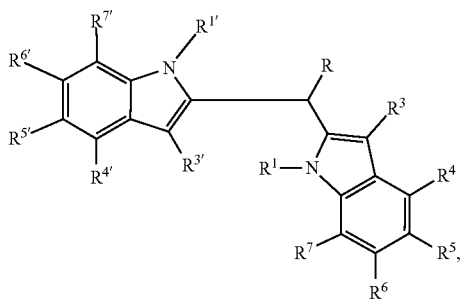

wherein $R^1$ and $R^{1\prime}$ are independently hydrogen or alkyl;

R is selected from the group consisting of halogen, hydroxyl, substituted or unsubstituted alkoxy, substituted or unsubstituted aryl, substituted or unsubstituted arylalkyl, substituted or unsubstituted heteroaryl, substituted or unsubstituted heteroarylalkyl, substituted or unsubstituted heterocyclyl, or substituted or unsubstituted heterocyclylalkyl; and $R^3$, $R^4$, $R^5$, $R^6$, $R^7$, $R^{3\prime}$, $R^{4\prime}$, $R^{5\prime}$, $R^{6\prime}$, and $R^{7\prime}$ are independently selected from hydrogen, halogen, hydroxyl, substituted or unsubstituted alkyl, substituted or unsubstituted alkoxy, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, or substituted or unsubstituted heterocyclylalkyl;

$R^{3\prime}$ may additionally be selected from acyl (—C(=O)H);

or a pharmaceutically suitable salt thereof.

7. A method to stimulate secretion of glucagon-like peptide 1 (GLP-1) in mammals, the method comprising administering to the mammal a GLP-1 secretion stimulative-effective amount of a compound of formula:

wherein $R^1$ and $R^{1\prime}$ are independently hydrogen or alkyl;

R is selected from the group consisting of halogen, hydroxyl, substituted or unsubstituted alkoxy, substituted or unsubstituted aryl, substituted or unsubstituted arylalkyl, substituted or unsubstituted heteroaryl, substituted or unsubstituted heteroarylalkyl, substituted or unsubstituted heterocyclyl, or substituted or unsubstituted heterocyclylalkyl; and $R^3$, $R^4$, $R^5$, $R^6$, $R^7$, $R^{3\prime}$, $R^{4\prime}$, $R^{5\prime}$, $R^{6\prime}$, and $R^{7\prime}$ are independently selected from hydrogen, halogen, hydroxyl, substituted or unsubstituted alkyl, substituted or unsubstituted alkoxy, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, or substituted or unsubstituted heterocyclylalkyl;

$R^{3\prime}$ may additionally be selected from acyl (—C(=O)H);

or a pharmaceutically suitable salt thereof.

* * * * *